United States Patent
Singer et al.

(10) Patent No.: US 11,414,712 B2
(45) Date of Patent: Aug. 16, 2022

(54) METHODS AND DEVICES FOR DETECTING AND IDENTIFYING MICROORGANISMS

(71) Applicant: HELIXBIND, INC., Worcester, MA (US)

(72) Inventors: Alon Singer, Waltham, MA (US); Ranjit Prakash, Northborough, MA (US); Srinivas Rapireddy, Westborough, MA (US); Jork Nolling, Hopedale, MA (US)

(73) Assignee: HELIXBIND, INC., Marlborough, MA (US)

( * ) Notice: Subject to any disclaimer, the term of this patent is extended or adjusted under 35 U.S.C. 154(b) by 75 days.

(21) Appl. No.: 15/511,957

(22) PCT Filed: Sep. 17, 2015

(86) PCT No.: PCT/US2015/050741
§ 371 (c)(1),
(2) Date: Mar. 16, 2017

(87) PCT Pub. No.: WO2016/044621
PCT Pub. Date: Mar. 24, 2016

(65) Prior Publication Data
US 2017/0292146 A1   Oct. 12, 2017

Related U.S. Application Data
(60) Provisional application No. 62/051,447, filed on Sep. 17, 2014.

(51) Int. Cl.
*C12Q 1/689* (2018.01)
*C12Q 1/6806* (2018.01)
(Continued)

(52) U.S. Cl.
CPC ........ *C12Q 1/689* (2013.01); *B01L 3/502715* (2013.01); *B01L 3/502738* (2013.01); *B01L 3/502753* (2013.01); *C12N 15/101* (2013.01); *C12Q 1/6806* (2013.01); *B01L 2200/028* (2013.01); *B01L 2200/0631* (2013.01);
(Continued)

(58) Field of Classification Search
None
See application file for complete search history.

(56) References Cited

U.S. PATENT DOCUMENTS 6,664,045 B1   12/2003   Hyldig-Nielsen et al.
2006/0003357 A1   1/2006   Mckernan et al.
(Continued)

FOREIGN PATENT DOCUMENTS

EP    2 333 105 A1    6/2011
WO   WO-2011/028494 A2   3/2011
(Continued)

OTHER PUBLICATIONS

Teixeira, L. et al. The ISME Journal 4:989 (Apr. 2010).*
(Continued)

*Primary Examiner* — Diana B Johannsen
(74) *Attorney, Agent, or Firm* — Foley & Lardner LLP

(57) ABSTRACT

Methods and devices for isolating microbial cells from a sample, extracting eukaryotic DNA from a sample, and identifying the microbial species in the sample are disclosed herein.

14 Claims, 40 Drawing Sheets
Specification includes a Sequence Listing.

(51) Int. Cl.
C12N 15/10 (2006.01)
B01L 3/00 (2006.01)

(52) U.S. Cl.
CPC ..... *B01L 2200/16* (2013.01); *B01L 2300/087* (2013.01); *B01L 2300/0877* (2013.01); *B01L 2400/0487* (2013.01); *B01L 2400/0633* (2013.01); *C12Q 2600/158* (2013.01); *C12Q 2600/16* (2013.01)

(56) References Cited

U.S. PATENT DOCUMENTS

| | | | |
|---|---|---|---|
| 2007/0054278 | A1 | 3/2007 | Cargill |
| 2008/0160528 | A1 | 7/2008 | Lorenz |
| 2009/0081675 | A1 | 3/2009 | Colston et al. |
| 2009/0142798 | A1 | 6/2009 | Lee et al. |
| 2011/0071031 | A1* | 3/2011 | Khripin ............ C12N 15/101 506/7 |
| 2012/0231446 | A1 | 9/2012 | Heckel et al. |
| 2012/0276530 | A1* | 11/2012 | Meller ............ C12Q 1/6839 435/6.11 |

FOREIGN PATENT DOCUMENTS

| | | |
|---|---|---|
| WO | WO-2011/087789 A2 | 7/2011 |
| WO | WO-2012/109587 A1 | 8/2012 |
| WO | WO-2013/176992 A2 | 11/2013 |
| WO | WO-2014/009151 A1 | 1/2014 |
| WO | WO-2014/025771 A2 | 2/2014 |

OTHER PUBLICATIONS

Teixeira, L. et al. GenBank Accession No. GU037269.1, Jul. 26, 2010.*
Stender, H. et al. Journal of Microbiological Methods 48:1-17. (Year: 2002).*
Chuanwu Xi, et al., "Use of molecular beacons for the detection of bacteria in microfluidic devices", Proceedings Optical Diagnostics of Living Cells II 4982: 170 (2003).
Tushar D. Rane, et al., "Droplet microfluidics for amplification-free genetic detection of single cells", Lab on a Chip 12(18): 3341 (2012).
International Search Report and Written Opinion for PCT/US2015/050741 dated Feb. 16, 2016.
Supplementary Partial European Search Report, dated Feb. 6, 2018, issued in corresponding European Patent Application No. 15842027.3.
European Examination Report, issued in EP Pat. App. No. 15842027.3, 3 pages (dated Mar. 21, 2019).
Extended Search Report on EP 20154925.0 dated Jun. 15, 2020.

* cited by examiner

LAYOUT 1: 18 WELL FOR EACH OF THE 23 PATHOGENS/PATHOGEN GROUPS USING A SINGLE EMISSIONS COLOR/WAVELENGTH.

| WELL # | PATHOGEN | WELL # | PATHOGEN |
|---|---|---|---|
| 1 | STAPHYLOCOCCUS AUREUS | 10 | SERRATIA MARCESCENS |
| 2 | STAPHYLOCOCCUS EPIDERMIDIS STAPHYLOCOCCUS LUGDUNENSIS | 11 | ACINETOBACTER BAUMANNII |
| 3 | ENTEROCOCCUS FAECALIS | 12 | ENTEROBACTER AEROGENES ENTEROBACTER CLOACAE KLEBSIELLA OXYTOCA KLEBSIELLA PNEUMONIAE |
| 4 | ENTEROCOCCUS FAECIUM | 13 | CANDIDA ALBICANS |
| 5 | STREPTOCOCCUS AGALACTIAE | 14 | CANDIDA GLABRATA |
| 6 | STREPTOCOCCUS PYOGENES | 15 | CANDIDA KRUSEI |
| 7 | STREPTOCOCCUS PNEUMONIAE | 16 | CANDIDA TROPICALIS |
| 8 | ESCHERICHIA COLI | 17 | CANDIDA PARAPSILOSIS |
| 9 | PSEUDOMONAS AERUGINOSA | 18 | STREPTOCOCCUS MITIS STREPTOCOCCUS ORALIS |

FIG. 30

LAYOUT 2: 6 WELLS FOR THE 21 PATHOGENS/PATHOGEN GROUPS USING A 3-COLOR FLUORESCENTLY SYSTEM.

| WELL # | PATHOGEN | DETECTION WAVELENGTH (COLOR) |
|---|---|---|
| 1 | STAPHYLOCOCCUS AUREUS | 488nm |
| 1 | STAPHYLOCOCCUS EPIDERMIDIS STAPHYLOCOCCUS LUGDUNENSIS | 532nm |
| 1 | ENTEROCOCCUS FAECALIS | 647nm |
| 2 | ENTEROCOCCUS FAECIUM | 488nm |
| 2 | STREPTOCOCCUS AGALACTIAE | 532nm |
| 2 | STREPTOCOCCUS PYOGENES | 647nm |
| 3 | STREPTOCOCCUS PNEUMONIAE | 488nm |
| 3 | ESCHERICHIA COLI | 532nm |
| 3 | PSEUDOMONAS AERUGINOSA | 647nm |
| 4 | SERRATIA MARCESCENS | 488nm |
| 4 | ACINETOBACTER BAUMANNII | 532nm |
| 4 | ENTEROBACTER AEROGENES ENTEROBACTER CLOACAE KLEBSIELLA OXYTOCA KLEBSIELLA PNEUMONIA | 647nm |
| 5 | CANDIDA ALBICANS | 488nm |
| 5 | CANDIDA GLABRATA | 532nm |
| 5 | CANDIDA KRUSEI | 647nm |
| 6 | CANDIDA TROPICALIS | 488nm |
| 6 | CANDIDA PARAPSILOSIS | 647nm |

FIG. 31

LAYOUT 3: 21 PATHOGENS/PATHOGEN GROUPS USING A SINGLE EMISSIONS COLOR/WAVELENGTH AND 11 WELLS.

| WELL # | PATHOGEN | WELL # | PATHOGEN |
|---|---|---|---|
| 1 | CANDIDA ALBICANS<br>CANDIDA GLABRATA<br>CANDIDA KRUSEI<br>CANDIDA TROPICALIS<br>CANDIDA PARAPSILOSIS | 6 | ESCHERICHIA COLI |
| 2 | ENTEROCOCCUS FAECALIS<br>ENTEROCOCCUS FAECIUM<br>STREPTOCOCCUS AGALACTIAE<br>STREPTOCOCCUS PYOGENES<br>STREPTOCOCCUS PNEUMONIAE | 7 | CANDIDA ALBICANS<br>ENTEROCOCCUS FAECALIS<br>PSEUDOMONAS AERUGINOSA |
| 3 | PSEUDOMONAS AERUGINOSA<br>SERRATIA MARCESCENS<br>ACINETOBACTER BAUMANNII<br>ENTEROBACTER AEROGENES<br>ENTEROBACTER CLOACAE<br>KLEBSIELLA OXYTOCA<br>KLEBSIELLA PNEUMONIAE | 8 | CANDIDA GLABRATA<br>ENTEROCOCCUS FAECIUM<br>SERRATIA MARCESCENS |
| 4 | STAPHYLOCOCCUS AUREUS | 9 | CANDIDA KRUSEI<br>STREPTOCOCCUS AGALACTIAE<br>ACINETOBACTER BAUMANNII |
| 5 | STAPHYLOCOCCUS EPIDERMIDIS<br>STAPHYLOCOCCUS LUGDUNENSIS | 10 | CANDIDA TROPICALIS<br>STREPTOCOCCUS PYOGENES<br>ENTEROBACTER AEROGENES<br>ENTEROBACTER CLOACAE<br>KLEBSIELLA OXYTOCA<br>KLEBSIELLA PNEUMONIAE |
| | | 11 | CANDIDA PARAPSILOSIS<br>STREPTOCOCCUS PNEUMONIAE |
| X | X | X | X |
| X | X | X | X |

FIG. 32

LAYOUT 4: 18 WELL SYSTEM FOR EACH OF THE 21 PATHOGENS/PATHOGEN GROUPS AND RESISTANCE IDENTIFICATION USING A SINGLE EMISSIONS COLOR/WAVELENGTH.

| WELL # | PATHOGEN | WELL # | PATHOGEN |
|---|---|---|---|
| 1 | STAPHYLOCOCCUS AUREUS | 10 | SERRATIA MARCESCENS |
| 2 | STAPHYLOCOCCUS EPIDERMIDIS STAPHYLOCOCCUS LUGDUNENSIS | 11 | ACINETOBACTER BAUMANNII |
| 3 | ENTEROCOCCUS FAECALIS | 12 | ENTEROBACTER AEROGENES ENTEROBACTER CLOACAE KLEBSIELLA OXYTOCA KLEBSIELLA PNEUMONIAE |
| 4 | ENTEROCOCCUS FAECIUM | 13 | CANDIDA ALBICANS |
| 5 | STREPTOCOCCUS AGALACTIAE | 14 | CANDIDA GLABRATA |
| 6 | STREPTOCOCCUS PYOGENES | 15 | CANDIDA KRUSEI |
| 7 | STREPTOCOCCUS PNEUMONIAE | 16 | CANDIDA TROPICALIS |
| 8 | ESCHERICHIA COLI | 17 | CANDIDA PARAPSILOSIS |
| 9 | PSEUDOMONAS AERUGINOSA | 18 | MecA/VanA/VanB/OxA-48/blaKPC/NDM-1 |

FIG. 33

LAYOUT 5: 12 WELL SYSTEM FOR EACH OF THE 21 PATHOGENS/PATHOGEN GROUPS AND RESISTANCE IDENTIFICATION USING A SINGLE EMISSIONS COLOR/WAVELENGTH.

| WELL # | PATHOGEN | WELL # | PATHOGEN |
|---|---|---|---|
| 1 | CANDIDA ALBICANS<br>CANDIDA GLABRATA<br>CANDIDA KRUSEI<br>CANDIDA TROPICALIS<br>CANDIDA PARAPSILOSIS | 6 | ESCHERICHIA COLI |
| | | 7 | CANDIDA ALBICANS<br>ENTEROCOCCUS FAECALIS<br>PSEUDOMONAS AERUGINOSA |
| 2 | ENTEROCOCCUS FAECALIS<br>ENTEROCOCCUS FAECIUM<br>STREPTOCOCCUS AGALACTIAE<br>STREPTOCOCCUS PYOGENES<br>STREPTOCOCCUS PNEUMONIAE | 8 | CANDIDA GLABRATA<br>ENTEROCOCCUS FAECIUM<br>SERRATIA MARCESCENS |
| | | 9 | CANDIDA KRUSEI<br>STREPTOCOCCUS AGALACTIAE<br>ACINETOBACTER BAUMANNII |
| 3 | PSEUDOMONAS AERUGINOSA<br>SERRATIA MARCESCENS<br>ACINETOBACTER BAUMANNII<br>ENTEROBACTER AEROGENES<br>ENTEROBACTER CLOACAE<br>KLEBSIELLA OXYTOCA<br>KLEBSIELLA PNEUMONIAE | 10 | CANDIDA TROPICALIS<br>STREPTOCOCCUS PYOGENES<br>ENTEROBACTER AEROGENES<br>ENTEROBACTER CLOACAE<br>KLEBSIELLA OXYTOCA<br>KLEBSIELLA PNEUMONIAE |
| | | 11 | CANDIDA PARAPSILOSIS<br>STREPTOCOCCUS PNEUMONIAE |
| 4 | STAPHYLOCOCCUS AUREUS | 12 | MecA/VanA/VanB/OxA-48/blaKPC/NDM-1 |
| 5 | STAPHYLOCOCCUS EPIDERMIDIS<br>STAPHYLOCOCCUS LUGDUNENSIS | X | X |

FIG. 34

LAYOUT 6 : 6 WELL SYSTEM FOR EACH OF THE 5 GRAM - NEGATIVE PATHOGENS/PATHOGEN GROUPS AND THEIR RESISTANCE IDENTIFICATION USING A SINGLE EMISSIONS COLOR/WAVELENGTH.

| WELL # | PATHOGEN | WELL # | PATHOGEN |
|---|---|---|---|
| 1 | ESCHERICHIA COLI | 4 | ACINETOBACTER BAUMANNII |
| 2 | PSEUDOMONAS AERUGINOSA | 5 | SERRATIA MARCESCENS |
| 3 | ENTEROBACTER AEROGENES ENTEROBACTER CLOACAE KLEBSIELLA OXYTOCA KLEBSIELLA PNEUMONIAE | 6 | OxA-48/blaKPC/NDM-1 |

FIG. 35

LAYOUT 7:
6 WELL SYSTEM FOR EACH OF THE 4 GRAM - POSITIVE PATHOGENS/PATHOGEN GROUPS AND THEIR RESISTANCE IDENTIFICATION USING A SINGLE EMISSIONS COLOR/WAVELENGTH.

| WELL # | PATHOGEN | WELL # | PATHOGEN |
|---|---|---|---|
| 1 | STAPHYLOCOCCUS AUREUS | 5 | MecA |
| 2 | STAPHYLOCOCCUS EPIDERMIDIS STAPHYLOCOCCUS LUGDUNENSIS | 6 | MecA |
| 3 | ENTEROCOCCUS FAECALIS | 7 | VanA/VanB |
| 4 | ENTEROCOCCUS FAECIUM | X | X |

FIG. 36

SEQUENCE LISTING

```
<160> NUMBER OF SEQ ID NOS: 45

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
tcgaagagca ggcaa                                                    15

<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
tcgaggttta ccaatg                                                   16

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
```

-continued gaggtattta ccaatg 16

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
aagtcaatga ttgcagg 17

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
ttgtcaatga gagtagg 17

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
tacacaatta atgagaa 17

<210> SEQ ID NO 7
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
gcaatcagag agaata 16

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
aattcgttta cagtacg 17

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
tcggatgata ccaatt                                                  16

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
gcagttactc gtttccata                                               19

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
cgcggtgatt ctagagt                                                 17

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
cgcggtgata ctagagt                                                 17

<210> SEQ ID NO 13
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13
aattcaagtg gtggaa                                                  16

<210> SEQ ID NO 14
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
aattcgagtg gtggaa                                                  16

<210> SEQ ID NO 15
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
ggtgatagag atccat                                                  16

<210> SEQ ID NO 16
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 16
ctcgttcgag agacac                                                     16

<210> SEQ ID NO 17
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
gtatttaccg atggg                                                      15

<210> SEQ ID NO 18
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
acgtaaggtc atgtgc                                                     16

<210> SEQ ID NO 19
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
gatctaaaag gtgcc                                                      15

<210> SEQ ID NO 20
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 20
tcaggcttct gtaac                                                      15

<210> SEQ ID NO 21
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21
agcggttttc cgatc                                                      15

```
<210> SEQ ID NO 22
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 22
tgcgtagttt tttcta                                                      16

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 23
cctgatggtc ccatagat                                                    18

<210> SEQ ID NO 24
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24
caggatcttt ggttgt                                                      16

<210> SEQ ID NO 25
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 25
gcattgatag gagatc                                                      16

<210> SEQ ID NO 26
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26
ccagggtaat tgagac                                                      16

<210> SEQ ID NO 27
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 27
cagtgttagc aactgc                                                      16
```

```
<210> SEQ ID NO 28
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 28
gtcctatcca tttgcat                                                  17

<210> SEQ ID NO 29
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 29
ctactcggac ttgcgc                                                   16

<210> SEQ ID NO 30
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 30
aaacgacagt ataacag                                                  17

<210> SEQ ID NO 31
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 31
tcgcaattca agaagg                                                   16

<210> SEQ ID NO 32
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 32
ttgtcccatc cattcg                                                   16

<210> SEQ ID NO 33
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 33
ggtttcctgc ttggac                                                   16

<210> SEQ ID NO 34
```

<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 34
tggctggagt gtcgg                                                      15

<210> SEQ ID NO 35
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 35
ctgaaccaca agtagga                                                    17

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 36
accaagctgt tgcgtaac                                                   18

<210> SEQ ID NO 37
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 37
agtacggaca acagtct                                                    17

<210> SEQ ID NO 38
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cccccccctc agttatcgtt tatttgatag tacc                                 34

<210> SEQ ID NO 39
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
cccccccctc agttatcgtt tatttgatag ttcc                                 34

<210> SEQ ID NO 40
<211> LENGTH: 28

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
cccttcccag agtttgatca tggctcag                                      28

<210> SEQ ID NO 41
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
cccttccaga gtttgatcct ggctcag                                       27

<210> SEQ ID NO 42
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42 cccccggtt accttgttac gactt                                          25

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43 ccccggcta ccttgttacg actt                                           24

<210> SEQ ID NO 44
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
cccttccctg atgactcgtg cctacta                                       27

<210> SEQ ID NO 45
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ccctctccct gatgacttgc gcttacta                                      28
```

METHODS AND DEVICES FOR DETECTING AND IDENTIFYING MICROORGANISMS

CROSS REFERENCE

This application is a 35 U.S.C. § 371 National Phase Application of PCT/US2015/050741, filed Sep. 17, 2015, which claims the benefit of and priority to U.S. Provisional Application No. 62/051,447 filed Sep. 17, 2014, the contents of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Oct. 16, 2015, is named 104341-0505_SL.txt and is 10,418 bytes in size.

GOVERNMENT SUPPORT

This invention was made with government support under contracts No. R43-OD016466 and No. R43AI109913 awarded by the National Institutes of Health (NIH). The government has certain rights in the invention.

BACKGROUND

The following description is provided to assist the understanding of the reader. None of the information provided or references cited is admitted to be prior art to the compositions and methods disclosed herein.

Bloodstream infections (BSIs) have risen to become the 6th leading cause of death in the U.S. and the most expensive hospital-treated condition. BSIs account for 25% of all ICU usage and roughly 50% of all hospital deaths in the U.S. BSIs are typically caused by bacteria or fungi, and effective disease management requires their early and accurate identification. BSIs are typically identified through a series of blood-cultures that take up to several days to identify potential pathogens.

Molecular diagnostics provide the caregiver with highly detailed information in a timely manner. In the case of infectious diseases, identification of the infecting pathogen is important when prescribing a treatment protocol because several pathogens often induce similar pathophysiological symptoms. However, many pathogen species invariably respond drastically different to potential lines of treatment.

Molecular diagnostic methods for identifying microbial pathogens can be performed by probing for conserved regions in their respective genomic material. Methods for genomic identification include isolation and detection of pathogenic DNA.

SUMMARY

In one aspect, the present technology provides methods for identifying one or more specific microbial species in a sample from a subject, wherein the method includes: depleting eukaryotic DNA from the sample; lysing one or more microbial cells in the sample, wherein the lysing of one or more microbial cells releases a plurality of microbial genetic materials; isolating the plurality of microbial genetic materials; amplifying the plurality of microbial genetic materials; contacting the amplified microbial genetic materials with a plurality of DNA Invading Artificial Nucleic Acids (DIANAs), wherein the plurality of DIANAs comprise a sequence selected from the group consisting of SEQ ID NOS: 1-37; and detecting binding of one or more DIANAs the microbial genetic material of its respective single species or group of microbes, wherein the detection of binding indicates the presence of one or more specific microbial species or groups of microbes in the sample.

In some embodiments, the isolated plurality of genomic materials are purified.

In some embodiments, depleting eukaryotic DNA from the sample includes adding an eukaryotic cell lysis solution to the sample, wherein the eukaryotic cell lysis solution selectively targets and predominantly lyses eukaryotic cells as opposed to microbial cells.

In some embodiments, eukaryotic cell lysis solution combined with the sample comprises between about 0.25% to 1% (v/v) of a Tween surfactant, between about 0.2% to 0.65% (v/v) of Triton or IGEPAL, and has pH of about 6-9.

In some embodiments, the free eukaryotic DNA is removed from the blood reaction using an anionic-exchange microparticle under conditions of a pH of about 6-9 with monovalent salt concentrations of about 0.1 M-0.85 M.

In some embodiments, the sample is blood or sputum.

In some embodiments, the subject is a mammal. In some embodiments, the mammal is a human.

In some embodiments, isolating the plurality of microbial genetic materials includes binding the microbial genetic material to an anionic-exchange microparticle and washing the anion-exchange microparticle after binding the microbial genetic material.

In some embodiments, the isolated microbial genetic material is RNA, DNA, or a combination thereof. In some embodiments, the DNA is single stranded or double stranded.

In some embodiments, lysing one or more microbial cells in the sample comprises contacting the one or more microbial cells with a lysis buffer comprising a DNA intercalating dye.

In some embodiments, the DNA intercalating dye is selected from ethidium monazide (EMA), propidium monoazide (PMA), or a combination thereof.

In some embodiments, the washing the anion-exchange microparticle after binding the microbial genetic material comprises contacting the isolated plurality of microbial genetic materials with a wash buffer comprising a pH between about 3 to 7.5, at least one monovalent salt, wherein the monovalent salt concentration is between about 0.75 M to 2.75 M, at least one non-ionic detergent, wherein the non-ionic detergent concentration is between about 0.01% to 1.0% (v/v), and a least one zwitterionic detergent, wherein the zwitterionic detergent concentration is between about 0.1× to 400×CMC.

In some embodiments, amplifying the plurality of microbial genetic materials comprising creating amplicons between about 400 to 2000 bp.

In some embodiments, the DIANAs comprise one or more linkers. In some embodiments, the linkers are between about 40 to 200 atoms in length.

In some embodiments, the DIANAs comprise one or more binding moieties.

In another aspect, the present technology provides devices including: a cartridge, wherein the cartridge comprises a plurality of interconnected chambers enabling multidirectional flow, wherein a first chamber is a reaction chamber, wherein the first chamber is configured to accept a sample between about 10 μl to 10 ml; wherein a second chamber is lysis solution storage chamber; wherein a third chamber is a lysis termination solution storage chamber; wherein a fourth chamber is an anion exchange resin storage chamber; and wherein a fifth chamber is an output chamber; and a fluidic device, wherein the fluidic device comprises a plurality of flow channels, wherein a first flow channel connects the first chamber to the second chamber, wherein a second flow channel connects the first chamber to the third chamber, wherein a third flow channel connects the first chamber to the fourth chamber, and wherein a fourth flow channel connects the first chamber to the fifth chamber.

In some embodiments, the fluidic device further comprises flow-gates, wherein the flow gates are disposed between flow channels connecting two or more chambers.

In some embodiments, the fluidic device further comprises one or more pneumatic interfaces, wherein the pneumatic interfaces are in fluid connection to at least one chamber.

In some embodiments, the anion exchange resin storage chamber comprises an anion exchange resin.

In some embodiments, the anion exchange resin storage chamber comprises an anion exchange resins conjugated to a support substrate.

In some embodiments, the lysis solution storage chamber comprises an eukaryotic lysis solution, wherein the eukaryotic lysis solution combined with the sample comprises between about 0.25% to 1% (v/v) of a Tween surfactant and between about 0.2% to 0.65% (v/v) of Triton or IGEPAL.

In some embodiments, the Tween surfactant is selected from the group consisting of Tween-20, Tween-40, and Tween-80. In some embodiments, the Triton is Triton X-100 or Triton X-114.

In some embodiments, the IGEPAL is selected from the group consisting of IGEPAL CO-520, IGEPAL CO-630, and IGEPAL CO-720.

In some embodiments, the fluid agitation is produced by a flow of a sterile gas into one or more of the chambers.

In some embodiments, the device is a standalone device. In some embodiments, the device is a module in a second device, wherein the second device performs upstream and/or downstream processing of the module.

In another aspect, the present technology provides a composition including one or more DIANAs, wherein the DIANAs have a sequence selected from the group consisting of SEQ ID NO: 1-37.

In some embodiments, the one or more DIANAs are bound to a solid support.

In some embodiments, the one or more DIANAs include a detectable marker.

In another aspect, the present technology provides a method for depleting eukaryotic DNA from the sample comprises adding an eukaryotic cell lysis solution to the sample, wherein the eukaryotic cell lysis solution selectively targets and predominantly lyses eukaryotic cells as opposed to microbial cells using a device that includes a cartridge, wherein the cartridge comprises a plurality of interconnected chambers enabling multidirectional flow, wherein a first chamber is a reaction chamber, wherein the first chamber is configured to accept a sample between about 10 μl to 10 ml; wherein a second chamber is lysis solution storage chamber; wherein a third chamber is a lysis termination solution storage chamber; wherein a fourth chamber is an anion exchange resin storage chamber; and wherein a fifth chamber is an output chamber; and a fluidic device, wherein the fluidic device comprises a plurality of flow channels, wherein a first flow channel connects the first chamber to the second chamber, wherein a second flow channel connects the first chamber to the third chamber, wherein a third flow channel connects the first chamber to the fourth chamber, and wherein a fourth flow channel connects the first chamber to the fifth chamber.

BRIEF DESCRIPTION OF THE DRAWINGS

FIG. 30 is an exemplary, non-limiting layout of an 18 well system that can analyze for each of 23 pathogens/pathogen groups using a single emissions color/wavelength.

FIG. 31 is an exemplary, non-limiting layout of a 6 well system that can analyze for each of 21 pathogens/pathogen groups using a 3-color fluorescently system.

FIG. 32 is an exemplary, non-limiting layout of an 11 well system that can analyze for each of 21 pathogens/pathogen groups using a single emissions color/wavelength.

FIG. 33 is an exemplary, non-limiting layout of an 18 well system that can analyze for each of 21 pathogens/pathogen groups using a single emissions color/wavelength.

FIG. 34 is an exemplary, non-limiting layout of a 12 well system that can analyze for each of 21 pathogens/pathogen groups using a single emissions color/wavelength.

FIG. 35 is an exemplary, non-limiting layout of a 6 well system that can analyze for each of 5 Gram-Negative pathogens/pathogen groups and their resistance identification using a single emissions color/wavelength.

FIG. 36 is an exemplary, non-limiting layout of a 6 well system that can analyze for each of 4 Gram-Negative pathogens/pathogen groups and their resistance identification using a single emissions color/wavelength.

DETAILED DESCRIPTION

Figure 1:
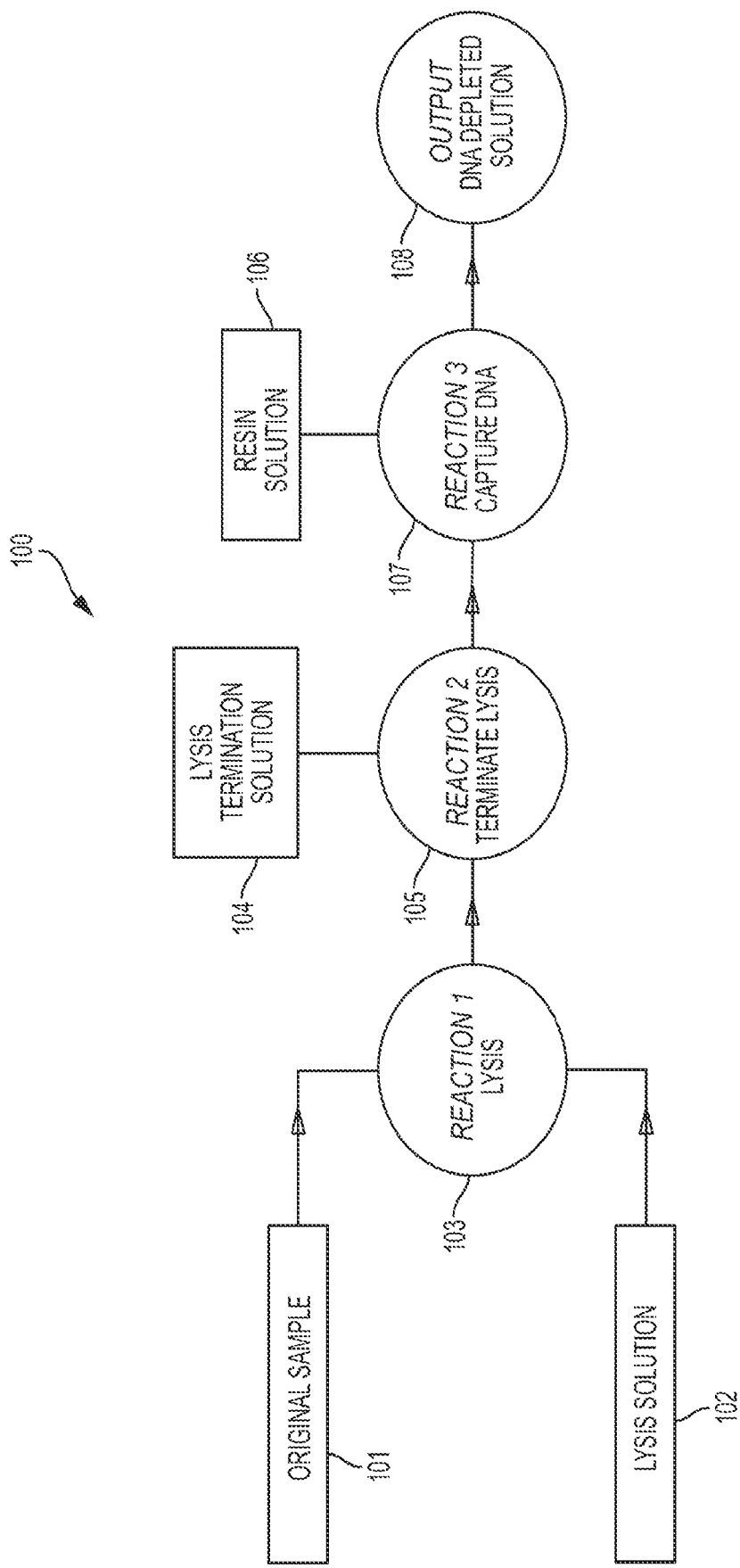
FIG. 1 is a schematic displaying an exemplary, non-limiting process for removing eukaryotic DNA from a solution.

The various aspects and embodiments of the present technology that are introduced above and discussed in greater detail below may be implemented in any number of ways, and as described herein, are not limited to any particular manner of implementation. Examples of specific implementations and applications are provided primarily for illustrative purposes.

As used herein, the singular forms "a," "an," and "the" include plural referents unless the content clearly dictates otherwise. For example, reference to "a cell" includes a combination of two or more cells, and the like.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

As used herein, "atom" refers to a carbon atom, a nitrogen atom, an oxygen atom, or any atom capable of making two or more covalent bonds. Alternatively, in some embodiments, "atom" refers to the distance between two covalently bound atoms. By way of example, but not by way of limitation, the following structure: DIANA-$(CH_2)_{40}$-(binding moiety) has a linker (—$(CH_2)_{40}$—) with a length of 40 atoms. By way of example, but not by way of limitation, the following structure: DIANA-$(CH_2)_{40}$—O—$(CH_2)_{40}$-(binding moiety) has a linker (—$(CH_2)_{40}$—O—$(CH_2)_{40}$—) with a length of 81 atoms. By way of example, but not by way of limitation, the following structure: DIANA-$(CH_2)_{40}$—O—NH—$(CH_2)_{30}$-(binding moiety) has a linker (—$(CH_2)_{40}$—O—NH—$(CH_2)_{30}$—) with a length of 72 atoms. By way of example, but not by way of limitation, the following structure: DIANA-$(CH_2)_{40}$—O—N$(CH_2)_3CH_3$—$(CH_2)_{30}$-(binding moiety) has a linker (—$(CH_2)_{40}$—O—N$(CH_2)_3CH_3$—$(CH_2)_{30}$—) with a length of 72 atoms (the —$(CH_2)_3CH_3$ component branches off of the nitrogen atom and does not contribute to the length of the linker).

As used herein, the term "invasion" refers to the binding of DNA Invading Artificial Nucleic Acids (DIANAs) to (either locally or universally) double-stranded or duplex genomic material (e.g., RNA or DNA) through Watson-Crick basepairing.

As used herein, the term "multidirectional flow" refers to allowing the flow of fluids or samples in more than one direction. By way of example, but not by way of limitation, in some embodiments, there is multidirectional flow between two chambers, e.g., chamber 1 and chamber 2, of a device when fluids or samples can flow from chamber 1 to chamber 2 and from chamber 2 to chamber 1. In some embodiments, the multidirectional flow is within a single tube or flow channel connecting the two chambers. In some embodiments, the multidirectional flow is achieved by more than one tube or flow channel connecting the two chambers.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same General Typically molecular diagnostics for infectious disease require access to the genomic material of a pathogen, i.e., its DNA or RNA. Most methods include lysing the microbial organisms (for example, mechanically, chemically, or through a combination of both), thereby extracting their genomic material. Methods or commercial kits are used to purify the genomic material from salts, buffers and additional cellular debris to yield a pure or a clean genomic product ready for further processing, e.g., amplification and detection.

In some molecular diagnostics, whole-blood is used as the starting material or sample. Whole blood is a complex solution that contains multiple cell types such as leukocytes, erythrocytes, and thrombocytes, as well as, naturally occurring organic and inorganic components. The blood components hinder (and may even completely prevent) additional or downstream processing of DNA and/or RNA, such as, e.g., enzymatic PCR or isothermal amplification. Additionally, anticoagulants and preservatives, which are commonly used during bodily fluid sample collection, can further interfere with enzymatic processing.

When human DNA (hDNA) in whole blood is to be subjected to enzymatic amplification (e.g., PCR or isothermal amplification), some commercially available kits reduce the hDNA purification steps by enabling a simple heat-shock to lyse the leukocytes, thereby exposing the genomic material to a blood/buffer solution. These kits typically only enable the processing of 5-20% whole blood in a typical reaction before sensitivity is drastically compromised; thus the kits usually limit the volume of tested blood in a single reaction to about 20 µl. When the hDNA is to be amplified before detection, the low sample volume is not a limitation as sufficient hDNA can be recovered to successfully perform enzymatic amplification processes.

However, in cases where blood is used as a sample for molecular diagnostics to identify pathogens present in blood, limiting the test sample volume to tens of microliters is disadvantageous, especially if the pathogen is present in very low concentrations in the blood sample. By way of example, but not by way of limitation, the load level (defined as the number of microbial pathogens present in a unit volume of blood) of microbial pathogens infecting human blood, can be as low as 10 cells/ml in whole-blood, whereas a typical milliliter of human whole-blood contains about $4\times10^6$-$11\times10^6$ leukocytes or white blood cells (WBCs). Taking into account the size of the human genome, the hDNA content in 1 ml of human whole-blood typically ranges from 20-60 µg, whereas the mass of the microbial DNA in 1 ml of blood typically ranges from 50 fg-50 pg.

The present technology generally relates to methods and devices for isolating, detecting, and/or identifying microbial cells in a sample. In some embodiments, the methods and devices can identify one or more species of microbial cells in the sample. In some embodiments, the detection and identification of microbial cells in the sample includes remove eukaryotic DNA from the sample. In some embodiments, the present technology provides methods and devices that provide highly sensitive detection of microbes in fluid volumes, e.g., about 1 ml, of samples. In some embodiments, the present technology discloses methods and devices for increasing detection sensitivity of microbial pathogens present in bodily fluids by selectively removing human nucleic acid prior to sensitive detection of microbial infection. In some embodiments, the methods of the present technology are fully automated and do not require standard laboratory processes, e.g., conventional centrifugation to extract DNA.

In another aspect, the present technology describes methods and devices for diagnosing bloodstream infections that does not require a culturing step. In some embodiments, the methods and devices detect and identify a panel of microorganisms at clinically relevant load levels directly from a blood sample and without culturing the blood sample.

Methods for Isolating, Detecting, and Identifying Microbes in a Sample

In some embodiments, the present technology provides a method for isolating, detecting, and/or identifying microbial cells in a sample. In some embodiments, the method includes one or more of the following steps: depleting eukaryotic DNA from the sample, lysing one or more microbial cells in the sample, wherein the lysing of one or more microbial cells releases a plurality of microbial genetic materials, isolating the plurality of microbial genetic materials, amplifying the plurality of microbial genetic materials, contacting the amplified microbial genetic materials with a plurality of duplex DNA Invading Artificial Nucleic Acids (DIANAs), wherein each DIANA targets the microbial genetic material of a specific pathogen or group of pathogens, and detecting binding of one or more DIANAs to their target microbial genetic material, wherein the detection of binding indicates the presence of one or more specific microbial species.

Figure 37:
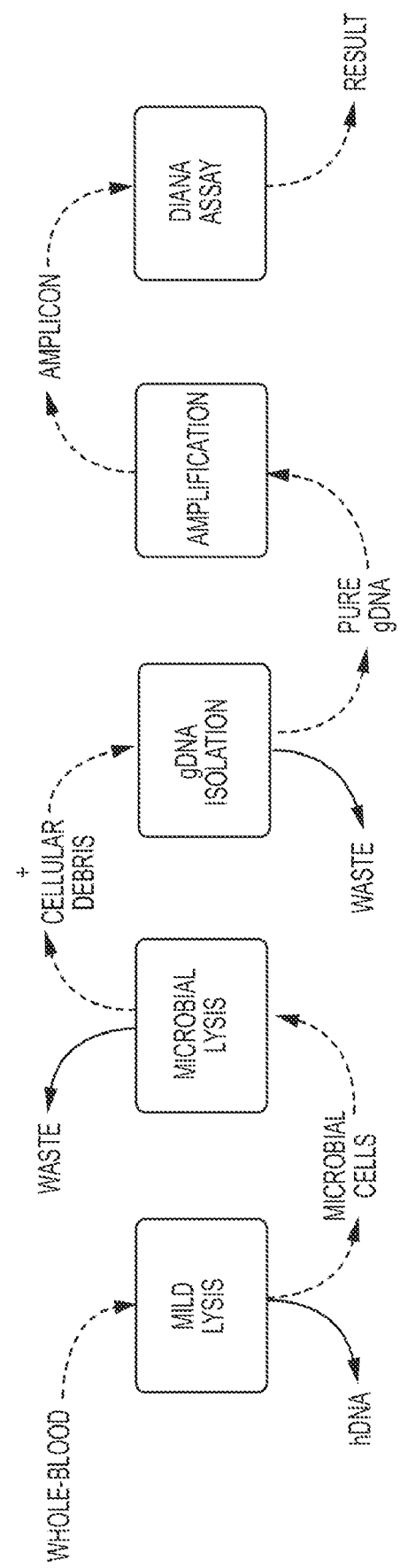
FIG. 37 is an exemplary, non-limiting diagram for isolating, detecting, and identifying microbes in a sample, wherein hDNA is human DNA and gDNA is microbial DNA.

In some embodiments, the method includes a five step process (see FIG. 37): (1) Mild or Selective Eukaryotic Cell Lysis; (2) Pathogen Lysis; (3) Capture Isolation and Purification of Microbial Genomic Material; (4) Enzymatic Amplification; and (5) DNA Invading Artificial Nucleic Acid (DIANA) based detection and identification. In some embodiments, the above method also allows for the identification of microbial pathogens at clinically relevant microbial load levels directly from unprocessed blood without having to conduct blood culturing processes. In some embodiments, the entire process (i.e., steps 1-5) requires less than about 8 hours. In some embodiments, the entire process requires between about 1 to 5 hours. In some embodiments, the entire process requires about 2 to 4 hours.

By way of example, but not by way of limitation, and without wishing to be bound by theory, in some embodiments, the exemplary five step method, disclose above, and the embodiments of each exemplary step, described herein, provide the following advantages:

Step 1) The methods for removing eukaryotic DNA through selective eurkaryotic cell lysis, described herein, are readily automatable onto a closed fluidic cartridge, which enables a human-intervention free process that is contamination-free and reduce false positives due to either cross-contamination or DNAemia.

Step 2) The methods for microbial cell lysis, described herein, produce long (e.g., 2 kbp to 290 kbp) microbial genomic material (e.g., DNA or RNA) from one or more microbes (e.g., bacterial and/or fungal cells) rapidly and with high yield. In some embodiments, the microbial cell lysis methods, described herein, produce long microbial genomic material that both interact strongly and are readily released from anion exchange resins during the downstream isolation and purification of microbial genomic material as described herein.

Step 3) In some embodiments, the methods for purification of long microbial genomic material, described herein, provide conditions that preferably enable long microbial genomic material isolation via anion exchange resins and simultaneously result in highly pure genomic material. Purification of highly pure, and long microbial genomic material allows for the efficient production of long amplicons in the downstream amplification processes described herein.

Figure 38:
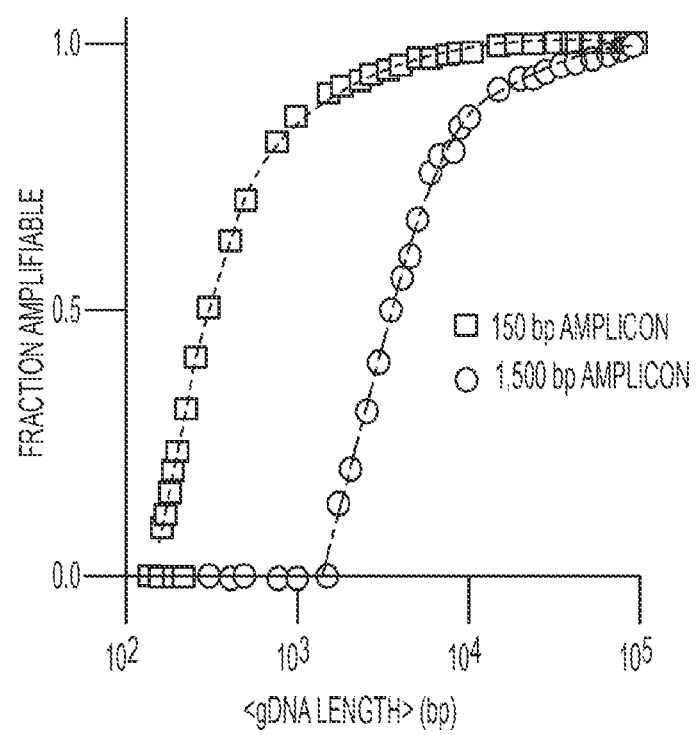
FIG. 38 is graph showing that use of a full-length (about 1.5 kbp) 16S/18S amplicon (ribosomal DNA) is advantageous in reducing background levels generated by random DNA contaminations. In-silico simulations (n=10,000 simulations for each data point) highlight that shorter fragments are significantly more likely to be amplifiable than longer fragments. As contaminations are typically of poor-quality (low molecular weight), targeting a longer amplicon (e.g., a 1.5 kbp amplicon) can reduce the possibility of amplifying the contaminating DNA. gDNA in the chart refers to randomly sheared microbial DNA.

Step 4) In some embodiments, production of long amplicons (e.g., between about 400 bp to 4000 bp) increases sensitivity to DIANAs as amplifying long amplicons reduces the likelihood of amplifying environmental contaminants (see FIG. 38). The production of long amplicons during an amplification step for hybridization is generally taught away from in the art, as production of long amplicons is less efficient as compared to amplifying short amplicons.

Step 5) In some embodiments, use of DIANAs enables the targeting of highly conserved genomic regions which are free of both inter-genomic variations as well as inter-species variations for a broad panel of microorganisms with high levels of detail. Further, use of DIANAs to invade and probe long amplicons is not hindered due to the formation of internal secondary structures in the DNA, which would interfere during hybridization of DNA probes.

In some embodiments, the above methods provide the advantages of immobilization of long duplex DNA with high efficiency and selectivity to a solid substrate.

In some embodiments, the microbial cells in the sample or suspected of being in the sample, include, but are not limited to bacterial cells, fungal cells, viral particles, or a combination thereof.

In some embodiments, the sample is a bodily fluid, bodily secretion, or a bodily excretion. By way of example, but not by way of limitation, in some embodiments, the sample includes, but is not limited to, stool, sputum, urine, blood.

In some embodiments, the sample is about 1 µl, 10 µl, 20 µl, 30 µl, 40 µl, 50 µl, 60 µl, 70 µl, 80 µl, 90 µl, 100 µl, or any amount between any two of the previously listed amounts. In some embodiments, the sample is between about 100 µl to 2.5 ml, about 200 µl to 2 ml, about 300 µl to 1.5 ml, about 400 µl to 1 ml, or about 500 µl to 750 µl. In some embodiments, the sample is between about 0.5 ml to 10 ml, about 1 ml to 9 ml, about 2 ml to 8 ml, about 3 ml to 7 ml, or about 4 ml to 6 ml.

In some embodiments, the sample is from a subject. Subjects include, but are not limited to, mammals, avians, reptiles, insects, amphibians, and fish. In some embodiments, a mammalian subject is human.

In some embodiments, the present technology provides methods for detecting the presence or microbes in a sample. In some embodiments the method includes adding a mild or selective cell lysis agent to the sample, wherein the cell lysis agent predominantly lyses eukaryotic cells as compared to microbial cells and leave a majority of the microbial cells intact, removing the eukaryotic DNA released by the lysis of the eukaryotic cells from the sample wherein isolated microbial cells remain in the sample, and subjecting the isolated microbial cells to molecular diagnostics. By way of example, but not by way of limitation, in some embodiments, molecular diagnostics includes lysing the isolated microbial cells, isolating the microbial DNA or RNA, and identifying the genomic material using nucleic acid probes, direct-sequencing, or any other method known in the art for identifying genomic material. In some embodiments, the isolated microbial DNA or RNA is subjected to amplification, targeted or untargeted. In some embodiments, the method for detecting microbial presence also includes terminating the lysis reaction.

In some embodiments, the sample is from a subject. Subjects include, but are not limited to, mammals, avians, reptiles, insects, amphibians, and fish. In some embodiments, the subject is human.

In some embodiments, the microbial cells in the sample or suspected of being in the sample, include, but are not limited to bacterial cells, fungal cells, viral particles, or a combination thereof.

In some embodiments, the sample is a bodily fluid, bodily secretion, or a bodily excretion. By way of example, but not by way of limitation, in some embodiments, the sample includes, but is not limited to, stool, sputum, urine, and blood.

In some embodiments, the sample is between about 1 µl to 50 µl, about 10 µl to 3.0 ml, about 20 µl to 2.5 ml, about 30 µl to 2.0 ml, about 40 µl to 1.5 ml, about 50 µl to 1.0 ml, about 60 µl to 90 µl, about 70 µl to 80 µl, or about 0.5 ml to 10 ml.

Depleting Eukaryotic Cells from the Sample

In some embodiments, depleting eukaryotic DNA from the sample includes adding a eukaryotic cell lysis solution to the sample, wherein the eukaryotic cell lysis solution predominantly lyses eukaryotic cells as opposed to microbial cells and removing the eukaryotic DNA released by the lysis of the eukaryotic cells from the sample, wherein one or more intact microbial cells remain in the sample. In some embodiments, the method includes terminating the eukaryotic cell lysis reaction.

Lysis of Eukaryotic Cells

In some embodiments, the eukaryotic cell lysis agent is a solution (hereinafter "a eukaryotic cell lysis solution"). Alternatively, in some embodiments, the eukaryotic cell lysis agent is pelleted and re-suspended in water or an aqueous buffer prior to use.

In some embodiments, the eukaryotic cell lysis solution includes one or more detergents or surfactants. In some embodiments, the detergents or surfactants are non-ionic, anionic, cationic, zwitterionic, or non-detergent sulfobetaines. Detergents and surfactants, include, but are not limited to BigCHAP, Deoxy BigCHAP, Brij 35, Brij 58P, Cymal-1, Cymal-2, Cymal-5, Cymal-6, Decyl-β-maltopyranoside, n-Dodecyl-β-D-maltoside, n-Hexadecyl-β-D-maltoside, Undecyl-β-D-maltoside, Decyl-β-D-1-thiomaltopyranoside, Octyl-β-D-glucopyranoside, Decyl-β-D-1-thioglucopyranoside, Octyl-β-Dthioglucopyranoside, Digitonin, Dimethyldecylphosphine oxide (APO-10), Dodecyldimethylphosphine oxide (APO-12), IGEPAL CO-520, IGEPAL CO-630, and IGEPAL CO-720, N-Octanoyl-N-methylglucamine(MEGA-8), N-nonanoyl-N-methylglucamine(MEGA-9), N-Decanoyl-N-methylglucamine(MEGA-10), nonidet P40-substitute, Pluronic F-68, saponin, thesit, Triton X-100, Triton X-114, TWEEN 20, TWEEN 40, TWEEN 80, sodium cholate, Sodium deoxycholate, sodium glycocholate, sodium taurocholate, sodium taurodeoxycholate, N-1-lauroylsarcosine, lithium dodecyl sulfate, sodium dodecyl sulfate (SDS), hexadecyltrimethyl ammonium bromide (CTAB), trimethyl(tetradecyl) ammonium bromide (TTAB), ASB-14(amidosulfobetaine-14), ASB-16(amidosulfobetaine-16), C7BzO, CHAPS, CHAPSO, EMPIGEN BB, 3-(N,N-Dimethyloctylammonio) propanesulfonate inner salt (SB3-8), 3-(decyldimethylammonio)-propanesulfonate inner salt (SB3-10), 3-(dodecyldimethylammonio)-propanesulfonate inner salt (SB3-12), 3-(N,N-dimethylmyristylammonio)-propanesulfonate(SB3-

14), 3-(N,N-dimethylpalmitylammonio)-propanesulfonate (SB3-16), 3-(N,N-dimethyloctadecylammonio)-propanesulfonate(SB3-18), 3-(1-pyridinio)-1-propanesulfonate (NDSB 201), and 3-(benzyldimethylammonio) propanesulfonate (NDSB 256).

By way of example, but not by way of limitation, in some embodiments, the eukaryotic cell lysis solution has a concentration of surfactants between about 0.27% to 15% v/v, between about 0.39% to 13% v/v, between about 0.45% to 12% (v/v), or between about 0.60% to 10% (v/v) of a Tween surfactant and/or between about 0.22% to 10% (v/v), between about 0.16% to 8.25% (v/v), or between about 0.44% to 6.75% (v/v) of Triton or IGEPAL. In some embodiments, the Tween surfactant is selected from the group consisting of Tween-20, Tween-40, and Tween-80. In some embodiments, the Triton is Triton X-100 or Triton X-114. In some embodiments, the IGEPAL is selected from the group consisting of IGEPAL CO-520, IGEPAL CO-630, and IGEPAL CO-720.

In some embodiments, the surfactants are stored individually in dry form and re-suspended prior to use.

By way of example, but not by way of limitation, in some embodiments, the eukaryotic cell lysis reaction (e.g., eukaryotic cell lysis solution combined with the sample (herein after the "mixture")) comprise a final concentration of surfactants between about 0.25% to 1% (v/v), between about 0.35% to 0.85% (v/v), between about 0.45% to 0.75% (v/v), or between about 0.55% to 0.65% (v/v) of a Tween surfactant and/or between about 0.15% to 0.65% (v/v), between about 0.25% to 0.55% (v/v), or between about 0.35% to 0.45% (v/v) of Triton or IGEPAL. In some embodiments, the Tween surfactant is selected from the group consisting of Tween-20, Tween-40, and Tween-80. In some embodiments, the Triton is Triton X-100 or Triton X-114. In some embodiments, the IGEPAL is selected from the group consisting of IGEPAL CO-520, IGEPAL CO-630, and IGEPAL CO-720.

In some embodiments, the detergent or detergents reduce the structural integrity of the eukaryotic cell.

In some embodiments, at least one anti-foaming agent is combined with the eukaryotic cell lysis solution. Anti-foaming agents include, but are not limited to, Antifoam A, Antifoam 204, Antifoam B, Antifoam C, Antifoam Y-30, Antifoam SE-15, and simethicone-based antifoams.

In some embodiments, the mixture contains less than about 0.15 M of monovalent salts. Without wishing to be bound by theory, in some embodiments, when the mixture contains less than about 0.15 M of monovalent salts there is an induction of osmotic stress. In some embodiments, the mixture includes between about 0.15 M to 0.75 M, about 0.2 M to 0.7 M, about 0.25 M to 0.65 M, about 0.3 M to 0.6 M, about 0.35 M to 0.55 M, or about 0.4 M to 0.5 M or monovalent salts.

In some embodiments, the volume ratio of the eukaryotic cell lysis solution to the sample is about 0.25:1, 0.5:1, 0.75:1, 1:1, 2:1, 3:1, 4:1, 5:1, 6:1, 7:1, 8:1, 9:1, 10:1, or any ratio between any two of these ratios.

In some embodiments, the eukaryotic cell lysis reaction is carried out at about room temperature. In some embodiments, the eukaryotic cell lysis reaction is carried out at between about 5° C. to 20° C., about 9° C. to 16° C., or about 12° C. to 13° C. In some embodiments, the eukaryotic cell lysis reaction is carried at temperatures between about 25° C. to 75° C., about 30° C. to 70° C., about 35° C. to 65° C., about 40° C. to 60° C., or about 45° C. to 55° C.

In some embodiments, the eukaryotic cell lysis reaction is carried out for between about 0.01-20 minutes, between about 0.1-9.0 minutes, between about 1.0-8.0 minutes, between about 2.0-7.0 minutes, between about 3.0-6.0 minutes, between about 4.0-5.0 minutes. In some embodiments, the eukaryotic cell lysis process is stopped after about 5 minutes.

In some embodiments, the eukaryotic cell lysis solution does not contain a buffering agent. In other embodiments, the eukaryotic cell lysis solution contains a buffering agent. Examples of buffering agents include, but are not limited to 2-(N-morpholino)ethanesulfonic acid (MES), 2-Bis(2-hydroxyethyl)amino-2-(hydroxymethyl)-1,3-propanediol (Bis-Tris), 3-(N-morpholino)propanesulfonic acid (MOPS), 4-(2-hydroxyethyl)-1-piperazineethanesulfonic acid (HEPES), tris(hydroxymethyl)aminomethane) (TRIS), Sodium Phosphate, Potassium Phosphate, Sodium Acetate, Sodium Carbonate/Bicaronate buffers, Sodium Acetate, N-cyclohexyl-2-hydroxyl-3-aminopropanesulfonic acid (CAPSO), N-(2-Hydroxyethyl)piperazine-N'-(4-butanesulfonic acid) (HEPBS), N-methylpiperazine, piperazine, diethanolamine, and propane 1,3-diamino.

In some embodiments, the pH of the eukaryotic cell lysis reaction is between about a pH of 6 to 9. In some embodiments, the pH is at or near neutral. Selective lysis of eukaryotic cells at a pH between about 6 to 9 or near neutral is in contrast to current methods, which emphasize alkaline conditions for eukaryotic cell lysis reactions (e.g., at pH 9.5-14). In some embodiments, performing the eukaryotic cell lysis reaction at a pH between about 6 to 9 or near neutral is advantageous over current methods known in the art due to an increase in the viability and/or structural integrity of microbial cells in the presence of some surfactants.

In some embodiments, the methods for eukaryotic cell lysis reactions described herein are advantageous over current methods known in the art because the eukaryotic cell lysis reaction methods described herein are suitable for automation in an integrated device.

Termination of Lysis of Eukaryotic Cells

In some embodiments, the eukaryotic cell lysis reaction is terminated by adding a lysis termination solution that includes at least one electrolyte to the mixture (i.e., the eukaryotic cell lysis solution/sample combination). In some embodiments, the final concentration of the electrolyte in the reaction is between about 25 mM to 850 mM, about 100 mM to 750 mM, about 150 mM to 650 mM, about 200 mM to 550 mM, about 250 mM to 450 mM, or about 300 mM to 400 mM. Electrolytes that can be added to the lysis termination buffer include, but are not limited to, monovalent salts and divalent salts. In some embodiments, the termination of the eukaryotic cell lysis reaction using at least one electrolyte improves downstream processes that use anion-exchange resins (e.g., removal of eukaryotic DNA, isolation of microbial cells, lysis of microbial cells, or isolation of microbial genomic material).

In some embodiments, the electrolyte added to the lysis termination buffer comprises at least one monovalent salt. Monovalent salts include, but are not limited to sodium chloride, potassium chloride, potassium iodide, sodium iodide, lithium chloride, lithium iodide, potassium bromide, sodium fluoride, and potassium fluoride. In some embodiments, the monovalent salt alone is added to the mixture to terminate the lysis reaction. In some embodiments, no termination of the lysis process is required.

In some embodiments, the lysis termination buffer has a pH below about 9. In some embodiments, the pH of the lysis termination buffer is between about 6 and 9. In some embodiments, the lysis termination buffer does not have a pH below 4.0 or above 11.0. In some embodiments, the lysis termination buffer has a pH at about neutral.

In some embodiments, the lysis termination buffer and mixture combination has a pH below about 9. In some embodiments, the lysis termination buffer and mixture combination has a pH between about 6 to 9. In some embodiments, the lysis termination buffer and mixture combination has a pH at about neutral. In some embodiments, maintaining the combination of the lysis termination buffer and mixture at a pH between about 6 to 9 or at about neutral improves downstream processing (e.g., removal of eukaryotic DNA, isolation of microbial cells, lysis of microbial cells, or amplification of microbial DNA) of the intact microbial cells.

Removing Eukaryotic DNA/RNA

In some embodiments, the separation of the eukaryotic genomic material from the intact microbial cells in the mixture or lysis termination buffer and mixture combination is performed through "selective capture" of eukaryotic genomic material or immobilization of the eukaryotic DNA without capturing or immobilization of the intact microbial cells, eukaryotic cellular debris, or other non-nucleic acid material. In some embodiments, the eukaryotic genomic material captured is eukaryotic DNA and/or RNA.

In some embodiments, an anion exchange resin is used to capture/immobilize eukaryotic genomic material. In some embodiments, an anion exchange resin is one or more weak anion-exchange resins (WAX). Examples of WAX include, but are not limited to, carboxymethyl (CM), diethylaminopropyl (ANX), diethylethanolamine (DEAE), Amberlite Ira67, Purolite A847, Amberlite Ira96, Amberlite IRA96SB, Dowex Marathon WBA, Dowex Upcore Mono WB-500, Purolite A835, Dowex Monosphere 77, and Dowex Monosphere 66. In some embodiments, the WAX resin contains at least one tertiary amine functional group.

In some embodiments, an anion exchange resin is one or more strong anion-exchange resins (SAX). Examples of SAX include, but are not limited to, $-O-CH_2-CHOH-CH_2-O-CH_2-CHOH-CH_2-N^+(CH_3)_3$, Amberjet Up4000, Amberjet 9000 OH, Amberlite FPA40 Cl, and Dowex Upcore Mono MA-600. In some embodiments a SAX based resin contains at least one quaternary amine functional group.

In some embodiments, the anion exchange resin is a combination of at least one WAX and at least one SAX.

In some embodiments, the form of the anion exchange resin is selected from fibers, membranes, sorbents, gels, and filter paper. In some embodiments, the sample with the lysed eukaryotic cells is passed through or contacted with the anion exchange resin. In some embodiments, the anion exchange resin is in a solution.

In some embodiments, the anion exchange resin is conjugated to a support substrate. Examples of a support substrate include, but are not limited to, a particle, a bead, a surface, or a sphere. In some embodiments, the support substrate is magnetic, e.g., a magnetic particle or bead. In some embodiments, the anion exchange resin is conjugated to a support substrate is in a solution.

In some embodiments, the support substrate comprises silica, glass, metal, polystyrene-based material, cellulose-based material, agarose-based material, dextran-based material, methacrylate-based material, sepharose-based material, or a combination thereof. In some embodiments the support substrate is porous.

In some embodiments, the support substrate is a bead or sphere has a diameter between about 10 to 100 µm, between about 20 to 90 µm, between about 30 to 80 µm, between about 40 to 70 µm, or between about 50 to 60 µm.

In another embodiment, the support substrate is a bead or sphere have a diameter between about 0.01 to 10 µm, about 0.1 to 9.0 µm, about 1.0 to 8.0 µm, about 2.0 to 7.0 µm, about 3.0 to 6.0 µm, or between about 4.0 to 5.0 µm.

In some embodiments, the mixture is incubated with the anion exchange resin between about 0.1 to 10 minutes, between about 2 to 9 minute, between about 3 to 8 minutes, between about 4 to 7 minutes, or between about 5 to 6 minutes. In some embodiments, the mixture is incubated with the anion exchange resin between about 10 to 30 minutes, between about 12 to 28 minutes, between about 15 to 25 minutes, between about 18 to 23 minutes, or between about 19 to 22 minutes. In some embodiments, the mixture is incubated with the anion exchange resin for less than 1 minute.

In some embodiments, the anion exchange resin is permanently immobilized on the support substrate. In some embodiments, the immobilized anion exchange resin is contacted and/or incubated with the mixture and then the mixture is removed.

In some embodiments, at least one anion exchange resin conjugated to a support substrate, e.g., a bead or a particle, is contacted and/or incubated with the mixture. In some embodiments, after contacting and/or incubation with the mixture, the anion exchange resin conjugated to a support substrate is removed from the mixture. In another embodiment, after contacting and/or incubation with the mixture, the anion exchange resin conjugated to a support substrate is immobilized and the mixture is removed. By way of example, but not by way of limitation, in some embodiments, the anion exchange resin conjugated to a support substrate is selectively immobilized when the support substrate is a magnetized or metal bead and the magnetized or metal bead is exposed to a magnet or magnetic field.

In some embodiments, contacting and/or incubating the mixture with the anion exchange resin extracts eukaryotic DNA, e.g., human DNA (hDNA), and/or RNA from the mixture. In some embodiments, the eukaryotic DNA (and/or RNA) binds to the anion exchange resin. In some embodiments, the anion exchange resin extracts between about 5% to 100%, between about 10% to 99%, between about 15% to 85%, between about 20% to 80%, between about 25% to 75%, between about 30% to 70%, between about 35% to 65%, between about 40% to 60%, or between about 45% to 55% of the eukaryotic DNA (and/or RNA), e.g., hDNA, from the mixture. In some embodiments, the anion exchange resin extracts over 95% of the eukaryotic DNA from the mixture.

Lysis of Microbial Cells

In some embodiments, the mixture (or lysis termination solution and mixture combination) with the eukaryotic DNA removed (hereinafter "isolated microbial cell sample") contains one or more microbial cells. In some embodiments, the isolated microbial cell sample is subjected to further processing. In some embodiments, the isolated microbial cell sample is contacted with a microbial cell lysis solution.

In some embodiments, the microbial cells are lysed using a lysis solution including one or more chemical lysis agents. In some embodiments, the chemical lysis agents include, but are not limited to, cationic detergents, non-ionic detergents, zwitterionic detergents, and enzymes.

In some embodiments, the microbial lysis reaction is performed at a pH between about 6 to 9 or at a neutral pH.

In some embodiments, the microbial lysis solution also includes one or more for the following: enzymes, detergents, and other components such as salts, buffering agents, and metal chelators.

In some embodiments, multiple lysis solutions are used. In some embodiments, the multiple lysis buffers are added in a step wise fashion. In some embodiments, only a single microbial lysis solution is used.

In some embodiments, the microbial lysis reaction is heated to between about 15° C. to 50° C., about 20° C. to 45° C., about 25° C. to 40° C., or about 30° C. to 35° C. In some embodiments, the microbial lysis reaction is performed at room temperature.

In some embodiments, the microbial lysis solution includes one or more of the following enzymes: lysozyme, lyticase, zymolyase, mutanolysin, and lysostaphin. In some embodiments, the one or more enzymes are stored in dry or pelleted form, where upon re-suspension of the respective enzyme, the enzyme reaches the concentrations identified below.

In some embodiments, the lysozyme concentration in the microbial lysis solution is between about 5 to 200 mg/ml, about 1 to 150 mg/ml, 5 to 175 mg/ml, about 15 to 140 mg/ml, about 20 to 100 mg/ml, about 30 to 95 mg/ml, about 45 to 75 mg/ml, about 50 to 62 mg/ml, or between any two of the previously disclosed concentrations.

In some embodiments, the lysozyme concentration in the microbial lysis reaction (e.g., a solution including the microbial lysis solution and the isolated microbial cell sample) is between about 0.01 to 1 mg/ml, about 0.1 to 10 mg/ml, 0.5 to 15 mg/ml, about 1 to 20 mg/ml, about 0.3 to 8 mg/ml, about 0.7 to 7 mg/ml, about 0.2 to 0.9 mg/ml, about 0.05 to 0.35 mg/ml, or between any two of the previously disclosed concentrations In some embodiments, the lyticase concentration in the microbial lysis solution is between about 500 to 50,000 U/ml, about 250 to 10,000 U/ml, 425 to 8,000 U/ml, about 300 to 6,000 U/ml, about 400 to 5,000 U/ml, about 1,000 to 4,750 U/ml, about 1,500 to 4,500 U/ml, about 2,000 to 6,500 U/ml, about 2,500 to 5,500 U/ml, about 3,000 to 15,000 U/ml, or between any two of the previously disclosed concentrations.

In some embodiments, the lyticase concentration in the microbial lysis reaction is between about 1 to 1000 U/ml, about 5 to 200 U/ml, 20 U to 800 U/ml, about 30 to 700 U/ml, about 40 to 600 U/ml, about 50 to 500 U/ml, about 60 to 400 U/ml, about 70 to 300 U/ml, about 80 to 200 U/ml, about 90 to 100 U/ml, or between any two of the previously disclosed concentrations.

In some embodiments, the zymolyase concentration in the microbial lysis solution is between about 500 to 50,000 U/ml, about 250 to 10,000 U/ml, 425 U to 8,000 U/ml, about 300 to 6,000 U/ml, about 400 to 5,000 U/ml, about 1,000 to 4,750 U/ml, about 1,500 to 4,500 U/ml, about 2,000 to 6,500 U/ml, about 2,500 to 5,500 U/ml, about 3,000 to 15,000 U/ml, or between any two of the previously disclosed concentrations.

In some embodiments, the zymolyase concentration in the microbial lysis reaction is between about 1 to 1000 U/ml, about 5 to 200 U/ml, 20 U to 800 U/ml, about 30 to 700 U/ml, about 40 to 600 U/ml, about 50 to 500 U/ml, about 60 to 400 U/ml, about 70 to 300 U/ml, about 80 to 200 U/ml, about 90 to 100 U/ml, or between any two of the previously disclosed concentrations.

In some embodiments, the mutanolysin concentration in the microbial lysis solution is between about 500 to 50,000 U/ml, about 250 to 10,000 U/ml, 425 to 8,000 U/ml, about 300 to 6,000 U/ml, about 400 to 5,000 U/ml, about 1,000 to 4,750 U/ml, about 1,500 to 4,500 U/ml, about 2,000 to 6,500 U/ml, about 2,500 to 5,500 U/ml, about 3,000 to 15,000 U/ml, or between any two of the previously disclosed concentrations.

In some embodiments, the mutanolysin concentration in the microbial lysis reaction is between about 1 to 1000 U/ml, about 5 to 200 U/ml, 20 to 800 U/ml, about 30 to 700 U/ml, about 40 to 600 U/ml, about 50 to 500 U/ml, about 60 to 400 U/ml, about 70 to 300 U/ml, about 80 to 200 U/ml, about 90 to 100 U/ml, or between any two of the previously disclosed concentrations.

In some embodiments, the lysostaphin concentration in the microbial lysis solution is between about 500 to 50,000 U/ml, about 250 to 10,000 U/ml, 425 U to 8,000 U/ml, about 300 to 6,000 Um', about 400 to 5,000 U/ml, about 1,000 to 4,750 U/ml, about 1,500 to 4,500 U/ml, about 2,000 to 6,500 U/ml, about 2,500 to 5,500 U/ml, about 3,000 to 15,000 U/ml, or between any two of the previously disclosed concentrations.

In some embodiments, the lysostaphin concentration in the microbial lysis reaction is between about 1 to 1000 U/ml, about 5 to 200 U/ml, 20 to 800 U/ml, about 30 to 700 U/ml, about 40 to 600 U/ml, about 50 to 500 U/ml, about 60 to 400 U/ml, about 70 to 300 U/ml, about 80 to 200 U/ml, about 90 to 100 U/ml, or between any two of the previously disclosed concentrations.

In some embodiments, one or more salts are added to the microbial lysis solution. In some embodiments the concentration of the monovalents salts is between about 50 mM and 6 M, about 150 mM and 5 M, about 350 mM and 4.5 M, about 550 mM and 4 M, about 900 mM and 3.75 M, about 1 M and 3.5 M, or between any two of the previously disclosed concentrations. In some embodiments, the salt comprises one or more monovalent salts. By way of example, but not by way of limitation, in some embodiments, the monovalent salt is one or more of NaCl, KCl, and/or LiCl.

In some embodiments, the salt concentration in the microbial lysis reaction is between about 50 mM and 800 mM, about 100 mM and 700 mM, about 200 mM and 600 mM, about 300 mM and 500 mM, and about 350 mM and 450 mM, or between any two of the previously disclosed concentrations.

In some embodiments, the one or more monovalents salts is stored in dry or pelleted form, where upon re-suspension of the respective salt, the salt reaches the concentrations identified above.

In some embodiments, an enzymatic reaction time is between about 1-60 minutes, about 5-55 minutes, about 10-45 minutes, about 15-40 minutes, about 20-35 minutes, or about 25-30 minutes.

In some embodiments, DNA contaminants in the enzymatic reaction are removed. In some embodiments, removal of DNA is achieved using ion exchange resins.

In some embodiments, at least one DNA intercalating dye is added to the microbial lysis solution. In some embodiments, the DNA intercalating dyes are dyes that create a covalent bond to both DNA strands after activation with a light source of the appropriate wavelength and dosage. Without wishing to be bound by theory, in some embodiments, the covalent bond renders at least some of the DNA present in the sample unamplifiable. By way of example, but not by way of limitation, in some embodiments, the DNA intercalating dye include, but are not limited to, ethidium monoazide (EMA) and propidium monoazide (PMA).

In some embodiments, the concentration of the DNA intercalating dye in the microbial lysis solution is between about 0.01 µM to 1.0 µM, about 0.1 µM to 0.9 µM, 0.2 µM to 0.8 µM, about 0.3 µM to 0.7 µM, or about 0.4 µM to 0.6 µM, or between any two of the previously disclosed concentrations.

In some embodiments, the microbial lysis solution also includes one or more nucleases. In some embodiments, the nucleases are neutralized prior to usage of the microbial lysis solution. The exact nucleases used depend on the downstream sequences of interest. By way of example, but not by way of limitation, in some embodiments, the nucleases are selected from, but not limited to, EcoRI, HindIII, SalI, HhaI, DdeI, RsaI, Sau3AI and MspI.

In some embodiments, the microbial lysis solution includes one or more detergents. In some embodiments, the detergent is a zwitterionic detergent. In some embodiments, the zwitterionic detergent is from the sulfobetaine families. By way of example, but not by way of limitation, in some embodiments, sulfobetaine detergents include, but are not limited to, N-Decyl-N,N-dimethyl-3-ammonio-1-propanesulfonate, N-Decyl-N,N-dimethyl-3-ammonio-1-propanesulfonate, N-Dodecyl-N,N-dimethyl-3-ammonio-1-propanesulfonate, N-Hexadecyl-N,N-dimethyl-3-ammonio-1-propanesulfonate, N-Octadecyl-N,N-dimethyl-3-ammonio-1-propanesulfonate, and 3-[N,N-Dimethyl(3-myristoylaminopropyl)ammonio]propanesulfonate.

In some embodiments, the detergents are a non-ionic detergent from the glucopyranoside family. By way of example, but not by way of limitation, in some embodiments, non-ionic glucopyranoside detergents include, but are not limited to, 3-acetylumbelliferyl b-D-glucopyranoside, N-amyl b-D-glucopyranoside decyl b-D-thioglucopyranoside, n-dodecyl b-D-glucopyranoside, hexadecyl b-D-glucopyranoside, hexyl b-D-glucopyranoside, methyl a-D-glucopyranoside, octyl b-D-glucopyranoside, and phenyl-a-D-glucopyranoside.

In some embodiments, the detergent is a cationic detergent. By way of example, but not by way of limitation, in some embodiments, cationic detergents include, but are not limited to, alkyltrimethylammonium bromide, hexadecyltrimethylammonium bromide, hexadecylpyridinium bromide, myristyltrimethylammonium bromide, benzyldodecyldimethylammonium bromide, hexadecyl(2-hydroxyethyl)dimethylammonium, hexadecylpyridinium chloride, hexadecyltrimethylammonium chloride, or tetrakis (decyl)ammonium bromide. In some embodiments, the concentration of cationic detergents is between about 1-100× critical micelle concentration (CMC).

In some embodiments, a single detergent from the sulfobetaine and glucopyranoside family is added to the microbial lysis solution. In some embodiments, one or more detergents from the sulfobetaine family and the glucopyranoside family are added to the microbial lysis solution. Additionally, or alternatively, in some embodiments, the microbial lysis solution includes one or more cationic detergents. By way of example, but not by way of limitation, in some embodiments, cationic detergents include alkyltrimethylammonium bromide, amprolium hydrochloride, benzalkonium chloride, benzyldimethyldodecylammonium chloride, benzyldimethyltetradecylammonium chloride, benzyldodecyldimethylammonium bromide, cetylpyridinium chloride, cetyltrimethylammonium bromide, dimethyldioctadecylammonium bromide, dodecylethyldimethylammonium bromide, dodecyltrimethylammonium bromide, ethylhexadecyldimethylammonium bromide, hexadecylpyridinium bromide, hexadecylpyridinium chloride, hexadecyltrimethylammonium bromide, methylbenzethonium chloride, myristyltrimethylammonium bromide, oxyphenonium bromide, tetraheptylammonium bromide, tetrakis(decyl)ammonium bromide, tetrakis(decyl)ammonium bromide, and tricaprylylmethylammonium chloride.

In some embodiments, the concentration of the individual detergent is dependent on the critical micelle concentration (CMC) of the specific detergent in the microbial lysis reaction. In some embodiments, each detergent concentration in the microbial lysis solution is between about 10 to 11,000, about 25 to 12,500, about 50 to 8,000, about 75 to 7,000, about 95 to 8,500, or about 98 to 6,750 times the CMC. In some embodiments, the detergent concentration in the microbial lysis solution is between about 100 to 5,000, about 125 to 9,000, about 200 to 8,000, about 400 to 7,000, or about 500 to 6,000 times the CMC.

In some embodiments, the detergent concentration in the microbial lysis solution is between about 100 to 1000, about 200 to 900, about 300 to 800, about 400 to 700, or about 500 to 600 times the CMC. In some embodiments, each detergent concentration in the microbial lysis reaction is between about 0.1 to 100, about 1.0 to 90, about 10 to 80, about 20 to 70, about 30 to 60, or about 40 to 50 times the CMC.

In some embodiments, the detergents (either as a group or individually, or any combination thereof) are stored in dry or pelleted form, where upon re-suspension of the respective detergent, the detergent reaches the concentrations identified above.

In some embodiments, the microbial lysis solution includes one or more metal chelators. By way of example, but not by way of limitation, in some embodiments, metal chelators include, but are not limited to, ethylene-glycol-tetra acetic acid (EGTA) and ethylenediaminetetraacetic acid (EDTA). In some embodiments, the concentration of the metal chelators in the microbial lysis solution is between about 50 mM to 1.0 M, about 100 mM to 0.75 M, about 110 mM to 500 mM, about 125 mM to 500 mM, about 125 mM to 450 mM, or between any two of the previously disclosed concentrations. In some embodiments, the concentration of the metal chelators in the microbial lysis reaction is between about 5 mM to 250 mM, about 10 mM to 100 mM, about 15 mM to 90 mM, about 20 mM to 80 mM, about 125 mM to 450 mM, or between any two of the previously disclose concentrations.

In some embodiments, the metal chelators are stored in dry or pelleted form, where upon re-suspension of the metal chelators, the metal chelators reach the concentrations identified above.

In some embodiments, the microbial lysis solution includes one or more reducing agents. By way of example, but not by way of limitation, in some embodiments, the reducing agent is 2-mercaptoethanol or dithiothreitol. In some embodiments, the concentration of the reducing agent in the microbial lysis solution is between about 10 mM to 20 M, about 15 mM to 15 M, about 50 mM to 14 M, about 100 mM to 14 M, or about 110 mM to 15 M, or between any two of the previously disclosed concentrations.

In some embodiments, the concentration of the reducing agent in the microbial lysis reaction is between about 1 mM to 100 mM, about 10 mM to 90 mM, about 20 mM to 80 mM, about 30 mM to 70 mM, about 40 mM to 60 mM, or about 45 mM to 55 mM, or between any two of the previously disclosed concentrations.

In some embodiments, the reducing agents are stored in dry or pelleted form, where upon re-suspension of the respective reducing agent, the reducing agent reaches the concentrations identified above.

In some embodiments, the microbial cell lysis reaction is performed at a pH below about 9. In some embodiments, the microbial cell lysis reaction is performed at a pH between about 6 to 9. In some embodiments, the microbial cell lysis reaction is performed at about a neutral pH.

In some embodiments, the microbial cell lysis methods disclosed herein, lead to the release of high molecular weight microbial DNA. Without wishing to be beyond by theory, in some embodiments, the microbial cell lysis methods disclosed herein lead to reduced shearing of microbial genetic materials during the microbial cell lysis and promote the presence of high molecular weight microbial DNA in the lysis solution. In some embodiments, high molecular weight microbial DNA is between about 2 kbp to 200 kbp, about 10 kbp to 190 kbp, about 20 kbp to 180 kbp, about 30 kbp to 170 kbp, about 40 kbp to 160 kbp, about 50 kbp to 150 kbp, about 60 kbp to 140 kbp, about 70 kbp to 130 kbp, about 80 kbp to 120 kbp, or about 90 kbp to 110 kbp.

Isolation of Microbial Genetic Material

In some embodiments, after microbial cell lysis, the microbial genetic material is isolated and/or purified. In some embodiments, the genetic material isolated and/or purified is RNA or DNA. In some embodiments, the DNA is single stranded DNA (ssDNA) or double stranded DNA (dDNA).

In some embodiments, microbial genetic material is isolated by contacting the microbial lysis reaction solution with anion exchange materials packed into columns, wherein the anion exchange material is used for the adsorption and subsequent elution of microbial genetic material. In some embodiments, a solution of known ionic strength and pH enable binding of nucleic acids to the anion exchange column and enable lesser-bound contaminants to be washed away. By way of example, but not by way of limitation, in some embodiments, conditions for selectively binding microbial genetic material with anion exchange materials include contacting the microbial lysis reaction solution with anion exchange in one or more of the following conditions: the contacting reaction is performed at a pH of between about 6 to 9, about 4.5 to 7, or about 8 to 9.5, and the contacting reaction has a monovalent salt concentration of between about 100 mM to 750 mM, about 450 mM to 1.75 M, or about 50 mM to 350 mM. The bound genetic material may then be eluted after contaminants have been removed.

In some embodiments, an anion exchange resin is used to capture/immobilize microbial genomic material. In some embodiments, an anion exchange resin is one or more weak anion-exchange resins (WAX). Examples of WAX include, but are not limited to, carboxymethyl (CM), diethylaminopropyl (ANX), diethylethanolamine (DEAE), Amberlite Ira67, Purolite A847, Amberlite Ira96, Amberlite IRA96SB, Dowex Marathon WBA, Dowex Upcore Mono WB-500, Purolite A835, Dowex Monosphere 77, and Dowex Monosphere 66. In some embodiments, the WAX resin contains a tertiary amine functional group.

In some embodiments, an anion exchange resin is one or more strong anion-exchange resins (SAX). Examples of SAX include, but are not limited to, —O—$CH_2$—CHOH—$CH_2$—O—$CH_2$—CHOH—$CH_2$—$N^+(CH_3)_3$, Amberjet Up4000, Amberjet 9000 OH, Amberlite FPA40 Cl, and Dowex Upcore Mono MA-600. In some embodiments a SAX based resin contains a quaternary amine functional group.

In some embodiments, the anion exchange resin is a combination of WAX and SAX.

In some embodiments, the form of the anion exchange resin is selected from fibers, membranes, sorbents, gels, and filter paper. In some embodiments, the sample with the lysed eukaryotic cells is passed through or contacted with the anion exchange resin. In some embodiments, the anion exchange resin is in a solution.

In some embodiments, the anion exchange resin is conjugated to a support substrate. Examples of a support substrate include, but are not limited to, a particle, a bead, a surface, or a sphere. In some embodiments, the support substrate is magnetic, e.g., a magnetic particle or bead. In some embodiments, the anion exchange resin is conjugated to a support substrate is in a solution.

In some embodiments, the support substrate comprises silica, glass, metal, polystyrene-based material, cellulose-based material, agarose-based material, dextran-based material, methacrylate-based material, sepharose-based material, or a combination thereof. In some embodiments the support substrate is porous.

In some embodiments, the support substrate is a bead or sphere has a diameter between about 10 to 100 μm, between about 20 to 90 μm, between about 30 to 80 μm, between about 40 to 70 μm, or between about 50 to 60 μm.

In another embodiment, the support substrate is a bead or sphere have a diameter between about 0.1 to 10 μm, between about 1.0 to 9.0 μm, between about 2.0 to 8.0 μm, between about 3.0 to 7.0 μm, or between about 4.0 to 6.0 μm.

In some embodiments, the microbial lysis reaction is incubated with the anion exchange resin between about 0.1 to 10 minutes, between about 2 to 9 minute, between about 3 to 8 minutes, between about 4 to 7 minutes, or between about 5 to 6 minutes. In some embodiments, the microbial lysis reaction is incubated with the anion exchange resin between about 10 to 30 minutes, between about 12 to 28 minutes, between about 15 to 25 minutes, between about 18 to 23 minutes, or between about 19 to 22 minutes. In some embodiments, the microbial lysis reaction is incubated with the anion exchange resin for less than 1 minute.

In some embodiments, the microbial lysis reaction is incubated with the anion exchange resin between about 0.01 to 10 minutes, about 0.1 to 9 minutes, 1 to 8 minutes, about 2 to 7 minutes, 3 to 6 minutes, or about 4 to 5 minutes beyond that which is required to lysis the microbial cells.

In some embodiments, the anion exchange resin is permanently immobilized on the support substrate. In some embodiments, the immobilized anion exchange resin is contacted and/or incubated with the mixture and then the mixture is removed.

In some embodiments, at least one anion exchange resin conjugated to a support substrate, e.g., a bead or a particle (e.g., a microparticle), is contacted and/or incubated with the mixture. In some embodiments, after contacting and/or incubation with the microbial lysis reaction, the anion exchange resin conjugated to a support substrate is removed from the microbial lysis reaction. In another embodiment, after contacting and/or incubation with the microbial lysis reaction, the anion exchange resin conjugated to a support substrate is immobilized and the microbial lysis reaction is removed. By way of example, but not by way of limitation, in some embodiments, the anion exchange resin conjugated to a support substrate is selectively immobilized when the support substrate is a magnetized or metal bead and the magnetized or metal bead is exposed to a magnet or magnetic field.

In some embodiments, the beads or particle are packed into a column. In some embodiments, the beads or particle are free floating form.

In some embodiments, the anion-exchange-microparticles is a weak anion exchange material bound to magnetizable microspheres. In some embodiments, the anion-exchange-microparticles is a strong anion exchange material bound to magnetizable microspheres.

In some embodiments, the anion-exchange-microparticles is a weak anion exchange material bound to porous agarose based-microspheres. In some embodiments, the anion-exchange-microparticles is a strong anion exchange material bound to porous agarose based-microspheres.

In some embodiments, after binding the microbial genetic material to the anion-exchange-microparticles, the anion-exchange-microparticles are washed using a wash buffer.

In some embodiments, an salt concentration of the wash buffer is elevated as compared to the salt concentration during binding of the microbial genetic material. In some embodiments, the pH of the wash conditions is altered to achieve more stringent wash conditions. In some embodiment, the pH of the wash buffer is between about 3.0 to 7.5, about 3.5 to 7.0, about 4.0 to 6.5, about 4.5 to 6.0, or about 5.0 to 5.5.

In some embodiments, the wash buffer has a salt concentration between about 0.5 M to 3.0 M, about 0.75 M to 2.75 M, about 1.0 M to 2.5 M, about 1.25 M to 2.25 M, or about 1.5 M to 2.0 M.

In some embodiments, the wash buffer includes one or more surfactants. By way of example, but not by way of limitation, in some embodiments, surfactants include, but are not limited to, Tween and Triton-X. In some embodiments, the Tween and/or Triton-X concentration is between about 0.01% to 1.0% (v/v), about 0.1% to 0.9% (v/v), about 0.2% to 0.8% (v/v), about 0.3% to 0.7% (v/v), or about 0.4% to 0.6% (v/v).

In some embodiments, the wash buffer includes one or more detergents. By way of example, but not by way of limitation, in some embodiments, detergents include, but are not limited to, zwitterionic detergents. In some embodiments, the zwitterionic detergent concentration is between about 0.1× to 350×CMC, about 1.0× to 300×CMC, about 10× to 250×CMC, about 50× to 200×CMC, or about 100× to 150×CMC.

In some embodiments, the methods for isolating the microbial DNA includes an elution step. In some embodiments, competition of the isolation process is facilitated by eluting or removing the DNA off of the anion-exchange-microparticles.

In some embodiments, the pH of the elution buffer is between about 12 to 13.5. The use of an elution buffer with a pH greater than about 12 is not commonly used in the art.

In some embodiments, the elution buffer comprises of a buffering agent such as sodium phosphate or potassium phosphate. In some embodiments, the concentration of sodium phosphate or potassium phosphate is between about 0.01 M to 1 M, about 0.1 M to 1.8 M, about 0.4 M to 1.6 M, about 0.8 M to 1.4 M, or about 1.0 M to 1.2 M. In some embodiments, no buffering agent is required.

Additionally, or alternatively, in some embodiments, the elution buffer comprises sodium hydroxide or potassium hydroxide. In some embodiments, the concentration sodium hydroxide or potassium hydroxide is between about 10 to 500 mM, about 30 to 450 mM, about 50 to 400 mM, about 70 to 350 mM, about 90 to 300 mM, about 110 to 250 mM, or about 130 to 200 mM.

In some embodiments, the elution buffer also includes one or more monovalent salts. By way of example, but not by way of limitation, in some embodiments, monovalent salts include, but are not limited to, NaCl, KCl and LiCl.

In some embodiments, the concentration of the one or more monovalent salts in the elution buffer is between about 0 mM to 200 mM, about 25 mM to 175 mM, about 50 mM, to 150 mM, about 75 mM to 125 mM, or about 90 mM to 110 mM. The use of an elution buffer with monovalent salt concentrations less than about 200 mM is not commonly used in the art. In some embodiments, the elution buffer does not contain any monovalent salts.

In some embodiments, the isolation of microbial genetic material also includes a nucleic acid (e.g., DNA or RNA) purification step. In some embodiments, the purification step includes using chaotropic salts.

In some embodiments, the nucleic acid purification step includes the addition of about 6 M to 9 M of guanidinium chloride or guanidinium thiocyanate. Without wishing to be bound by theory, in some embodiments, the purification allows for efficient binding of a nucleic acid to a silica based solid-phase material such as a filter/membrane, a filter/membrane embedded in a gravity or spin column, or a bead/microsphere/magnetic particle. In some embodiments, subsequent washing of the solid-phase material further removes most of the remaining salts and other hold-over components. In some embodiments, washing is completed using a salt rich, alcohol based buffer. In some embodiments, less than 2 M of guanidinium chloride or guanidinium thiocyanate is added.

In some embodiments, the above isolated microbial genetic material is eluted through the addition of a water-based solution with a pH that is greater than about 5.0. In some embodiments, the isolated microbial genetic material is eluted through the addition of a water-based solution with a pH between about 6 to 9. In some embodiments, the isolated microbial genetic material is eluted through the addition of a water-based solution with a pH that is greater than about 10.

In some embodiments, a size exclusion membrane is used to remove leftover non-nucleic acid contaminants. Membranes for size exclusion filtration include regenerated cellulose (RC), and polyethersulfone (PES) given their hydrophilic nature. Methods and techniques for using these types of membranes are well known and to those skilled in the art and include, but are not limited to, gravity columns, spin columns, vacuum columns, and pressure driven columns. Additionally, these membranes can be incorporated into process specific devices which operate under identical or similar physical principles as those depicts above.

In some embodiments, this nucleic acid purification process is used to desalt the isolated microbial genomic material. In some embodiments, the elution buffer is neutralized with either with an acidic solution (such as HCl) or with a neutral buffer. In some embodiments, no neutralization step is needed.

In some embodiments, no additional purification or desalting is required after eluting the genomic material from the anion-exchange resin Amplification of Microbial Genetic Material In some embodiments, the isolated microbial genetic material is subject to amplification. In some embodiments, the genetic material amplified is RNA or DNA. In some embodiments, the DNA is single stranded DNA (ssDNA) or double stranded DNA (dDNA). In some embodiments, the DNA is ribosomal DNA (rDNA).

In some embodiments, enzymatic amplification can be achieved either through isothermal amplification or thermal-cycling amplification processes.

In some embodiments, polymerase chain reaction, or PCR, is the preferred method of enzymatic amplification which is a well-known method of thermal-cycling based enzymatic amplification In some embodiments, the amplicon is greater than about 400 bp. In some embodiments, the amplicon is between about 400 to 4000 bp, about 700 to 3700 bp, about 1000 to 3400 bp, about 1300 to 3100 bp, about 1600 to 2700 bp, about 1900 to 2400 bp, or about 2100 to 2200 bp. In some embodiments, use of amplicons of the lengths disclosed above are advantageous for downstream processing (e.g., detection and identification of microbial genetic materials) in the methods disclosed herein.

In some embodiments, only bacterial genomic material is amplified. In some embodiments, only fungal genomic material is amplified. In some embodiments, both fungal and bacterial targets are amplified. In some embodiments, synthetic targets are amplified. In some embodiments, synthetic targets include, but are not limited to, plasmids and synthetic genes. By way of example, but not by way of limitation, in some embodiments, plasmids include DNA fragments, such as, e.g., M13mp18, pBR322, pCLIPf, pCLus, pCMV-Cluc, pKLAC2, PMAL-p5x, pNEB206A, pSNAPf, pSV40-CLuc, pTK-GLuc, pTXB1, pTYB21, pUC19, and θX174.

Detection of Microbial Genetic Material and Identification of Microbe

In some embodiments, the microbial DNA is detected and identified.

In some embodiments, DNA Invading Artificial Nucleic Acids (DIANAs) are used detect and identify microbial genetic materials. In some embodiments, the process of invasion, in contrast to hybridization, specifically targets double stranded DNA negating the need to fully denature double stranded DNA (see, e.g., Egholm et al., *Nucleic Acids Res.* 23(2): 217-222 (Jan. 25, 1995).

In some embodiments, the DIANAs take the form of a specialized type or class of Peptide Nucleic Acids (PNAs). In some embodiments, the DIANAs are not limited to a specific class of PNAs. In some embodiments, the DIANAs take the form of a specialized type or class of Locked or Bridged Nucleic Acids (LNAs and/or BNAs). In some embodiments, DIANAs that locally invades duplex DNA has the required affinity and sequence specificity to be used in the methods disclosed herein.

In some embodiments, PNA oligomer based DIANAs have a chiral stereo-center at the gamma-position of the backbone (also known as γPNA). A PNA oligomer that is pre-oriented structurally into a right-handed helix is energetically favored to perform duplex DNA invasion. In some embodiments, the microbial DNA is detected using γPNA as taught in WO 2013/176992, the contents of which are incorporated by reference in its entirety. In some embodiments, use of DIANAs is advantageous for long amplicons (e.g., amplicons between about 400 to 4000 bp).

In some embodiments, the target genomic region of interest in the amplified genetic material includes, but is not limited to, bacterial 16S, ITS, 23S, RPL gene, or TUF gene. Additionally, or alternatively, in some embodiments, the target genomic region of interest in the amplified genetic material includes, but is not limited to, fungal 18S, ITS, 5.8S, and 25/28S. Additionally, or alternatively, in some embodiments, the target genomic region of interest in the amplified genetic material includes antibiotic resistance markers and/or genes.

In some embodiments, each DIANA targets a specific microbial genetic material (e.g., DNA or RNA) from a single microbial species. In some embodiments, each DIANA targets a specific microbial genetic material (e.g., DNA or RNA) a group of microbes. In some embodiments, the specific microbial genetic material (e.g., DNA or RNA) is amplified microbial genetic material.

In some embodiments, the oligomer sequences for DIANAs useful in microbial identification are as follows (Table 1):

TABLE 1

DIANA Probe Sequences

| Group | Target Microorganism | Sequence | SEQ ID NO. |
|---|---|---|---|
| Gram positive | Staphylococcus aureus | TCGAAGAGCAGGCAA | 1 |
| | Staphylococcus epidermidis | TCGAGGTTTACCAATG | 2 |
| | Staphylococcus lugdunensis | TCGAGGTTTACCAATG | 2 |
| | Staphylococcus warneri | GAGGTATTTACCAATG | 3 |
| | Enterococcus faecalis | AAGTCAATGATTGCAGG | 4 |
| | Enterococcus faecium | TTGTCAATGAGAGTAGG | 5 |
| | Streptococcus agalactiae | TACACAATTAATGAGAA | 6 |
| | Streptococcus pyogenes | GCAATCAGAGAGAATA | 7 |
| | Streptococcus mitis | AATTCGTTTACAGTACG | 8 |
| | Streptococcus oralis | AATTCGTTTACAGTACG | 8 |
| | Streptococcus pneumoniae | TCGGATGATACCAATT | 9 |
| Gram Negative | Escherichia coli | GCAGTTACTCGTTTCCATA | 10 |
| | Pseudomonas aeruginosa | CGCGGTGATTCTAGAGT | 11 |
| | | CGCGGTGATACTAGAGT | 12 |
| | Serratia marcescens | AATTCAAGTGGTGGAA | 13 |
| | | AATTCGAGTGGTGGAA | 14 |
| | Acinetobacter baumannii | GGTGATAGAGATCCAT | 15 |
| | Enterobacter aerogenes | CTCGTTCGAGAGACAC | 16 |
| | Enterobacter cloacae | CTCGTTCGAGAGACAC | 16 |
| | Klebsiella oxytoca | CTCGTTCGAGAGACAC | 16 |
| | Klebsiella pneumoniae | CTCGTTCGAGAGACAC | 16 |
| Fungal | Candida albicans | GTATTTACCGATGGG | 17 |
| | Candida glabrata | ACGTAAGGTCATGTGC | 18 |
| | Candida krusei | GATCTAAAAGGTGCC | 19 |
| | Candida tropicalis | TCAGGCTTCTGTAAC | 20 |
| | | AGCGGTTTTCCGATC | 21 |
| | Candida parapsilosis | TGCGTAGTTTTTTCTA | 22 |

TABLE 1 -continued

DIANA Probe Sequences

| Group | Target Microorganism | Sequence | SEQ ID NO. |
|---|---|---|---|
| Pan-Bacterial | Relevant to the majority of bacterial BSIs | CCTGATGGTCCCATAGAT | 23 |
| Pan-Candida | Relevant to the majority of fungal BSIs | CAGGATCTTTGGTTGT | 24 |

In some embodiments, the DIANA probes detect genes conferring antibiotic resistance or markers conferring antibiotic resistance in the microbial genetic material. Genes conferring antibiotic resistance or markers conferring antibiotic resistance include genomic material that confers a reduced susceptibility to either a specific antimicrobial or a class of antimicrobials. By way of example, but not by way of limitation, in some embodiments, a gene conferring antibiotic resistance or markers conferring antibiotic resistance includes, but is not limited to, MecA (which confers a reduction in susceptibility to a number of B-lactam-based antibiotics), VanA/VanB (which confers a reduction in susceptibility to a number of glycopeptide-based antibiotics such as vancomycin), OXA-48, New Delhi Metallo-beta-lactamase-1 (NDM-1), and blakpc (which confers a reduction in susceptibility to common Carbapenems).

In some embodiments, the DIANA probes are used to detect and identify antibiotic resistance microbial cells. Sequences for identification of these nucleic acid biomarkers can be found in Table 2:

TABLE 2

DIANA Probes Sequences for Resistance Identification

| Target | Sequence | SEQ ID NO. |
|---|---|---|
| MecA | GCATTGATAGGAGATC | 25 |
|  | CCAGGGTAATTGAGAC | 26 |
|  | CAGTGTTAGCAACTGC | 27 |
| VanA | GTCCTATCCATTTGCAT | 28 |
|  | CTACTCGGACTTGCGC | 29 |
|  | AAACGACAGTATAACAG | 30 |
| VanB | TCGCAATTCAAGAAGG | 31 |
|  | TTGTCCCATCCATTCG | 32 |
|  | GGTTTCCTGCTTGGAC | 33 |
| VanA/VanB | TGGCTGGAGTGTCGG | 34 |
| OXA-48 | CTGAACCACAAGTAGGA | 35 |
| NDM-1 | ACCAAGCTGTTGCGTAAC | 36 |
| blaKPC | AGTACGGACAACAGTCT | 37 |

In some embodiments, the antibiotic resistance conferring gene or marker is amplified prior to detection. In some embodiments, the amplification of the antibiotic resistance conferring gene or marker is done in a single reaction with the rDNA amplification. In some embodiments, the amplification of the antibiotic resistance conferring gene or marker is done as an addition or external reaction(s).

In some embodiments, the DIANA probes comprise the reverse complementary sequences of any one of SEQ ID NOS: 1-37. In some embodiments, the DIANA probes comprise a sequence with greater than 85% identity with any one of SEQ ID NOS: 1-37 or their reverse complementary counterparts.

In some embodiments, the amplification product is purified. By way of example, but not by way of limitation, in some embodiments, a method for purifying the amplification product includes the reversible binding or absorption of the amplicon onto glass or silica fibers or particles in combination with chaotropic salts followed by their washing and elution. In some embodiments, purification methods include, but is not limited to, precipitation in an alcohol based solutions (e.g., such as ethanol or isopropanol), contacting with anion exchange resins, or size exclusion filters. In some embodiments, the cleaning-up of the amplification product removes excess primers, dNTPs, salts and other components that may interfere with downstream processes.

In some embodiments, no purification process is required, and the amplification product/solution can be used as is.

In some embodiments, the DIANAs are modified to contain a binding moiety. In some embodiments, the binding moiety binds the DIANA to a solid substrate. In some embodiments, the binding DIANA to a solid substrate is useful for separation or washing steps downstream. By way of example, but not by way of limitation, in some embodiments, the binding moieties include, but are not limited to, non-covalent binding moieties (e.g., such as biotin, digoxin, digitoxin) or covalent binding moieties (e.g., COOH group, NHS-ester group, malemide chemistry, and Click chemistry).

In some embodiments, the binding moiety is spaced from the DIANA probe by one or more linkers. In some embodiments, the linker is a single molecule. In some embodiments the linker is comprised of a chain of multiple individual molecules, either linear or branched, that are combined to create a single linker molecule.

In some embodiments, the linker is selected from the group consisting of: (ethylene) glycol, di(ethylene)glycol, tri(ethylene)glycol, poly(ethylene)glycol, carbon linker, amino acids, a silane based linker, or any combination thereof. In some embodiments, the linker serves to distance the DIANA tagged DNA fragment from the surface of the solid phase substrate to which the DIANA is bound to.

In some embodiments, the linker length is between about 20 to 200, about 40 to 180, about 60 to 160, about 80 to 140, or about 100 to 120 atoms. In some embodiments, the linker length is at least 40 atoms. The disclosed linker lengths are not commonly used in the art.

In some embodiments, one or more binding moieties are used along a single linker. In some embodiments, two or more binding moieties along a single linker, wherein each linker has 1 or more binding moieties and wherein each binding moiety is attached to a different location along the oligomer. In some embodiments, multiple binding moieties increase the surface binding kinetics and/or yield and/or efficiently, and/or strength.

In some embodiments, the DNA amplicon is first tagged with one or more DIANAs and then capture the hybrid complex onto the solid-phase surface.

In some embodiments, the DIANA is incubated with a solid surface prior to capturing the microbial genetic material DNA.

In some embodiments, the solid-phase surface is a bead, nanoparticle, microparticle or flat substrate. In some embodiments, the solid-phase surface is further chemically modified to facilitate binding of the DIANA to it.

In some embodiments, capturing a target amplicon and immobilizing it onto the solid-phase surface occurs in individuals wells on system (e.g., a plate or a chip). Exemplary, non-limiting layouts of well on a system are shown in FIGS. 30-36.

In some embodiments, a well is activated with a single DIANA oligomer.

In some embodiments, a well is activated with more than one DIANA probe for a single pathogen; for example the well for *Pseudomonas aeruginosa* (see Table 1)

In some embodiments, one or more probes may be used for multiple pathogens; for example a single well for *Enterobacter aerogenes, Enterobacter cloacae, Klebsiella oxytoca,* and *Klebsiella pneumoniae.*

In some embodiments, the location (well number/position) will yield the information as to which target was captured (e.g., due to the presence of a DIANA probe). In some embodiments, a combination of detected color (e.g., when fluorescence is used as the optical detection modality) and location can be used to decipher which target was captured.

In some embodiments, ssDNA are utilized rather than dsDNA. In some embodiments, ssDNA are created from dsDNA via denaturing protocols or through an asymmetric amplification process prior to DIANA tagging of the DNA molecule.

In some embodiments the DNA is entirely in duplex form. In some embodiments, the DNA is locally in duplex form.

In some embodiments, the invasion solution includes a buffering agent. By way of example, but not by way of limitation, in some embodiments, the buffering agent includes, but is not limited to, tris, sodium-phosphate, and potassium phosphate.

In some embodiments, the concentration of the buffering agent is between about 1 mM to 500 mM, about 50 mM to 450 mM, about 100 mM to 400 mM, about 150 mM to 350 mM, or about 200 mM to 300 mM.

In some embodiments, the invasion solution includes one or more monovalent salts. In some embodiments, the monovalent salt is NaCl or KCl. In some embodiments, the concentration of monovalent salt is between about 1 mM to 150 mM, about 5 mM to 145 mM, about 15 mM to 130 mM, about 25 mM to 115 mM, about 35 mM to 100 mM, about 45 mM to 85 mM, or about 55 mM to 70 mM. In some embodiments, the invasion solution contains no monovalent salts. The disclosed salt concentrations of the invasion assay are below the salt concentration used in standard hybridization assays.

In some embodiments, the invasion solution included one or more surfactants. In some embodiments, the surfactant reduces non-specific binding. By way of example, but not by way of limitation, surfactants include, but are not limited to, Tween-20, or TritonX-100. In some embodiments, the concentration of the surfactant in the invasion solution is between about 0.01% to 1.0% (v/v), about 0.1% to 0.9% (v/v), about 0.2% to 0.8% (v/v), about 0.3% to 0.7% (v/v), or about 0.4% to 0.6% (v/v).

In some embodiments, the invasion solution includes components to vary the excluded volume (e.g., crowding agents). By way of example, but not by way of limitation, crowding agents include, but are not limited to, polyethylene glycol (EG), EG-200, EG-250, EG-300, EG-400, EG-500, EG-750, EG-1,000, EG-9,500, EG-2,000, EG-4,000, EG-5,000, EG-6,000, EG-8,000, EG-10,000, EG-12,000, EG-13,000, EG-20,000, dextrans (DX), polyvinyl-alcohols (PVA), Ficolls (FC), DX-1,000, DX-5,000, DX-12,000, DX-50,000, DX-80,000, PVA 89k-98k, PVA 85k-124k, PVA 130k, PVA 31k-50k, PVA 50k-80k, PVA 70k-100k, PVA 90k-120k, PVA 170k-250k, PVA 61k, PVA 31k, PVA 130k, PVA 67k, PVA 27k, PVA 25k, FC-400, FC-70, FC-40, glycerol, glucose, and sucrose. In some embodiments, the concentration range of the crowding agent in the invasion solution is between about 1% to 20% (v/v), about 3% to 17% (v/v), about 6% to 14% (v/v), or about 9% to 11% (v/v) of the total volume of invasion solution.

In some embodiments, the invasion solution included one or more DNA denaturants. By way of example, but not by way of limitation, DNA denaturants include, but are not limited to, DMSO, formamide, and betaines.

In some embodiments, the invasion solution also includes DMSO, formamide, betaines, or a combination thereof. In some embodiments, the DMSO and/or formamide are between about 1% to 30% (v/v), about 5% to 25% (v/v), about 10% to 20% (v/v), or about 14% to 16% (v/v) of the total volume of invasion solution. In some embodiments, the concentration of the betaines in the invasion buffer is between about 0.1 M and 2.5 M, about 0.5 M and 2.0 M, or about 1.0 M and 1.5 M.

In some embodiments, the invasion solution has a pH of about 10 or more. In some embodiments, an invasion solution with a pH greater than about 10 is conducive to DNA denaturing or destabilization.

In some embodiments, the invasion reaction last between about 0.1 to 5 minutes, about 1 to 10 minutes, about 5 to 30 minutes, or about 10 to 60 minutes.

In some embodiments, the incubation of DIANAs and the microbial genetic material (e.g., amplified microbial DNA) is at a temperature between about 65° C. to 99° C., about 70° C. to 95° C., about 75° C. to 90° C., or about 80° C. to 85° C.

By way of example, but not by way of limitation, in some embodiments, the DIANA invasion process includes DIANA oligomers that have between about 14 to 18 bases, wherein the lower invasion temperature is defined as about: $T_M(DNA)+15°$ C. and the upper invasion temperature is 99° C. $T_M(DNA)$ is defined as the melting temperature of a DNA oligomer with identical composition and sequence to the DIANA oligomer when placed in nearly identical solution conditions (electrolytes strength, buffer, pH, other additives, etc.).

By way of example, but not by way of limitation, in some embodiments, the DIANA invasion process includes using DIANA oligomers that are larger than 18 bases, wherein the lower invasion temperature is defined as about: $T_M(DNA)+0.7°$ C.×(number of bases) and the upper invasion temperature is 99° C.

By way of example, but not by way of limitation, in some embodiments, the DIANA invasion process includes using DIANA oligomers that are smaller/shorter than 14 bases, wherein the lower invasion temperature is defined as about: $T_M(DNA)+1.1°$ C.×(number of bases) and the upper invasion temperature is 99° C.

In some embodiments, the a washing step is performed after DIANA invasion. In some embodiments, the wash step reduces non-specific binding. In some embodiments the wash uses high temperature wash solutions. In some embodiments, the temperature of the wash solution is between about 60° C. and 99° C., about 65° C. and 95° C., about 70° C. and 90° C., or about 75° C. and 85° C.

In some embodiments, the wash buffer comprises one or more of the following: 1) monovalent salt, e.g., as NaCl or KCl, at between about 50 to 650 mM, about 100 to 600 mM, about 150 to 550 mM, about 200 to 500 mM, about 250 to 450 mM, or about 300 to 400 mM; 2) buffered to a near neutral pH, for example between about 6-9; and 3) surfactants, e.g., Tween-20 or Triton X-100 at between about 0.1% to 1.0% (v/v), about 0.2% to 0.9% (v/v), about 0.3% to 0.8% (v/v), about 0.4% to 0.7% (v/v), or about 0.5% to 0.6% (v/v). In some embodiments, the wash buffer is heated.

In some embodiments, the wash buffer includes one or more DNA destabilizing or denaturing agents, e.g., DMSO, betaines, and formamide. In some embodiments, the DMSO and/or formamide are between about 10% to 30% (v/v), about 15% to 25% (v/v), about 10% to 20% (v/v), or about 14% to 16% (v/v) of the total volume of invasion solution. In some embodiments, the concentration of the betaines in the invasion buffer is between about 0.1 M and 2.5 M, about 0.5 M and 2.0 M, or about 1.0 M and 1.5 M.

In some embodiments, the pH of the wash buffer is above 9.0 and includes between about 0 mM to 300 mM, about 50 mM to 250 mM, about 100 mM to 200 mM, or about 125 mM to 175 mM of monovalent salts and/or surfactants. In some embodiments, the pH of the wash buffer is below 6.0 and includes between about 0 mM to 800 mM, about 50 mM to 750 mM, about 100 mM to 700 mM, about 150 mM to 650 mM, or about 200 mM to 600 mM, about 250 mM to 550 mM, about 300 mM to 500 mM, or about 350 mM to 450 mM of monovalent salts and/or surfactants.

By way of example, but not by way of limitation, in some embodiments, the washing step comprises washing DIANA oligomers that are sized between about 14 to 18 bases, wherein the lower wash temperature is defined as about: $T_M(DNA)+20°$ C. and the upper wash temperature is 99° C.

By way of example, but not by way of limitation, in some embodiments, the washing step comprises washing DIANA oligomers that are larger than 18 bases, wherein the lower wash temperature is defined as about: $T_M(DNA)+0.9°$ C.×(number of bases) and the upper wash temperature is 99° C.

By way of example, but not by way of limitation, in some embodiments, the washing step comprises washing DIANA oligomers that are smaller/shorter than 14 bases, wherein the lower wash temperature is defined as about: $T_M(DNA)+1.25°$ C.×(number of bases) and the upper wash temperature is 99° C.

In some embodiments, detection of the binding of DIANAs to their respective target is through optical, chemical, electrical, or mechanical detection methods.

In some embodiments, optical detection is through the use of fluorescence or luminesce.

In some embodiments, one or more detectable markers are positioned on the invading DIANAs. In some embodiments, the one or more detectable markers are positioned on the DNA amplicon captured via the immobilized oligomer. In some embodiments, one or more detectable markers are positioned on a second oligomer, which is universal to some or all potential targets.

By way of example, but not by way of limitation, in some embodiments, the detectable markers include, but are not limited to fluorescent dyes, horseradish peroxidase (HRP), luciferase, methoxycoumarin, dansyl, pyrene, Alexa Fluor 350, AMCA, Marina Blue dye, dapoxyl dye, dialkylaminocoumarin, bimane, hydroxycoumarin, cascade blue dye, Pacific Orange dye, Alexa Fluor 405, Cascade Yellow dye, Pacific Blue dye, PyMPO, Alexa Fluor 430, Fluorescein, Alexa Fluor 488, Oregon Green 488, BODIPY 493/503, Oregon Green 514, Alexa Fluor 514, Alexa Fluor 532, BODIPY TMR, Alexa Fluor 555, Alexa Fluor 546, BODIPY 558/568, Rhodamine Red dye, Alexa Fluor 568, BODIPY 581/591, Alexa Fluor 594, Texas Red dye, Alexa Fluor 610, Alexa Fluor 633, Alexa Fluor 635, Alexa Fluor 647, Alexa Fluor 660, Alexa Fluor 680, Alexa Fluor 700, Alexa Fluor 750, and Alexa Fluor 790.

By way of example, but not by way of limitation, detectable markers enabling indirect detection include, but are not limited to, digoxigenin (DIG), biotin, or dinitrophenyl.

In some embodiments, identification of the microbial species is through DNA amplicon labeling.

In some embodiments, the primers used in the amplification are labeled during with a detectable marker prior to beginning the amplification process.

In some embodiments, modified nucleotides that either contain a tag or are modified to enable the downstream conjugation of tags are used in the amplification process. By way of example, but not by way of limitation, tag-modified nucleotides include, but are not limited to, a nucleotide modified with a diethylaminocoumarin (DEAC), Cyanine 3 (Cy3), Cyanine 5 (Cy5), Fluorescein (FITC), Lissamine, R110, R6G, Tetramethylrhodamine (TAMRA), or Texas Red dye. Example for a modified nucleotides enabling subsequent tagging would be, but are not limited to, a nucleotide modified with an Amino-digoxigenin (DIG), Biotin, or Dinitrophenyl (DNP).

In some embodiments, the labeling of the DNA amplicon is achieved through subsequent incubation with an intercalating dye. By way of example, but not by way of limitation, intercalating dyes include, but are not limited to, PicoGreen, OliGreen, RiboGreen, SYBR Gold, SYBR Green I, SYBR Green II, SYBR Safe, TOTO-1, YOYO-1, YOYO-3, POPO-1, BOBO-1, JOJO-1, POPO-3, LOLO-1, BOBO-3, YOYO-3, TOTO-3, SYTOX-Blue, SYTOX-Green, SYTOX-Orange, SYTOX-Red, and EtBr.

Devices for Automated Removal of Eukaryotic Genomic Material from a Sample

In some aspects, the present technology relates to a device for the automated removal of eukaryotic genomic material from a sample. In some embodiments, the device isolates one or more intact microbial cells from the sample. In some embodiments, the device automates methods for removing eukaryotic DNA and/or isolating one or more microbial cells as described above.

In some embodiments, the devices are fully-automated, wherein no further human intervention is required. In some embodiments, the devices are semi-automated, wherein human intervention is required in order to complete the desired process.

In some embodiments, the devices are stand-alone and do not require dedicated instrumentation. In some embodiments, the devices are operated or powered by one or more instruments.

FIG. 1 shows an exemplary process 100 in a device carrying out an exemplary embodiment of the selective lysis of eukaryotic cells and removal of eukaryotic genomic materials described above. Referring to FIG. 1, in some embodiments, an original sample 101, e.g., a sample from a subject, is combined with a cell lysis solution 102, e.g., an eukaryotic lysis solution to form a mixture. In some embodiments, there is a first reaction 103, e.g., lysis of eukaryotic cells. In some embodiments, a lysis termination solution 104 is added to the mixture to initiate a second reaction 105, e.g., terminating cell lysis. In some embodiments, the mixture is contact with a resin or a resin solution 106, e.g., an anion exchange resin, to initiate a third reaction 107, e.g., capturing DNA. In some embodiments, the captured DNA is eukaryotic DNA, e.g., hDNA. In some embodiments, an output 108 after the third reaction is a DNA depleted solution, e.g., depleted in eukaryotic DNA. In some embodiments, the output comprises a solution containing one or more microbial cells.

In some embodiments, the device is a single-use device, i.e., a disposable device. In some embodiments, the device is in the form of an integrated or functional biochip.

In some embodiments, the device includes a cartridge with the required capacity to process fluid volumes, for example about 0.5 ml to 5 ml, connected to a fluidic device. In some embodiments, the cartridge is a fluidic cartridge.

In some embodiments, the cartridge includes a plurality of chambers. By way of example, but not by way of limitation, in some embodiments, the chambers are used to store a liquid, e.g., a lysis buffer or solution, a lysis termination reagent or solution, a resin solution, used for processing a reaction, e.g., a lysis reaction, used for adding a solution, e.g., the sample, to the device, or a combination thereof. In some embodiments, the chambers of the device also serve to minimize human intervention in the processing of a sample.

By way of example, but not by way of limitation, an exemplary embodiment of the device includes the following chambers: (1) a chamber which accepts the sample in a sufficient volume to enable a reaction process; (2) a chamber containing a lysis solution; (3) a chamber containing a solution which terminates the lysis process; (4) a chamber which contains the resin coupled to particles; and (5) a chamber to which a final solution, e.g., an isolated microbial cell sample, can be transferred.

In some embodiments, the one or more chambers are interconnected connected. Alternatively, or additionally, in some embodiments, the one or more chambers are connected in series. By way of example, but not by way of limitation, in some embodiments, the connections between chambers include, but are not limited to, flow-channels, tubes, pipes, or a combination thereof. In some embodiments, the flow-channels, tubes, and pipes connecting the chambers are disposed on the fluidic device. In some embodiments, the flow-channels, tubes, and pipes connecting the chambers provide multidirectional flow between connected chambers.

In some embodiments, the one or more chambers are connected with one or more flow-gates to control the passage or transfer of fluid from one chamber to another. In some embodiments, the flow-gate has one or more input flow-channels, for the flow of air or fluid, connection with it, and one or more output flow-channels, for the flow of air or fluid connection with it. In some embodiments the flow-gates, input flow-channels, and output flow-channels are disposed on the fluidic device.

In some embodiments, the fluidic device is a chip, biochip, or integrated chip. In some embodiments, the fluidic device includes multiple inputs and outputs. In some embodiments, the fluidic device includes a plurality of venting ports. In some embodiments, the fluidic device includes one or more pneumatic interfaces. In some embodiments, each vent port is connected with its related chamber in the cartridge by tubes, pipes, or flow channels, which are disposed on the fluidic device.

Figure 2A:
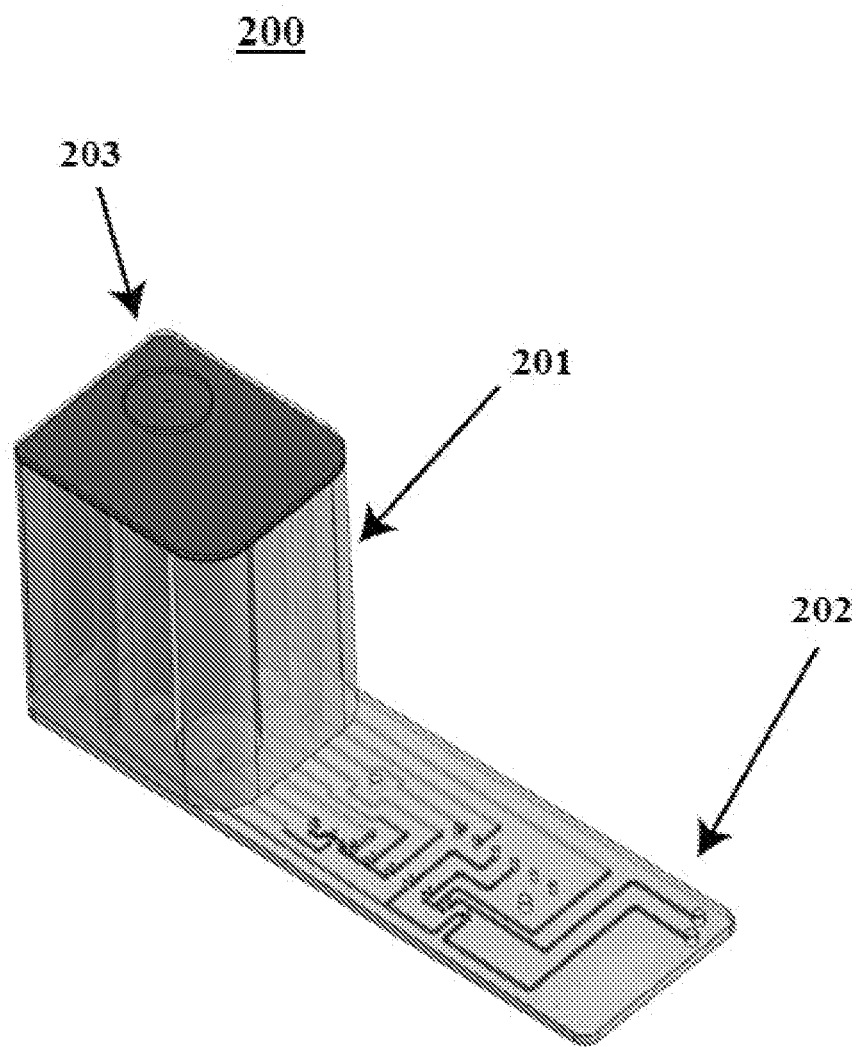
FIG. 2A is an overhead view of an exemplary, non-limiting embodiment of a device for removing eukaryotic DNA from a solution.
Figure 2B:
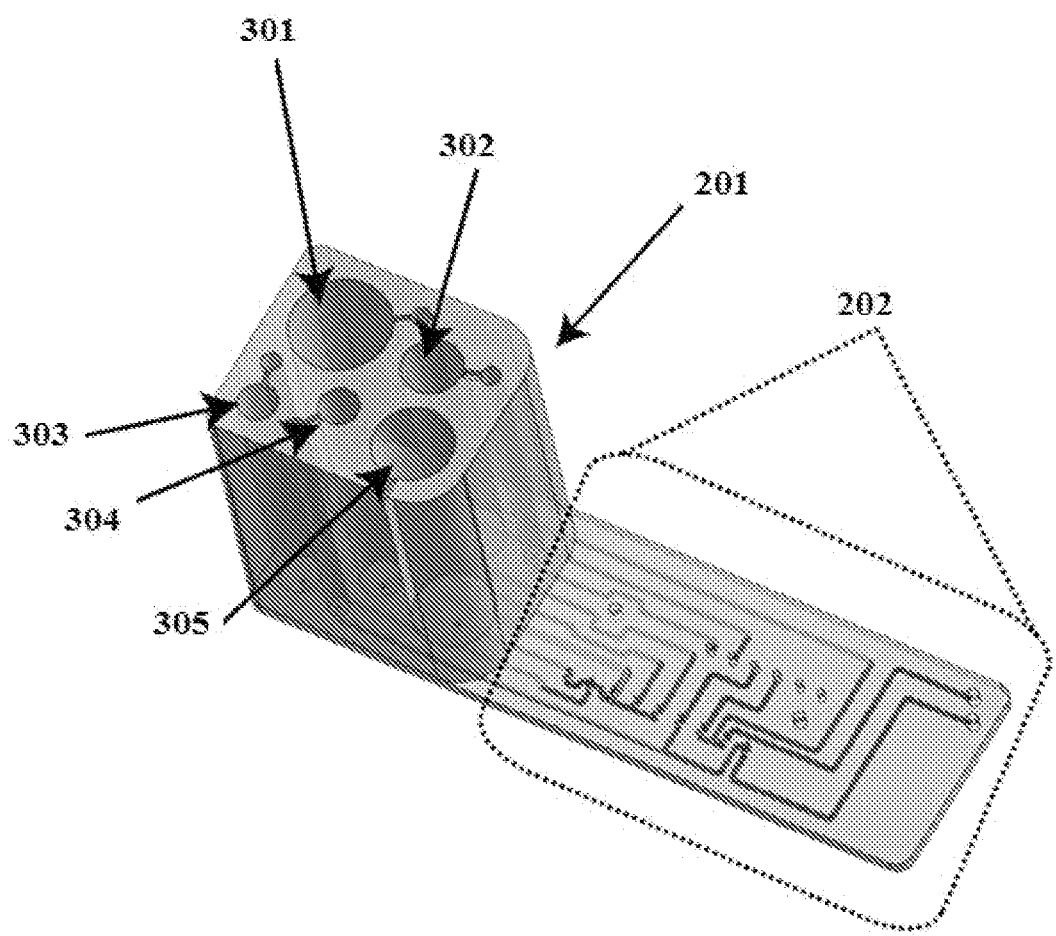
FIG. 2B is an open-overhead view of an exemplary, non-limiting embodiment of a device for removing eukaryotic DNA from a solution.
Figure 2C:
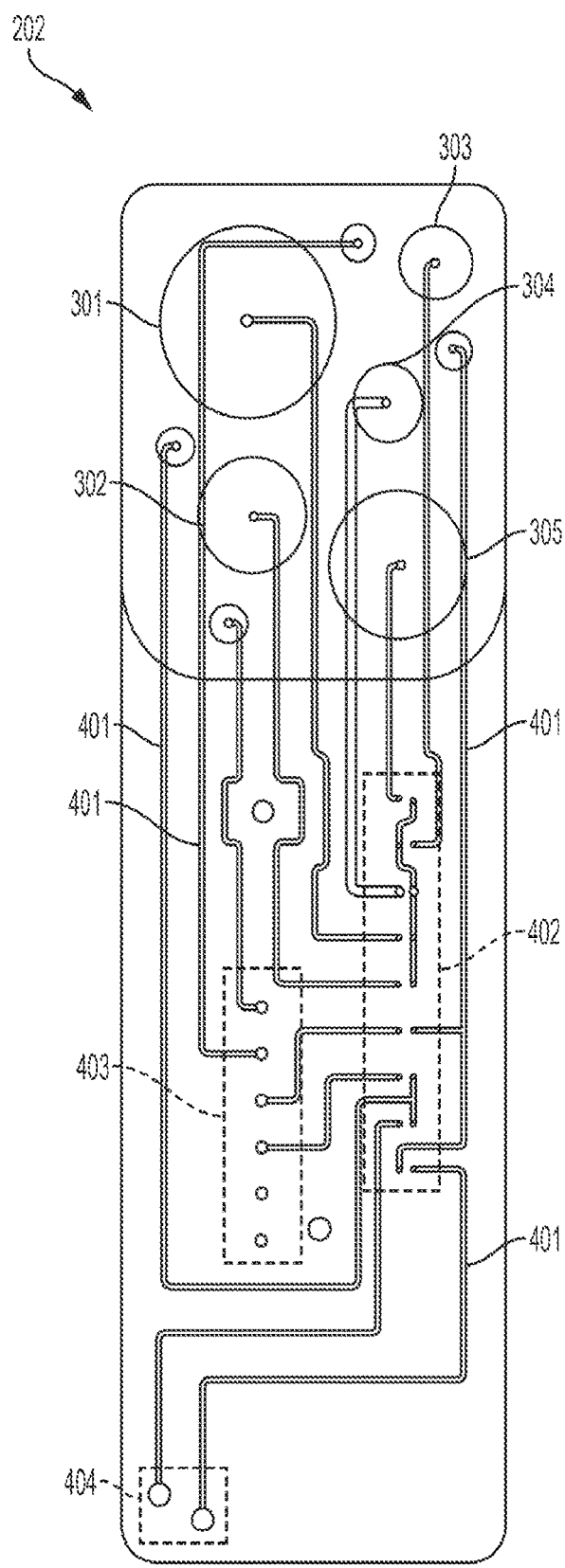
FIG. 2C is a bottom view of an exemplary, non-limiting embodiment of a device for removing eukaryotic DNA from a solution.

FIGS. 2A-C show an exemplary, non-limiting embodiment of a device 200. Referring to FIG. 2A, in some embodiments, the device includes a fluidic cartridge 201 and a fluidic chip 202, wherein the fluidic cartridge 201 is attached to the fluidic chip 202. In some embodiments, there is a sample insert chamber 203. In some embodiments, the fluidic chip 202 and fluidic cartridge 201 are manufactured from the same material. In some embodiments, the fluidic chip 202 and fluidic cartridge 201 are manufactured from different materials. In some embodiments the fluid cartridge 201 may be attached to the fluidic chip 202 through bonding. In some embodiments, the bonding is thermal, chemical, or ultrasonic. In some embodiments the chip/cartridge combination may be manufactured as a single component.

In some embodiments, the device 200 is a standalone device. In another embodiment, the device 200 is an attachment, module, or consumable to a second device or machine. In some embodiments, the second device or machine provides upstream and/or downstream processing steps.

In some embodiments, the fluidic cartridge houses 201 one or more chambers 301-305, see FIG. 2B. By way of example, but not by way of limitation, in some embodiments, the chambers in the fluidic cartridge includes, but are not limited to, a reaction chamber 301, a lysis solution storage chamber 302, a resin storage chamber 303, a lysis termination solution storage chamber 304, and an output chamber 305 for collecting a DNA depleted solution.

Referring to FIG. 2C, by way of example, but not by way of limitation, in some embodiments, the fluidic chip 202 includes, but is not limited to, flow channels 401, flow gates 402, pneumatic interfaces 403, and vents 404. FIG. 2C also depicts an exemplary, non-limiting embodiment for contacting the chambers 301-305 of the fluidic cartridge 201 (see FIG. 2A-B) to the fluidic chip.

In some embodiments, fluid pressure drives the flow of fluid from one chamber to another. In some embodiments, the fluid pressure is induced by a sterile liquid and/or a sterile gas. In some embodiments, the fluid pressure drives the transfer of a fluid between chambers. Alternatively, or additionally, in some embodiments, the fluid pressure prohibits transfer of fluid between chambers.

In some embodiments, one or more solutions in a chamber are mixed or agitated by flowing a sterilized gas into the chamber. In some embodiments, a chamber containing one or more solutions, is subjected to a stream or multiple pulses of sterile air or gas to causing mixing or homogenization of the one or more solutions. Alternatively, or additionally, in some embodiments, one or more solutions in a chamber are mixed or agitated by flowing a sterilized fluid into the chamber.

In some embodiments, the device includes an opening for adding the sample, e.g., injecting the sample into a chamber. In some embodiments, the opening has a re-sealable cover. In some embodiments, opening the cover requires mechanical force, wherein without mechanical force the cover remains closed. In some embodiments, the opening is covered with a membrane through which the sample is injected.

In some embodiments, the sample injection into a chamber is about 1 µl to 50 µl, about 10 µl to 3.0 ml, about 20 µl to 2.5 ml, about 30 µl to 2.0 ml, about 40 µl to 1.5 ml, about 50 µl to 1.0 ml, about 60 µl to 90 µl, about 70 µl to 80 µl, or about 0.5 ml to 10 ml.

In some embodiments, the sample is a bodily fluid, bodily secretion, or a bodily excretion. By way of example, but not by way of limitation, in some embodiments, the sample includes, but is not limited to, stool, sputum, urine, and blood.

In some embodiments, the device contains one or more pneumatic interfaces, wherein sterile air or any sterile gaseous material is used to push and drive fluid from one chamber to another. In some embodiments, the connections between the chambers, e.g., flow-channels, are coupled to a manual, semi-automated, or automated fluid-fluid regulating system.

In some embodiments, a gas or liquid entering the device is sterilized by at least one porous membranes disposed in the device. In some embodiments, the porous membrane is hydrophilic in nature or hydrophobic in nature. In some embodiments, the porous membrane is oleophobic.

In some embodiments, the sterilizing porous membrane has pores between about 0.02 µm to 10 µm, between about 0.05 µm to 4 µm, between about 0.1 µm to 3 µm, or between about 1.0 µm to 2 µm.

In some embodiments, the gas is subjected to UV based decontamination processes.

In some embodiments, the output solution, i.e., the isolated microbial cell sample is processed to identify the microbial species in the sample.

EXAMPLES

The present technology described herein is further illustrated by the following examples. The examples are intended to be illustrative only and are not to be construed as limiting in any way.

Example 1: Lysing Human Cells in Whole Blood

This example shows an exemplary lysis buffer that leads to the extraction of a high percent of eukaryotic DNA.
Method
0.75 ml of human whole-blood was processed by a commercial extraction kit, which used chaotropic salts and alcohol based reagents with silica spin filters to extract human DNA (hDNA). See Scenario 1 of FIG. 3.

0.75 ml of human whole-blood was processed by mixing an equal volume of lysis buffer with the whole-blood and incubating the lysis buffer/whole-blood mixture for 15 minutes. The lysis buffer contained a combination Tween 20 and Triton X-100 with concentrations of about 0.5% (v/v) for each. After incubation, the solution was centrifuged to capture remaining intact cells. After centrifugation, the supernatant containing cellular debris and free hDNA was removed. The pellet was suspended in $H_2O$. After suspension of the pellet in $H_2O$, the solution was process by the commercial extraction kit described above. See Scenario 2 of FIG. 3.

Figure 3:
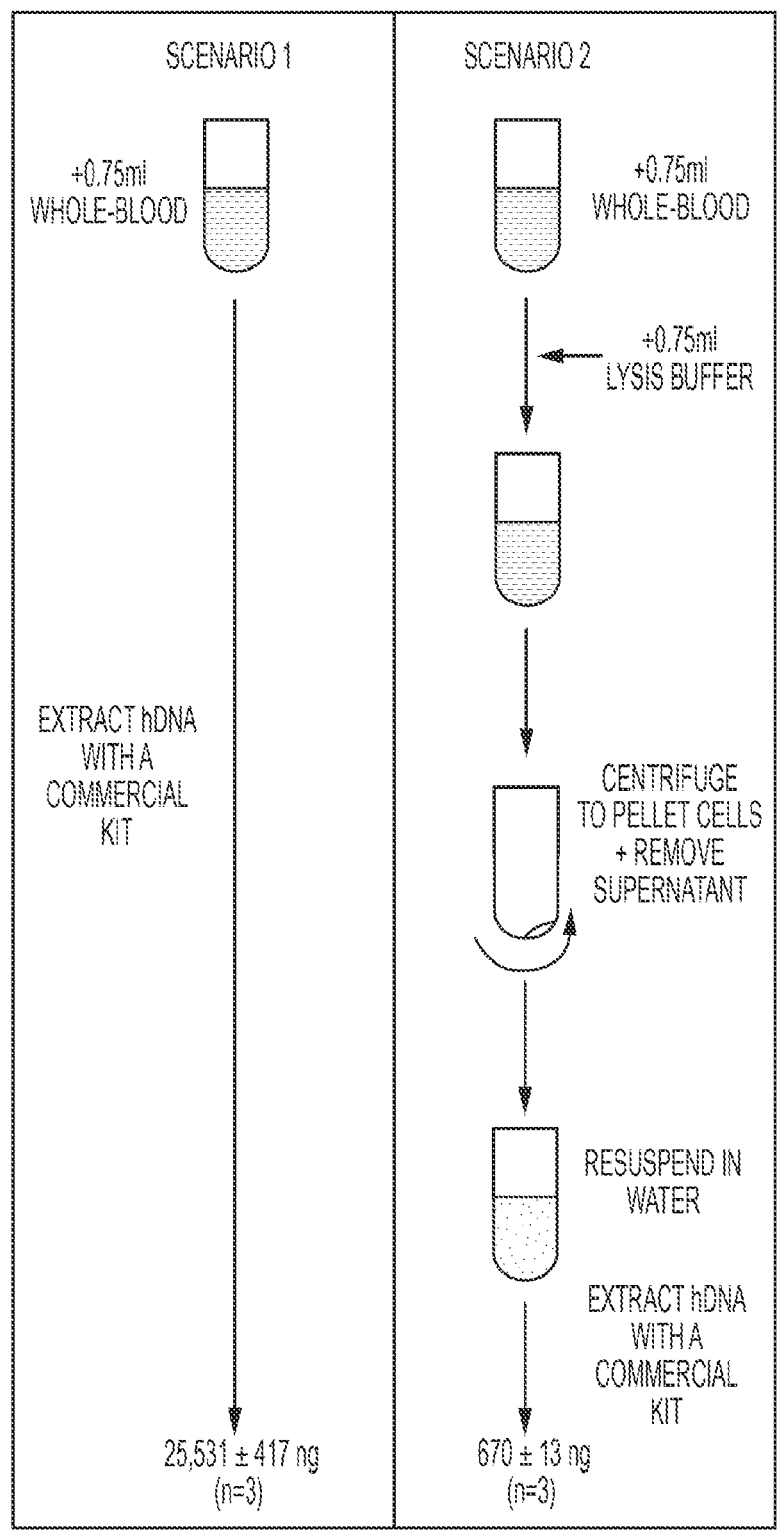
FIG. 3 is a schematic showing an exemplary, non-limiting method for the extraction of human DNA (hDNA) from whole-blood using a lysis buffer.

All processing steps were conducted in triplicate where the results are displayed as Mean±S.dev (see also FIG. 3).
Results
The extraction of hDNA by commercial kit only had hDNA yields, as measured via absorption based assays, at a mass of 25.531±0.417 µg Whole-blood that first underwent hDNA depletion and then commercial extraction had low hDNA yields, as measured via absorption based assays, at a mass of 0.67±0.013 µg.

The results show that about 24.86 µg or 97.5% of the hDNA was extracted using the Tween 20 and Triton X-100 lysis buffer.

These results show that the disclosed lysis buffers are very efficient at targeting eukaryotic cells. As such the lysis buffers disclosed herein are useful for methods and devices for isolating microbial cells and/or removing eukaryotic DNA in a sample.

Example 2: Targeted Lysing of Human Cells in Whole Blood

This example shows that the lysis buffer used in Example 1 does not target bacterial cells.
Methods
Two bacterial species: 1) *S. aureus*, and 2) *E. coli* where treated with the lysis buffer from Example 1, water was used as a control. *S. aureus* is a 'hardy' bacteria as it has an additional 'protective wall' (Gram positive). While *E. coli* is a rather 'weak' (or susceptible) bacteria as it does not have an additional 'protective wall' (Gram negative).

Microbial specimen were cultured overnight using standard media and methods. After culturing, and while still in the log phase, the bacterial culture was serially diluted $10^6\times$ in PBS. All subsequent processing steps were conducted in triplicate where the results indicated in FIG. 4 are displayed as Mean±Std. dev.

Figure 4:
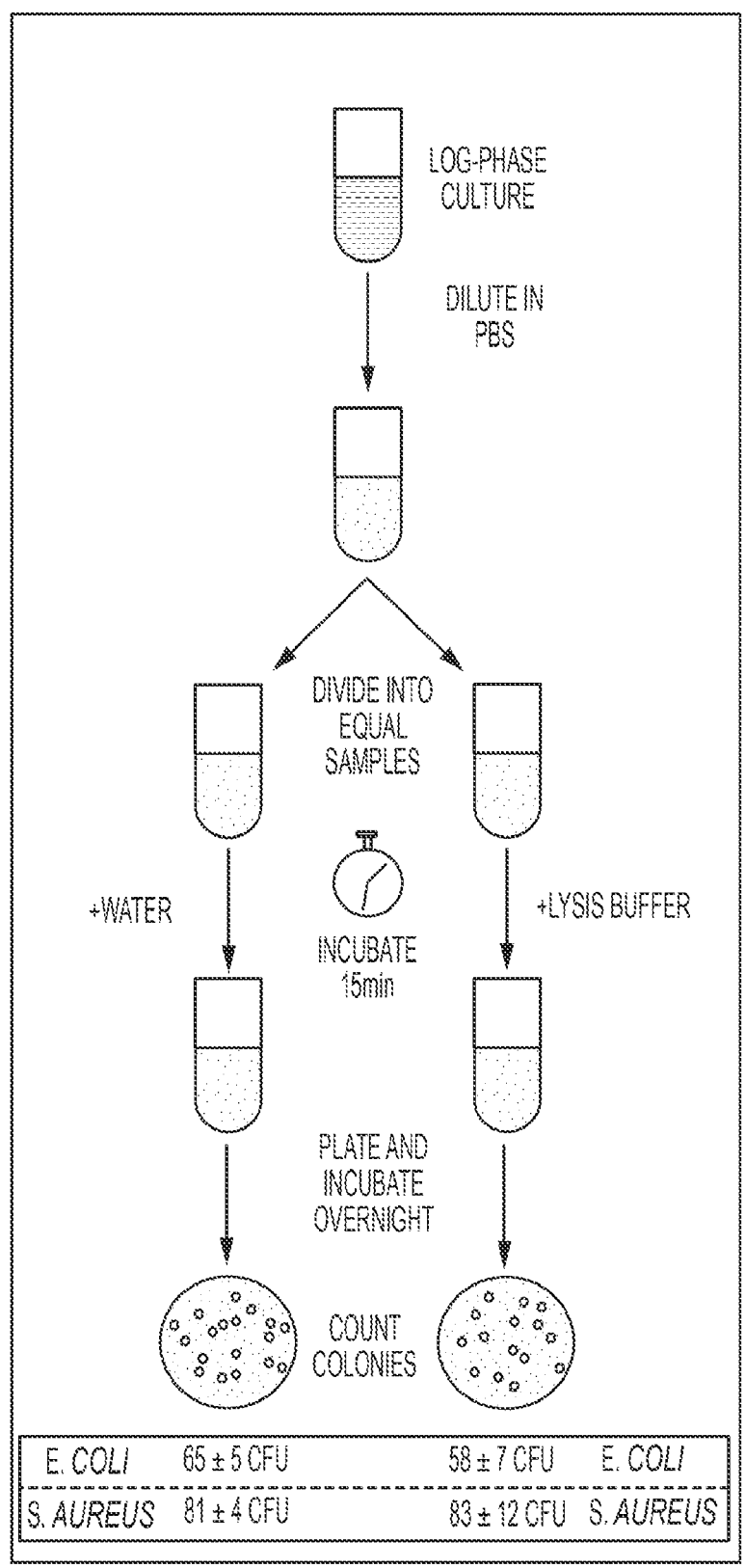
FIG. 4 is a schematic showing an exemplary, non-limiting method that shows that the lysis buffer targets eukaryotic cells.

In assay 1, i.e., the left side of FIG. 4, an equal volume of the sterile $H_2O$ was added to the bacterial dilution and the combined sample was mixed and then incubated for 15 minutes. After incubation, 0.1 ml of the sample was plated onto an agar based media and incubated overnight at 37° C. Post incubation, the number of colonies were counted on each plate.

In assay 2, i.e., the right side of FIG. 4, an equal volume the lysis buffer of Example 1 was added to the bacterial dilution and the combined sample was mixed and then incubated for 15 minutes. After incubation, 0.1 ml of the sample was plated onto an agar based media and incubated overnight at 37° C. Post incubation, the number of colonies were counted on each plate.
Results
The number of colonies from $H_2O$ lysed bacterial cells was *S. aureus:* 81±4 and *E. coli:* 65±5

The number of colonies from lysis buffer lysed bacterial cells was *S. aureus:* 83±12 and *E. coli:* 58±7.

The results show that the lysis buffers disclosed herein do not affect bacterial cells and bacterial cell survival. As such, the lysis buffer disclosed herein target eukaryotic cells, thus the lysis buffers are useful for methods and devices for isolating microbial cells and/or removing eukaryotic DNA in a sample.

Example 3: Removing hDNA from a Whole-Blood

This example show that hDNA was selectively removed from whole-blood using the lysis buffer from Example 1 and anion exchange resin.
Methods
0.1 ml samples of unprocessed human-whole blood were added to an equal volume of lysis buffer described in Example 1 in a first vial. The combined mixture was incubated for 2 minutes at room temperature (about 21° C.). The reaction was terminated with the addition of a lysis terminating solution containing 2M NaCl, with a pH equal to 7.0, likewise at room temperature.

After terminating the lysis process, about 50 µg diethylethanolamine coupled magnetic beads, diameter of about 1 µm, i.e., WAX magnetic beads, were added to the mixture. The WAX magnetic beads and solution were incubated with gentle agitation for 5 minutes at room temperature.

After the incubation period, a rare-earth magnet was introduced outside the vial to immobilize the beads to the wall of the vial. The supernatant was removed from the first vial and placed into a second vial.

The first vial with the beads were washed with water and the captured hDNA was eluted by increasing the electrolyte concentration to 34M NaCl buffered at a near neutral pH The hDNA output was quantified through absorption based assays.

The second vial with the supernatant was subject to a commercial genomic hDNA extraction process. The hDNA output was quantified through absorption based assays.

Figure 5:
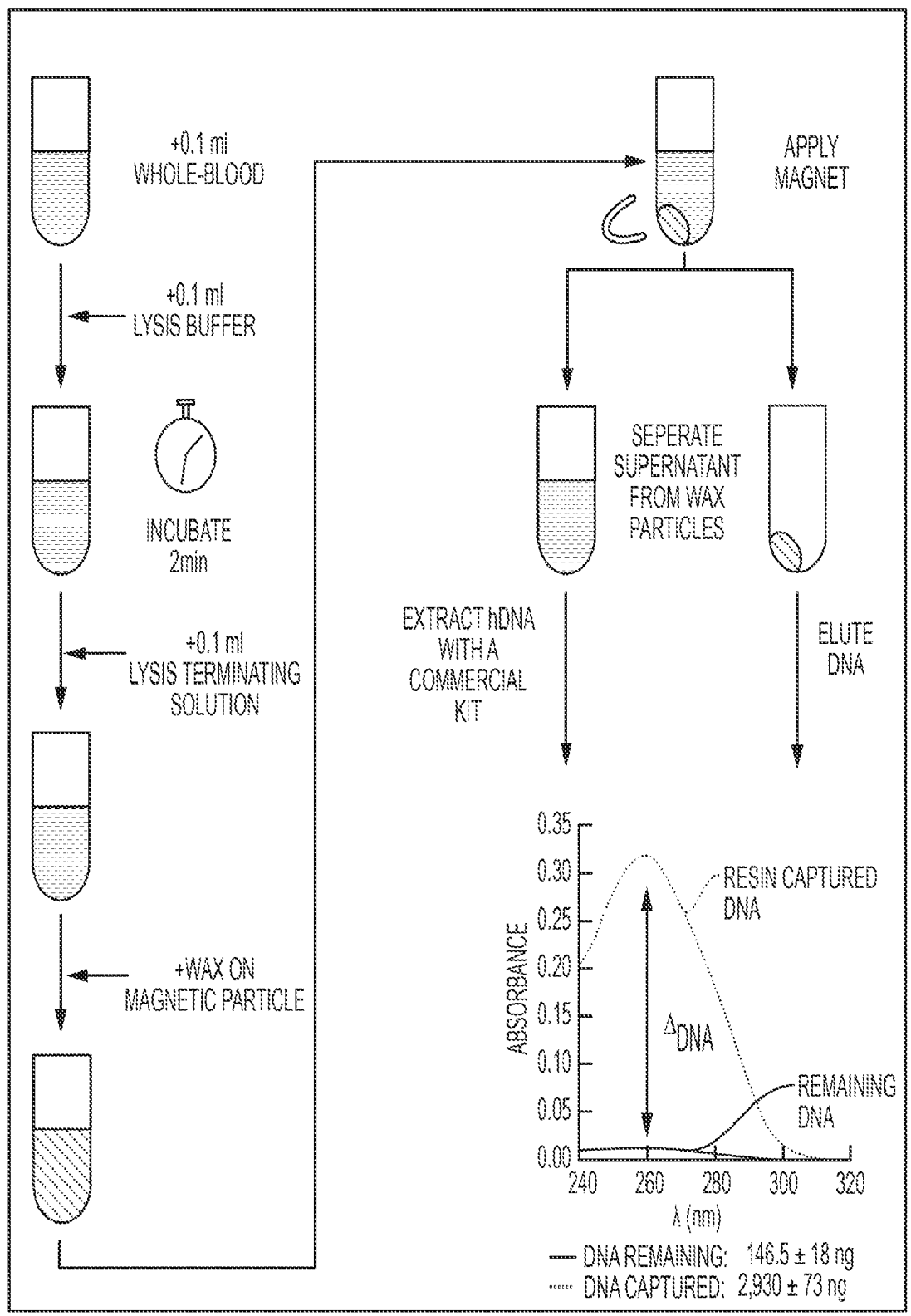
FIG. 5 is a schematic showing an exemplary, non-limiting method for removing eukaryotic DNA from a sample.

All processing steps described above were conducted in triplicate where the results indicated in the FIG. 5 are displayed as Mean±S.dev.

Results

The hDNA output from the first vial was 2,930±73 ng. The hDNA output from the second vial was 146.5±18 ng. The results show that about 95% of the hDNA was removed by the WAX beads.

The results show that anion exchange resins effectively remove hDNA from a solution. As such, using the disclosed lysis buffers to target eukaryotic cell and using anion exchange resins to remove eukaryotic DNA are useful for methods and devices for isolating microbial cells and/or removing eukaryotic DNA in a sample.

Example 4: Comparison of hDNA Extraction by an Automated Process on a Chip to hDNA Extraction by Hand This example shows that hDNA extraction using an automated process on a chip is as effective as hDNA extraction processed by hand, manually, i.e., on the bench top.

Methods

"On-bench" assay: 1.5 ml of human whole blood underwent the same manual processes as described in Example 3. In order to compensate for the increased blood volume, the amount of anion exchange resin was increased 30×, totaling 1.5 mg. Lysis incubation time was increased to 10 minute, and all other reaction steps are identical to those described previously (see FIG. 5). All processing steps were conducted in triplicate where the results indicated in the Table 1 and 2 are displayed as Mean±S.dev.

"On-chip" assay: 1.5 ml of human whole blood underwent the same processes as described in Example 3, however processing was completed in an automated device as described in FIG. 2. In general, all reagents, volumes, processing times, and temperatures were identical to those described in Example 3. 1.5 ml of human whole blood was injected into the reaction chamber (301, FIG. 2C) via a manual process. 1.5 ml of the lysis buffer containing both Tween-20 and Triton X-100 with concentrations of about 0.5% (v/v) each was transferred from the lysis solution storage chamber 302 to the reaction chamber 301 and incubated at room temperature for 2 minutes. Post-incubation, the reaction was terminated with the addition of a lysis terminating solution containing 2M NaCl, with a pH of 7.0, which was originally stored in the lysis termination solution storage chamber 304. After terminating the lysis reaction, 1.5 mg DEAE coated magnetic beads, stored in the resin storage chamber 303 were transferred to the reaction chamber 301. The reaction chamber 301 was agitated mildly through the introduction of sterile air. Mixing occurred for roughly 5 minutes, after which a rare earth magnet was used to immobilize the beads to the wall of the reaction chamber 301. The hDNA depleted sample was then transferred to the output chamber 305. All processing steps were conducted in triplicate where the results indicated in the Table 1 and 2 are displayed as Mean±S.dev.

PCR reaction with eluted hDNA: In both cases, i.e., on-chip and on-bench assays, the hDNA eluted from the WAX was added to a PCR master mix containing 1,000 copies of a simple DNA template. Using standard procedure and employing Kapa Biosystems' HiFi DNA polymerase, PCR reactions were performed.

Results

The "on-bench" assay extracted 96.9±0.3% of the hDNA (see Table 1). The disposable device extracted 97.2±0.4% of the hDNA (see Table 2).

TABLE 1

"On-bench" hDNA Extraction

| Sample | $A_{260}$-Capture | $A_{260}$-Remaining | % Removed |
|---|---|---|---|
| 1 | 0.604 | 0.02 | 96.7 |
| 2 | 0.628 | 0.021 | 96.7 |
| 3 | 0.648 | 0.017 | 97.4 |
| AVG | 0.627 | 0.019 | 96.9 |
| S. dev | 0.018 | 0.002 | 0.3 |

TABLE 2

"On-chip" hDNA Extraction

| Sample | $A_{260}$-Capture | $A_{260}$-Remaining | % Removed |
|---|---|---|---|
| 1 | 0.908 | 0.020 | 97.8 |
| 2 | 0.788 | 0.025 | 96.8 |
| 3 | 0.724 | 0.022 | 97.0 |
| AVG | 0.807 | 0.022 | 97.2 |
| S. dev | 0.076 | 0.002 | 0.4 |

Figure 6:
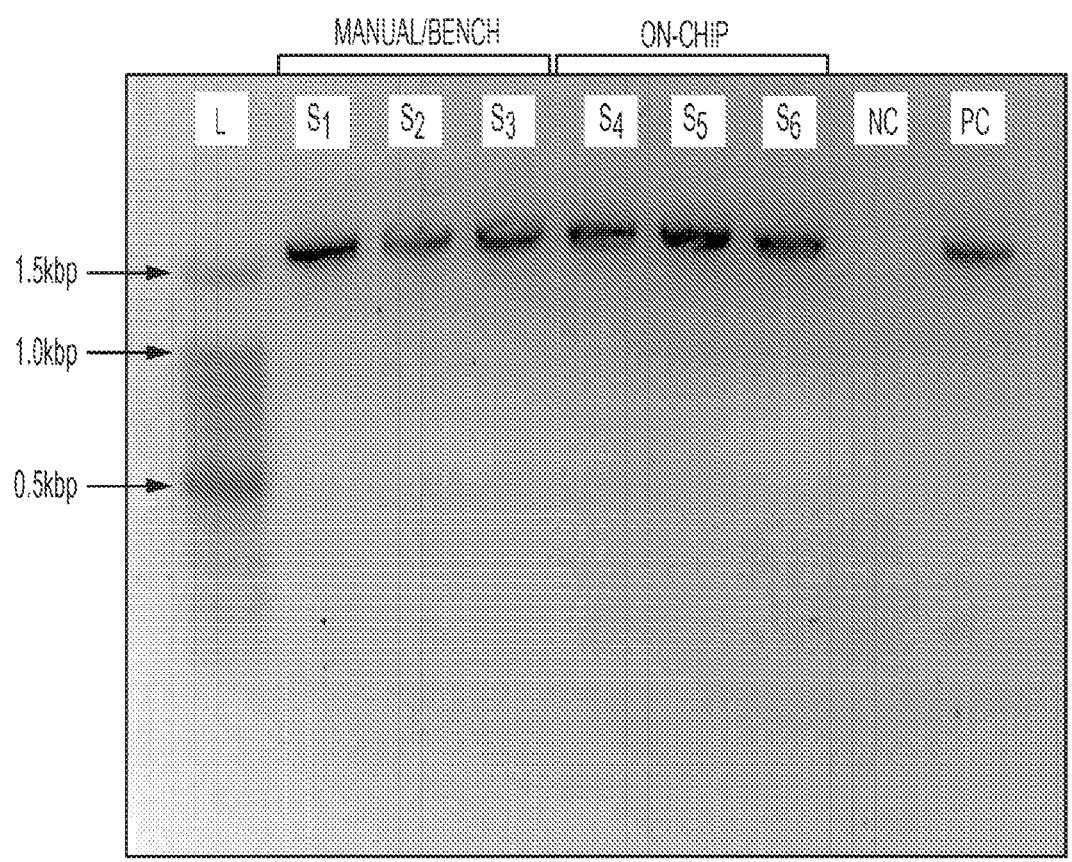
FIG. 6 is a gel that shows that hold over human DNA (hDNA) does not significantly affect the PCR processes for both on-bench and on-chip assays.

The results indicate the ability to complete DNA extraction processes both on-bench and on-chip with equal levels of effectiveness Referring to FIG. 6, lanes 1-3 ($S_1$-$S_3$) are PCR samples that included the hDNA, which was not extracted from the human whole-blood and underwent manual processing and lanes 4-6 ($S_4$-$S_6$) are PCR samples that included the hDNA, which was not extracted from the human whole-blood and underwent the automated processing. NC depicts a sham experiment, and PC indicates the PCR product output (1.5 kbp) from a $10^3$ copy template without the presence of hDNA.

FIG. 6 shows that the left over or hold over hDNA does not significantly affect downstream processes from a sensitivity perspective as the PCR process for both on-bench and on-chip were not hindered.

The results show that an equal level of DNA product from both on-bench and on-chip processing, which also do not significantly differ from the positive control.

Example 5: Detection of S. aureus

This example shows the detection of S. aureus directly from human whole blood using the methods disclosed herein at two clinically relevant load levels: 10-100 CFU/ml ('high-load') and 1-10 CFU/ml ('low-load'). The loads specifically were 41 CFU/ml and 4 CFU/ml.

Methods: Fresh human whole-blood drawn into a EDTA vacuette was inoculated with S. aureus (ATCC #43300) at either a 'high-load' or a 'low-load'. 1.5 ml of contrived human blood was extracted and placed into a fresh vial. To the 1.5 ml blood sample, 1.5 ml of a lysis solution comprising of Tween-20 at 2% (v/v) and Triton-X100 at 1.3% (v/v) was added. After about 5 minutes, NaCl was added to the combined mixture to a final concentration of 150-300 mM and WAX conjugated magnetic particles were added. After about 2 minutes, a rare earth magnet was used to immobilize the magnetic particles to the surface of the vial and about 3 ml of solution was removed and placed into a fresh vial.

A microbial lysis solution was added to the fresh vial. The microbial lysis solution contained the following: cross-linked and affinity purified lysozyme (2-13 mg), mutanolysin (10-350 U), zymolyase (18-200 U), and lysostaphin (65-250 U) in addition to a detergent based reagent containing a glucopyranoside, a cationic detergent, and a sulfobetaine (all of which were at concentrations above their individual CMCs (>10x)). The microbial lysis reaction also included EDTA (at about 10 mM) and 2-Mercaptoethanol (at about 25 mM). The combined reaction mixture was incubated for about 10 to 15 minutes after which WAX conjugated magnetic particles were added to the solution. After about 2 minutes, a rare earth magnet was used to immobilize the magnetic particles to the surface of the vial and the microbial lysis solution was removed and discarded.

The beads were washed repeatedly with a buffered wash solution containing 1 M NaCl. The microbial DNA was eluted off of the beads with an elution reagent buffered to pH 12.5. The elution solution was ultra-filtered. Post-ultrafiltration, the microbial DNA was subject to PCR of the full length rDNA with the following primer sequences (5'-3'):

```
                                          (SEQ ID NO: 38)
CCC CCC CCT CAG TTA TCG TTT ATT TGA TAG TAC C;

(SEQ ID NO: 39)
CCC CCC CCT CAG TTA TCG TTT ATT TGA TAG TTC C;

(SEQ ID NO: 40)
CCC TTC CCA GAG TTT GAT CAT GGC TCA G;

(SEQ ID NO: 41)
CCC TTC CAG AGT TTG ATC CTG GCT CAG;

(SEQ ID NO: 42)
CCC CCC GGT TAC CTT GTT ACG ACT T;

(SEQ ID NO: 43)
CCC CCGG CTA CCT TGT TAC GACT T;

(SEQ ID NO: 44)
CCC TTC CCT GAT GAC TCG TGC CTA CTA;

(SEQ ID NO: 45)
CCC TCT CCC TGA TGA CTT GCG CTT ACT A
```

Each primer contains a hapten moiety for subsequent labelling. Post-PCR, the sample was divided equally into 17 chambers, each loaded with biotinylated gamma-modified PNA probes with sequences identified in Table 1 and an invasion supporting reagent containing Tween-20, NaCl, and poly-EG-12,000. Each well was heated to 70-95° C. for 1-5 minutes with the addition of 5 ml of stock MyOne Cl Streptavidin coated beads. Post-immobilization of γPNA probes onto the beads, the beads were washed in a solution containing between 150-550 mM NaCl at a temperature at least 75-95° C. Post washing, to each chamber a solution containing a HRP-conjugate targeting the primer-hapten was added, which binds to the free hapten (if present) on the captured amplicon. After a number of wash steps with a neutral low salt wash, luminol was added to create a distinct optical signature only where the microbial DNA was captured. The optical signatures were read using a Promega GloMax plate reader with an integration time of 2.5 sec/well. Each reaction was completed in triplicate.

Figure 7:
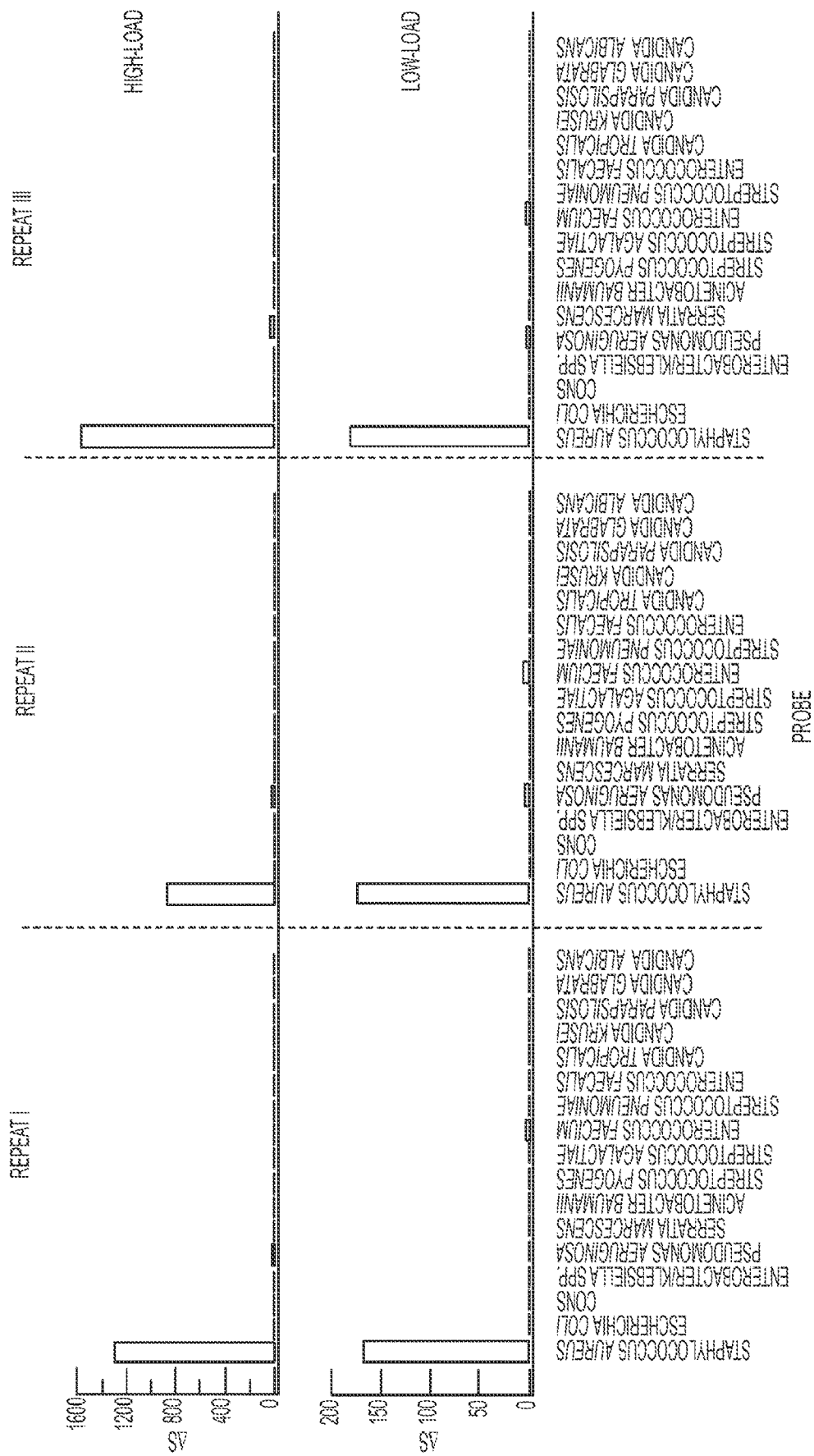
FIG. 7 is a chart showing the detection of *S. aureus* in human blood samples, wherein *S. aureus* was inoculated in the blood samples at high loads and low loads.

Results: A clearly identifiable optical signature was only seen in the S. aureus channel (which came from the chamber activated with a gamma-modified PNA probe specific to S. aureus). See FIG. 7.

These results show that the compositions and methods disclosed herein can identify at least one specific pathogen from a sample blood. Accordingly, the compositions and methods disclosed herein are useful for the detection and identification of microbes in a sample.

Example 6: Detection of S. epidermidis

This example shows the detection of S. epidermidis directly from human whole blood using the methods disclosed herein at two clinically relevant load levels: 10-100 CFU/ml ('high-load'), and 1-10 CFU/ml ('low-load'). The loads specifically were 47 CFU/ml and 5 CFU/ml.

Methods: Fresh human whole-blood drawn into a EDTA vacuette was inoculated with S. epidermidis (ATCC #51625) at either a 'high-load' or a 'low-load'. The method disclosed in Example 5 to detect microbial DNA was used.

Figure 8:
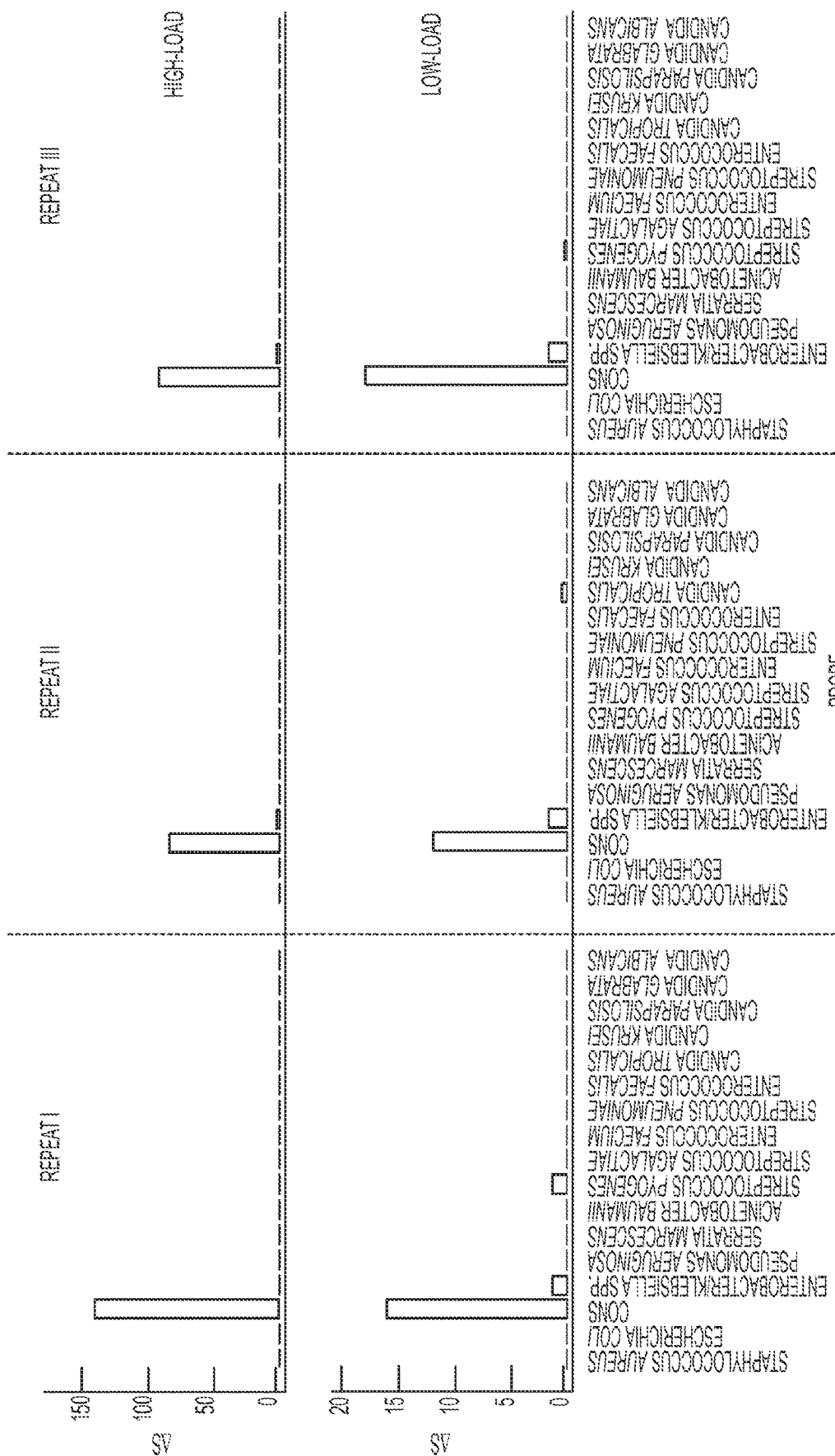
FIG. 8 is a chart showing the detection of *S. epidermidis* in human blood samples, wherein *S. epidermidis* was inoculated in the blood samples at high loads and low loads.

Results: A strong optical signature was seen in the CoNS channel (which came from the chamber activated with a gamma-modified PNA probe specific to CoNS). See FIG. 8.

These results show that the compositions and methods disclosed herein can identify at least one specific pathogen from a sample blood. Accordingly, the compositions and methods disclosed herein are useful for the detection and identification of microbes in a sample.

Example 7: Detection of S. lugdunensis

This example shows the detection of S. lugdunensis directly from human whole blood using the methods disclosed herein at two clinically relevant load levels: 10-100 CFU/ml ('high-load'), and 1-10 CFU/ml ('low-load'). The loads specifically were 51 CFU/ml and 5 CFU/ml.

Methods: Fresh human whole-blood drawn into a EDTA vacuette was inoculated with S. lugdunensis (ATCC #49576) at either a 'high-load' or a 'low-load'. The method disclosed in Example 5 to detect microbial DNA was used.

Figure 9:
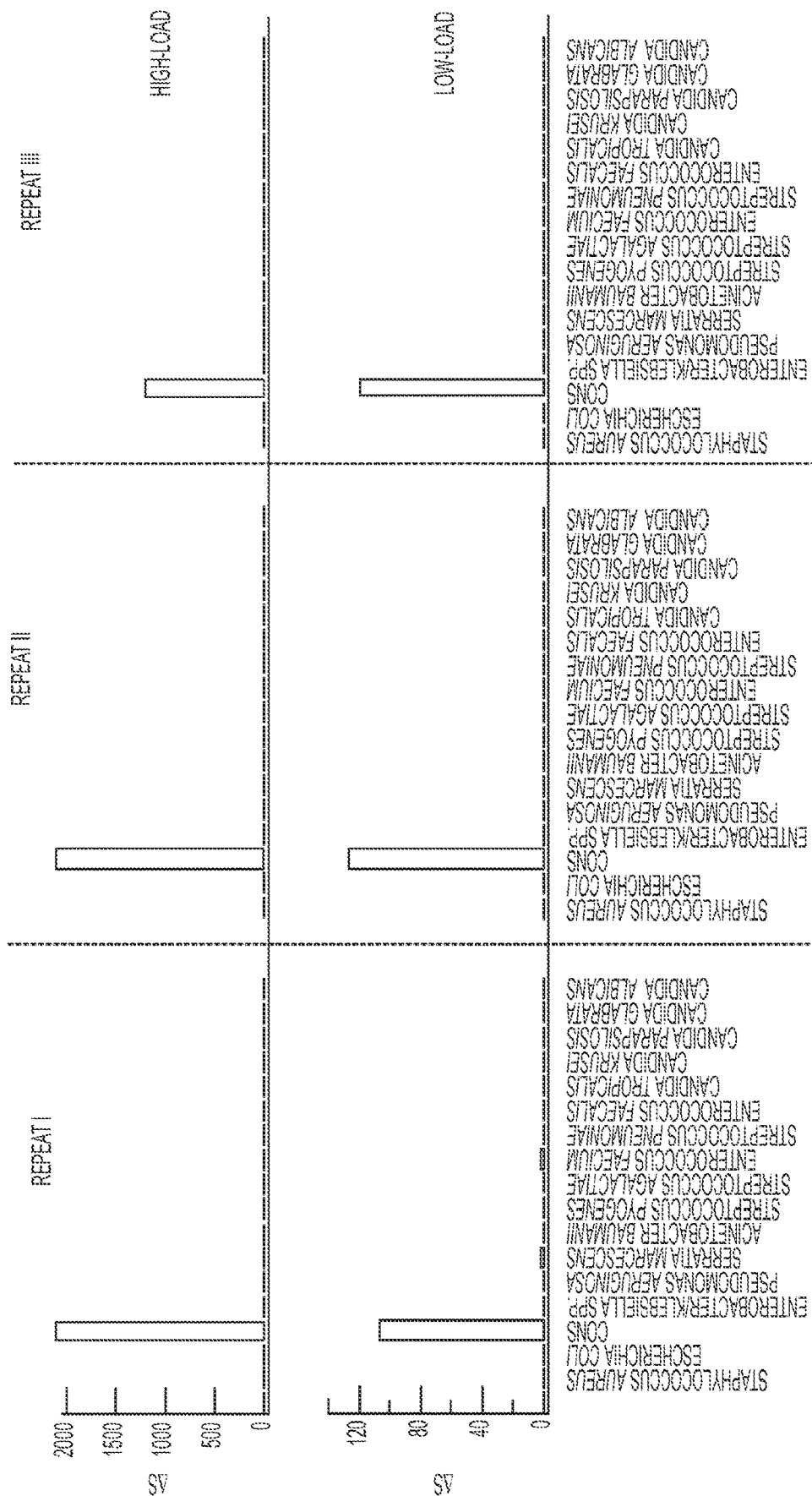
FIG. 9 is a chart showing the detection of *S. lugdunensis* in human blood samples, wherein *S. lugdunensis* was inoculated in the blood samples at high loads and low loads.

Results: A clearly identifiable optical signature was seen only in the CoNS channel (which came from the chamber activated with a gamma-modified PNA probe specific to CoNS). See FIG. 9.

These results show that the compositions and methods disclosed herein can identify at least one specific pathogen from a sample blood. Accordingly, the compositions and methods disclosed herein are useful for the detection and identification of microbes in a sample.

Example 8: Detection of S. agalactiae

This example shows the detection of S. agalactiae directly from human whole blood using the methods disclosed herein at two clinically relevant load levels: 10-100 CFU/ml ('high-load'), and 1-10 CFU/ml ('low-load'). The loads specifically were 20 CFU/ml and 2 CFU/ml.

Methods: Fresh human whole-blood drawn into a EDTA vacuette was inoculated with S. agalactiae (ATCC #13813) at either a 'high-load' or a 'low-load'. The method disclosed in Example 5 to detect microbial DNA was used.

Figure 10:
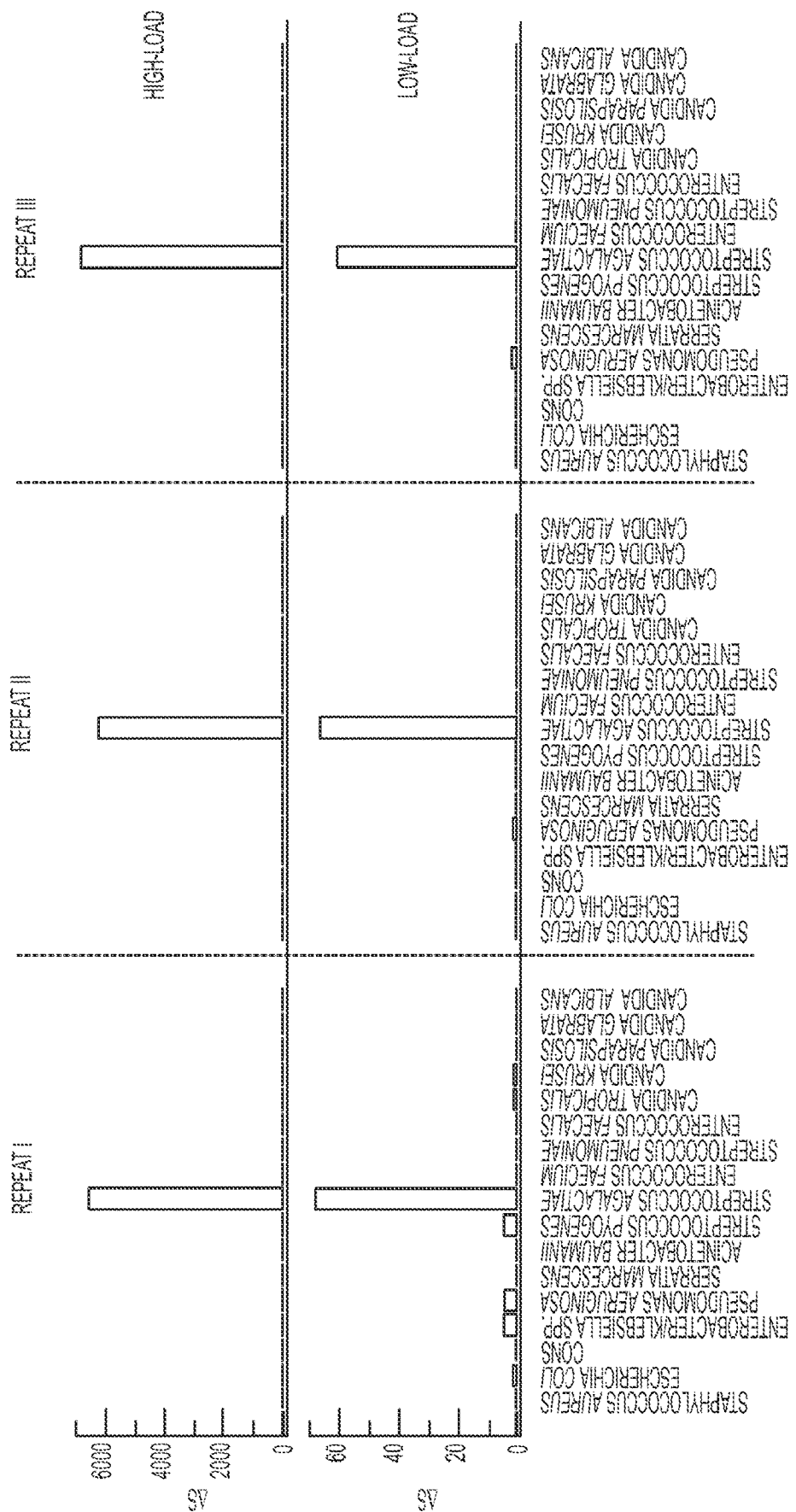
FIG. 10 is a chart showing the detection of *S. agalactiae* in human blood samples, wherein of *S. agalactiae* was inoculated in the blood samples at high loads and low loads.

Results: A clearly identifiable optical signature was only seen in the S. agalactiae channel (which came from the chamber activated with a gamma-modified PNA probe specific to S. agalactiae). See FIG. 10.

These results show that the compositions and methods disclosed herein can identify at least one specific pathogen from a sample blood. Accordingly, the compositions and methods disclosed herein are useful for the detection and identification of microbes in a sample.

Example 9: Detection of S. pneumoniae

This example shows the detection of S. pneumonia directly from human whole blood using the methods disclosed herein at two clinically relevant load levels: 10-100 CFU/ml ('high-load'), and 1-10 CFU/ml ('low-load'). The loads specifically were 75 CFU/ml and 7 CFU/ml.

Methods: Fresh human whole-blood drawn into a EDTA vacuette was inoculated with S. pneumoniae (ATCC #6303) at either a 'high-load' or a 'low-load'. The method disclosed in Example 5 to detect microbial DNA was used.

Figure 11:
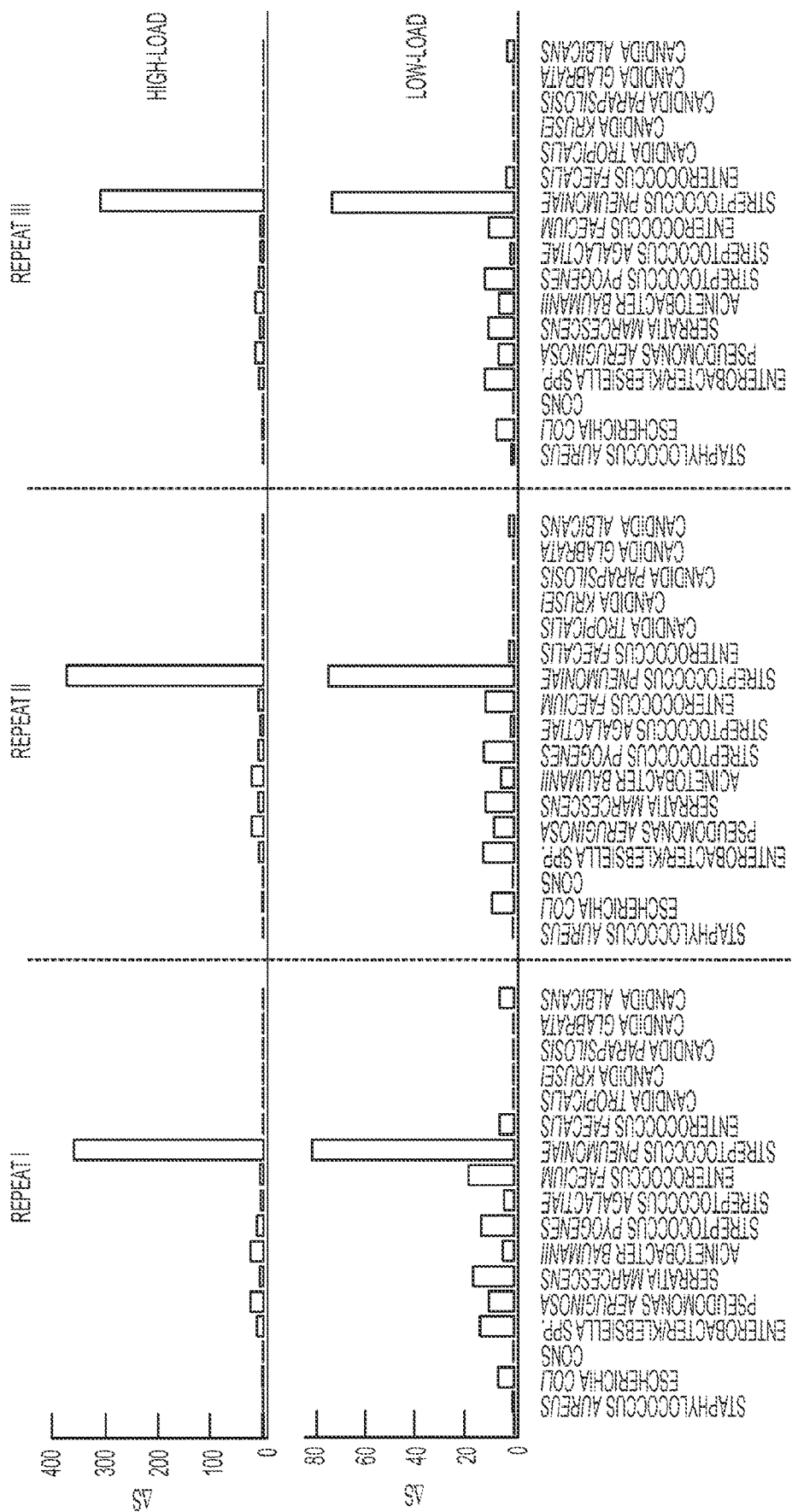
FIG. 11 is a chart showing the detection of *S. pneumoniae* in human blood samples, wherein *S. pneumoniae* was inoculated in the blood samples at high loads and low loads.

Results: A strong optical signature was seen in the S. pneumonia channel (which came from the chamber activated with a gamma-modified PNA probe specific to S. pneumoniae). See FIG. 11.

These results show that the compositions and methods disclosed herein can identify at least one specific pathogen from a sample blood. Accordingly, the compositions and methods disclosed herein are useful for the detection and identification of microbes in a sample.

Example 10: Detection of S. pyogenes

This example shows the detection of S. pyogenes directly from human whole blood using the methods disclosed herein at two clinically relevant load levels: 10-100 CFU/ml ('high-load'), and 1-10 CFU/ml ('low-load'). The loads specifically were 17 CFU/ml and 2 CFU/ml.

Methods: Fresh human whole-blood drawn into a EDTA vacuette was inoculated with S. pyogenes (ATCC #12344) at either a 'high-load' or a 'low-load'. The method disclosed in Example 5 to detect microbial DNA was used.

Figure 12:
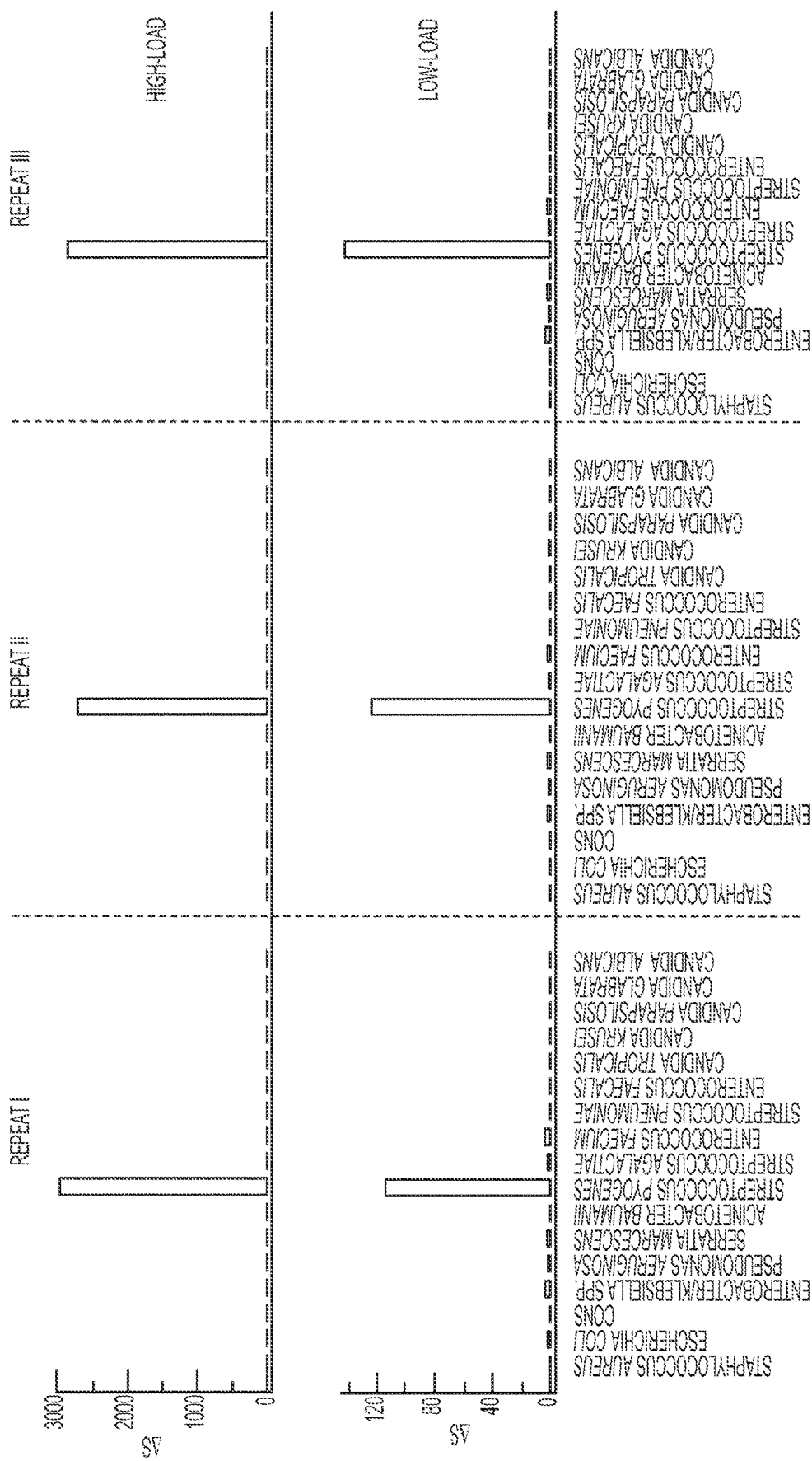
FIG. 12 is a chart showing the detection of *S. pyogenes* in human blood samples, wherein *S. pyogenes* was inoculated in the blood samples at high loads and low loads.

Results: A clearly identifiable optical signature was only seen in the S. pyogenes channel (which came from the chamber activated with a gamma-modified PNA probe specific to S. pyogenes). See FIG. 12.

These results show that the compositions and methods disclosed herein can identify at least one specific pathogen from a sample blood. Accordingly, the compositions and methods disclosed herein are useful for the detection and identification of microbes in a sample.

Example 11: Detection of E. faecalis

This example shows the detection of E. faecalis directly from human whole blood using the methods disclosed herein at two clinically relevant load levels: 10-100 CFU/ml ('high-load'), and 1-10 CFU/ml ('low-load'). The loads specifically were 54 CFU/ml and 5 CFU/ml.

Methods: Fresh human whole-blood drawn into a EDTA vacuette was inoculated with E. faecalis (ATCC #29212) at either a 'high-load' or a 'low-load'. The method disclosed in Example 5 to detect microbial DNA was used.

Figure 13:
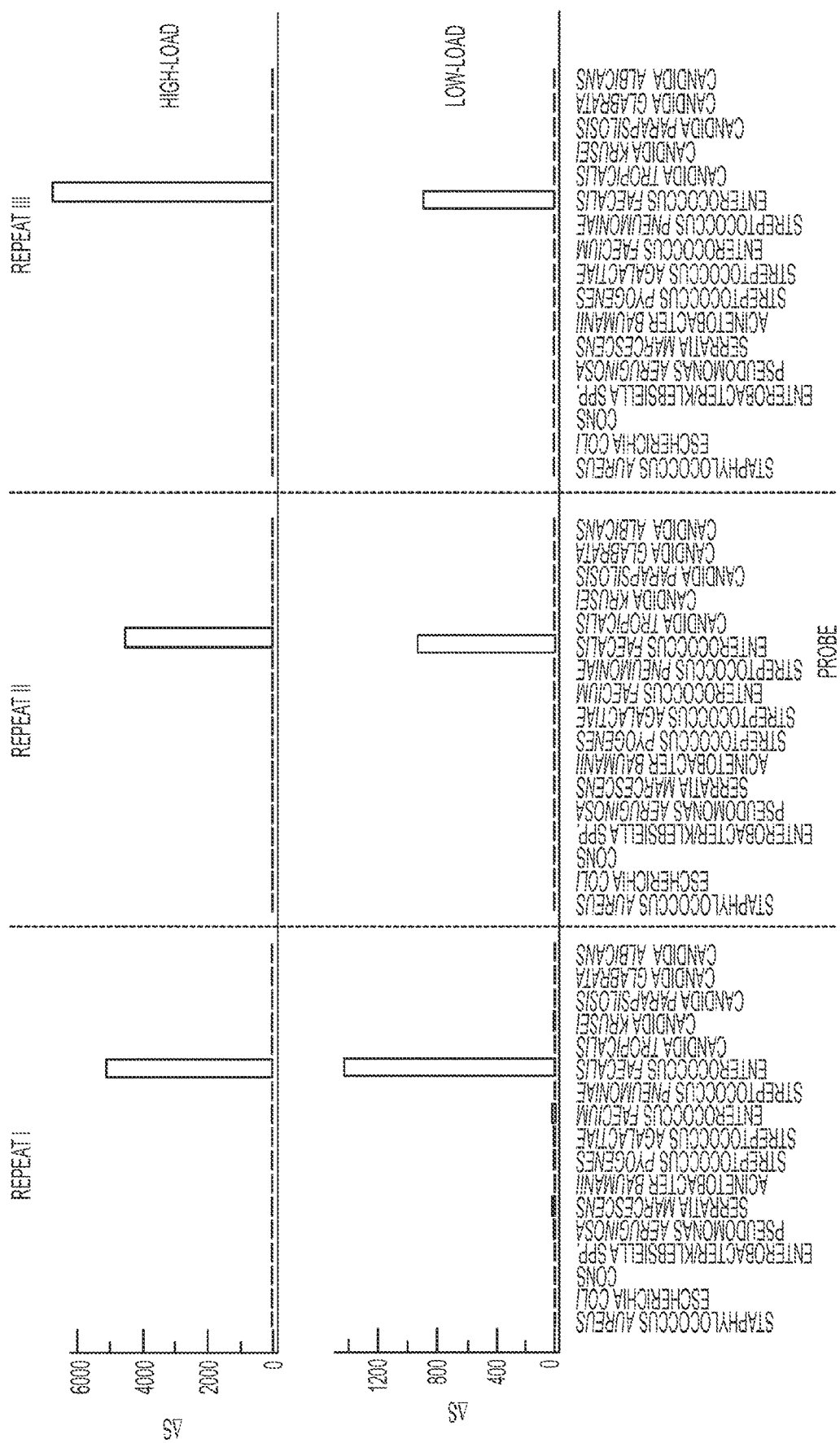
FIG. 13 is a chart showing the detection of *E. faecalis* in human blood samples, wherein *E. faecalis* was inoculated in the blood samples at high loads and low loads.

Results: A clearly identifiable optical signature was only seen in the E. faecalis channel (which came from the chamber activated with a gamma-modified PNA probe specific to E. faecalis). See FIG. 13.

These results show that the compositions and methods disclosed herein can identify at least one specific pathogen from a sample blood. Accordingly, the compositions and methods disclosed herein are useful for the detection and identification of microbes in a sample.

Example 12: Detection of E. faecium

This example shows the detection of E. faecium directly from human whole blood using the methods disclosed herein at two clinically relevant load levels: 10-100 CFU/ml ('high-load'), and 1-10 CFU/ml ('low-load'). The loads specifically were 22 CFU/ml and 2 CFU/ml.

Methods: Fresh human whole-blood drawn into a EDTA vacuette was inoculated with E. faecium (ATCC #700221) at either a 'high-load' or a 'low-load'. The method disclosed in Example 5 to detect microbial DNA was used.

Figure 14:
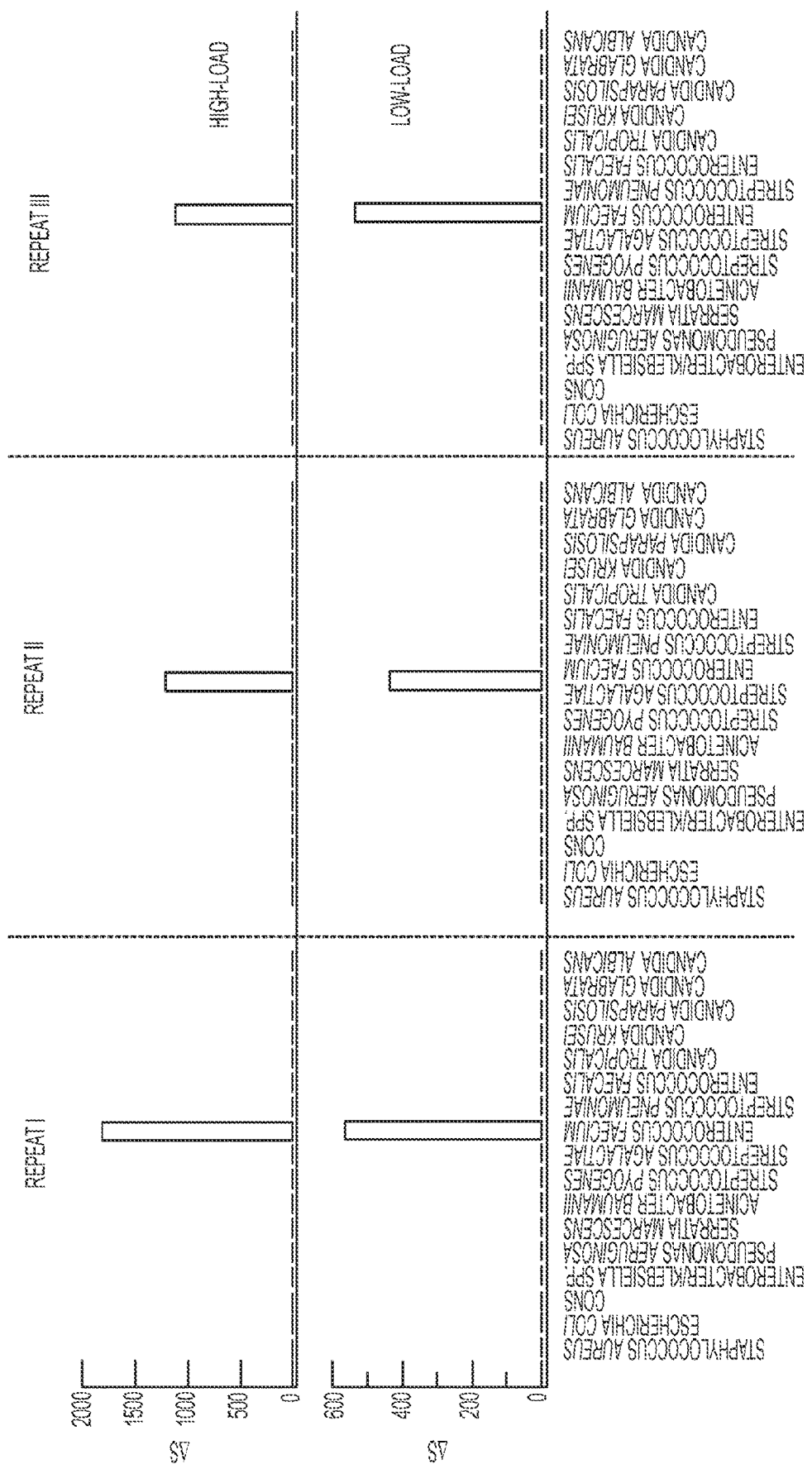
FIG. 14 is a chart showing the detection of *E. faecium* in human blood samples, wherein *E. faecium* was inoculated in the blood samples at high loads and low loads.

Results: A clearly identifiable optical signature was only seen in the E. faecium channel (which came from the chamber activated with a gamma-modified PNA probe specific to E. faecium). See FIG. 14.

These results show that the compositions and methods disclosed herein can identify at least one specific pathogen from a sample blood. Accordingly, the compositions and methods disclosed herein are useful for the detection and identification of microbes in a sample.

Example 13: Detection of E. coli

This example shows the detection of E. coli directly from human whole blood using the methods disclosed herein at two clinically relevant load levels: 10-100 CFU/ml ('high-load'), and 1-10 CFU/ml ('low-load'). The loads specifically were 50 CFU/ml and 5 CFU/ml.

Methods: Fresh human whole-blood drawn into a EDTA vacuette was inoculated with E. coli (ATCC #BAA-2469) at either a 'high-load' or a 'low-load'. The method disclosed in Example 5 to detect microbial DNA was used.

Figure 15:
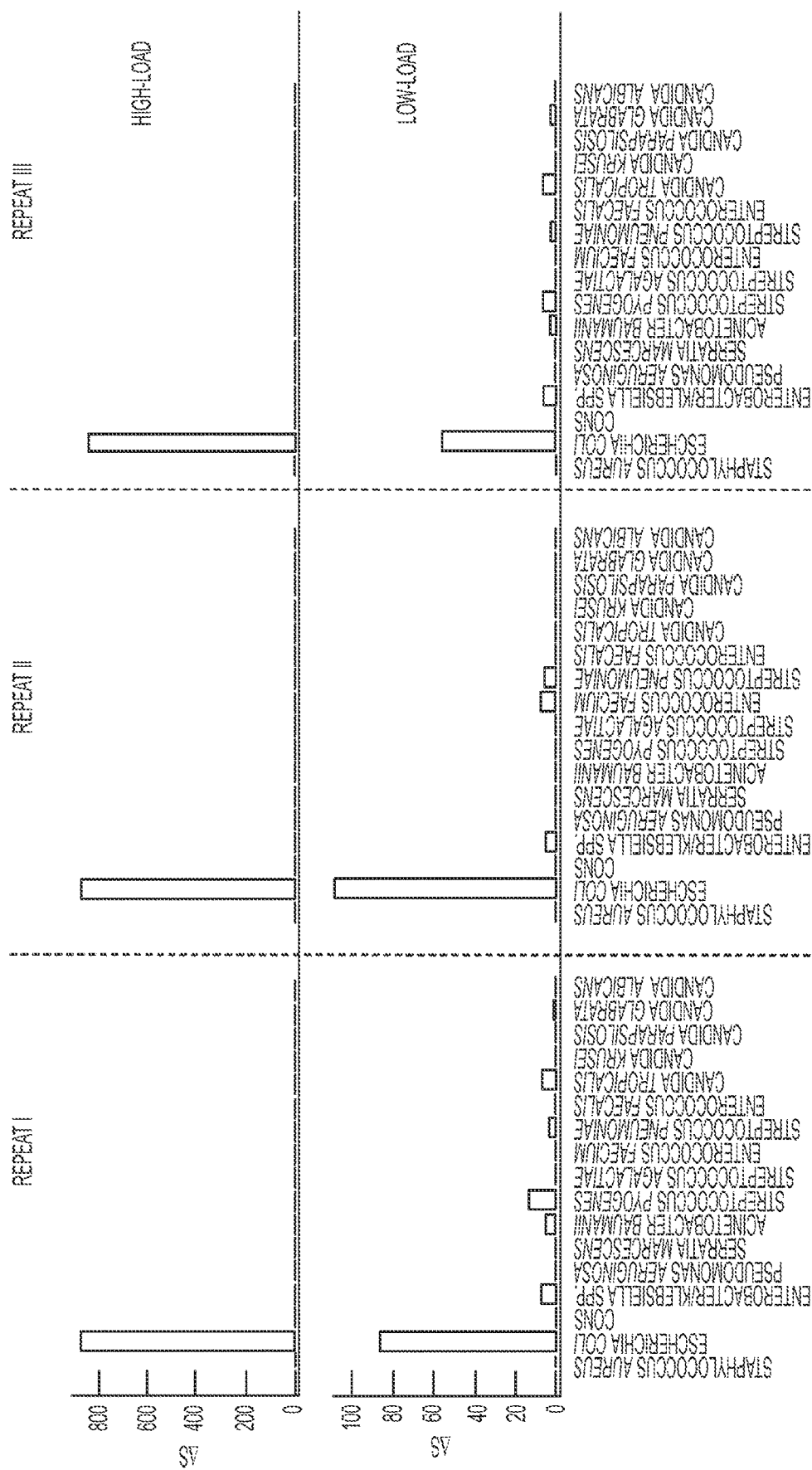
FIG. 15 is a chart showing the detection of *E. coli* in human blood samples, wherein *E. coli* was inoculated in the blood samples at high loads and low loads.

Results: A strong optical signature was seen in the E. coli channel (which came from the chamber activated with a gamma-modified PNA probe specific to E. coli). See FIG. 15.

These results show that the compositions and methods disclosed herein can identify at least one specific pathogen from a sample blood. Accordingly, the compositions and methods disclosed herein are useful for the detection and identification of microbes in a sample.

Example 14: Detection of A. baumannii

This example shows the detection of A. baumannii directly from human whole blood using the methods disclosed herein at two clinically relevant load levels: 10-100 CFU/ml ('high-load'), and 1-10 CFU/ml ('low-load'). The loads specifically were 25 CFU/ml and 5 CFU/ml.

Methods: Fresh human whole-blood drawn into a EDTA vacuette was inoculated with A. baumannii (ATCC #19606) at either a 'high-load' or a 'low-load'. The method disclosed in Example 5 to detect microbial DNA was used.

Figure 16:
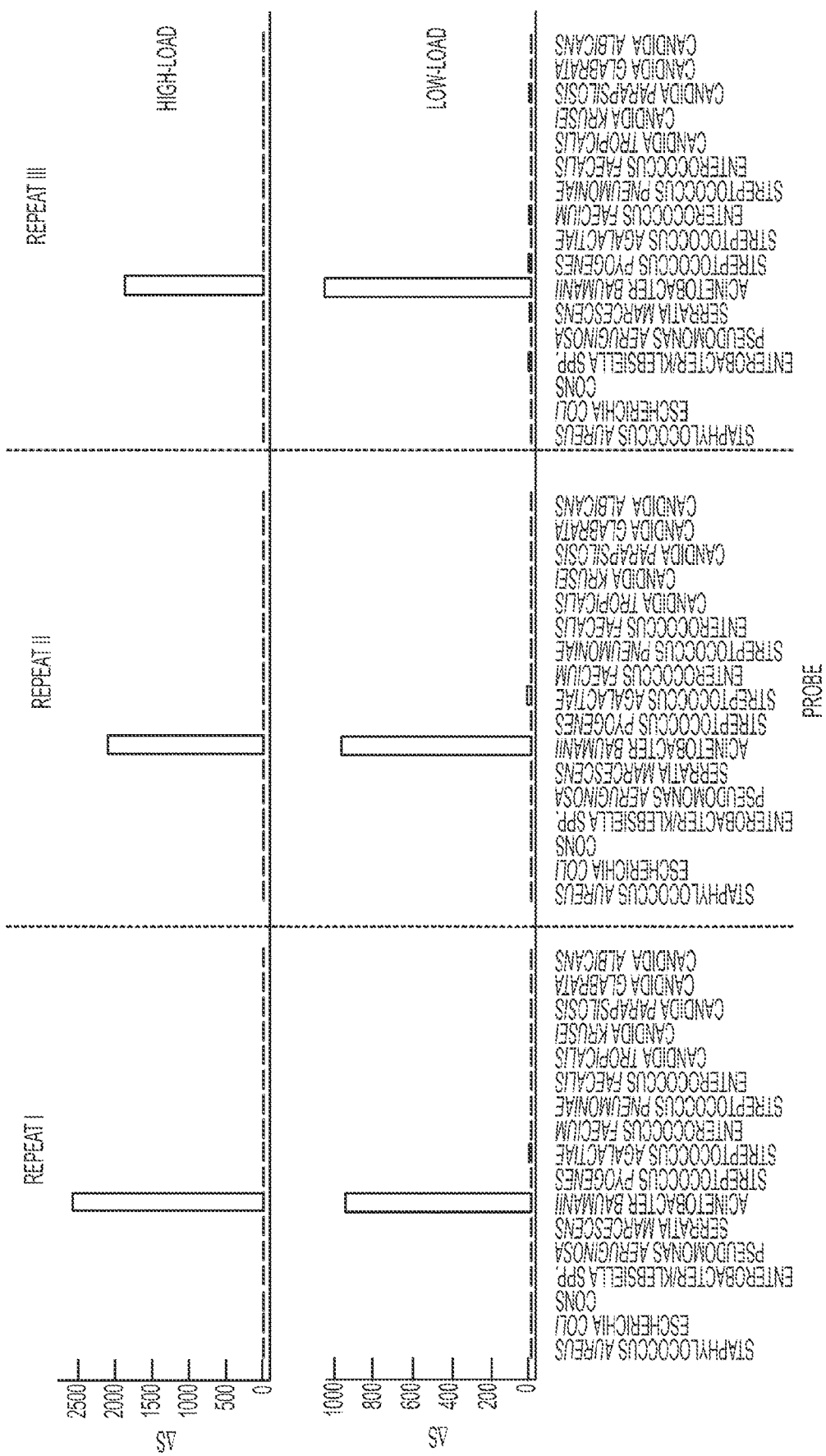
FIG. 16 is a chart showing the detection of *A. baumannii* in human blood samples, wherein *A. baumannii* was inoculated in the blood samples at high loads and low loads.

Results: A clearly identifiable optical signature was only seen in the A. baumannii channel (which came from the chamber activated with a gamma-modified PNA probe specific to A. baumannii). See FIG. 16.

These results show that the compositions and methods disclosed herein can identify at least one specific pathogen from a sample blood. Accordingly, the compositions and methods disclosed herein are useful for the detection and identification of microbes in a sample.

Example 15: Detection of E. aerogenes

This example shows the detection of E. aerogenes directly from human whole blood using the methods disclosed herein at two clinically relevant load levels: 10-100 CFU/ml ('high-load'), and 1-10 CFU/ml ('low-load'). The loads specifically were 22 CFU/ml and 2 CFU/ml.

Methods: Fresh human whole-blood drawn into a EDTA vacuette was inoculated with *E. aerogenes* (ATCC #13048) at either a 'high-load' or a 'low-load'. The method disclosed in Example 5 to detect microbial DNA was used.

Figure 17:
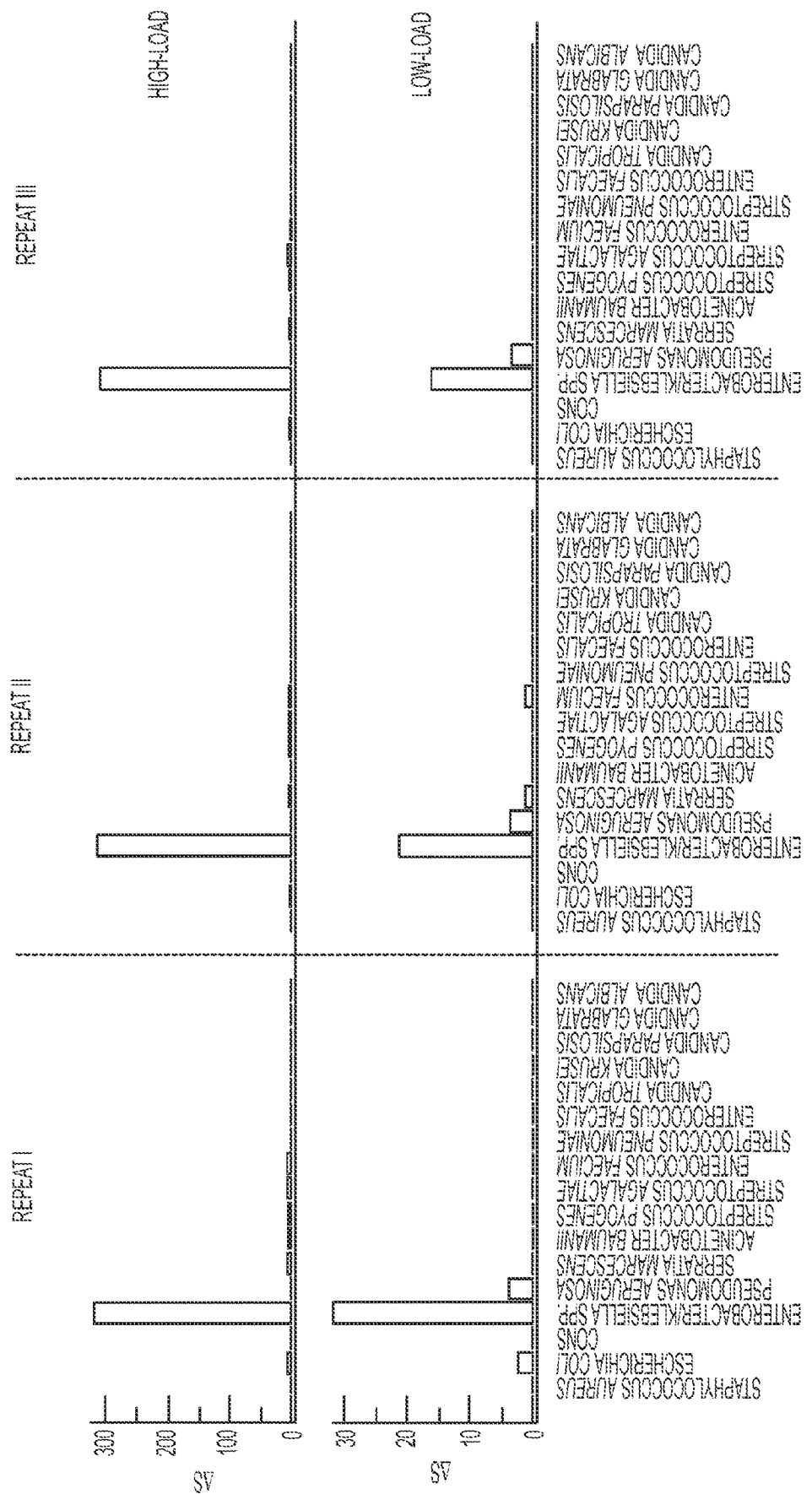
FIG. 17 is a chart showing the detection of *E. aerogenes* in human blood samples, wherein *E. aerogenes* was inoculated in the blood samples at high loads and low loads.

Results: A clearly identifiable optical signature was only seen in the *Enterobacter* spp./*Klebsiella* spp. channel (which came from the chamber activated with a gamma-modified PNA probe specific to *E. aerogenes/E. cloacae/K. pneumoniae/K. oxytoca*). See FIG. 17.

These results show that the compositions and methods disclosed herein can identify at least one specific pathogen from a sample blood. Accordingly, the compositions and methods disclosed herein are useful for the detection and identification of microbes in a sample.

Example 16: Detection of *E. cloacae*

This example shows the detection of *E. cloacae* directly from human whole blood using the methods disclosed herein at two clinically relevant load levels: 10-100 CFU/ml ('high-load'), and 1-10 CFU/ml ('low-load'). The loads specifically were 38 CFU/ml and 4 CFU/ml.

Methods: Fresh human whole-blood drawn into a EDTA vacuette was inoculated with *E. cloacae* (ATCC #13047) at either a 'high-load' or a 'low-load'. The method disclosed in Example 5 to detect microbial DNA was used.

Figure 18:
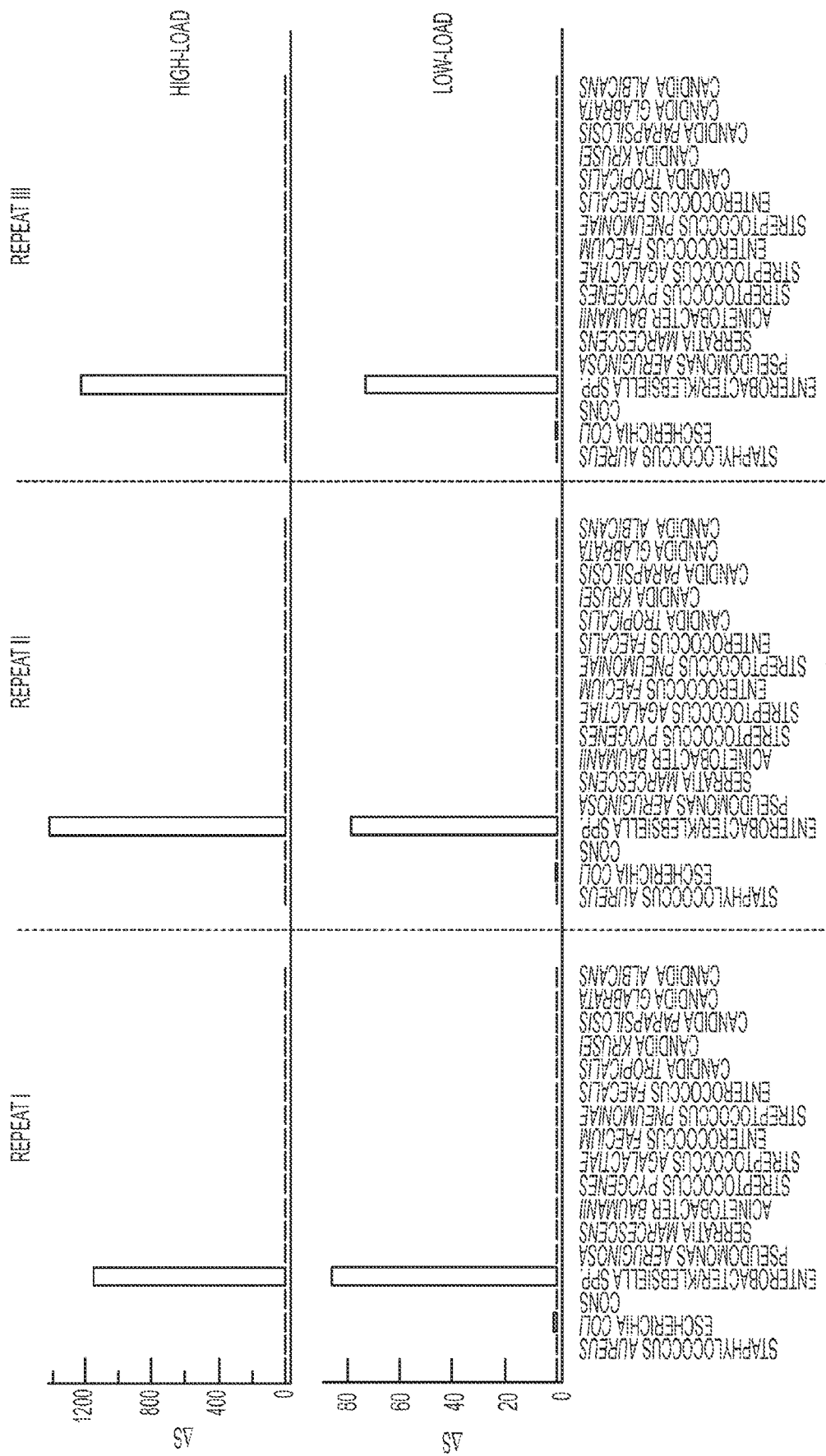
FIG. 18 is a chart showing the detection of *E. cloacae* in human blood samples, wherein *E. cloacae* was inoculated in the blood samples at high loads and low loads.

Results: A clearly identifiable optical signature was only seen in the *Enterobacter* spp./*Klebsiella* spp. channel (which came from the chamber activated with a gamma-modified PNA probe specific to *E. aerogenes/E. cloacae/K. pneumoniae/K. oxytoca*). See FIG. 18.

These results show that the compositions and methods disclosed herein can identify at least one specific pathogen from a sample blood. Accordingly, the compositions and methods disclosed herein are useful for the detection and identification of microbes in a sample.

Example 17: Detection of *K. pneumoniae*

This example shows the detection of *K. pneumoniae* directly from human whole blood using the methods disclosed herein at two clinically relevant load levels: 10-100 CFU/ml ('high-load'), and 1-10 CFU/ml ('low-load'). The loads specifically were 60 CFU/ml and 6 CFU/ml.

Methods: Fresh human whole-blood drawn into a EDTA vacuette was inoculated with *K. pneumoniae* (ATCC #27736) at either a 'high-load' or a 'low-load'. The method disclosed in Example 5 to detect microbial DNA was used.

Figure 19:
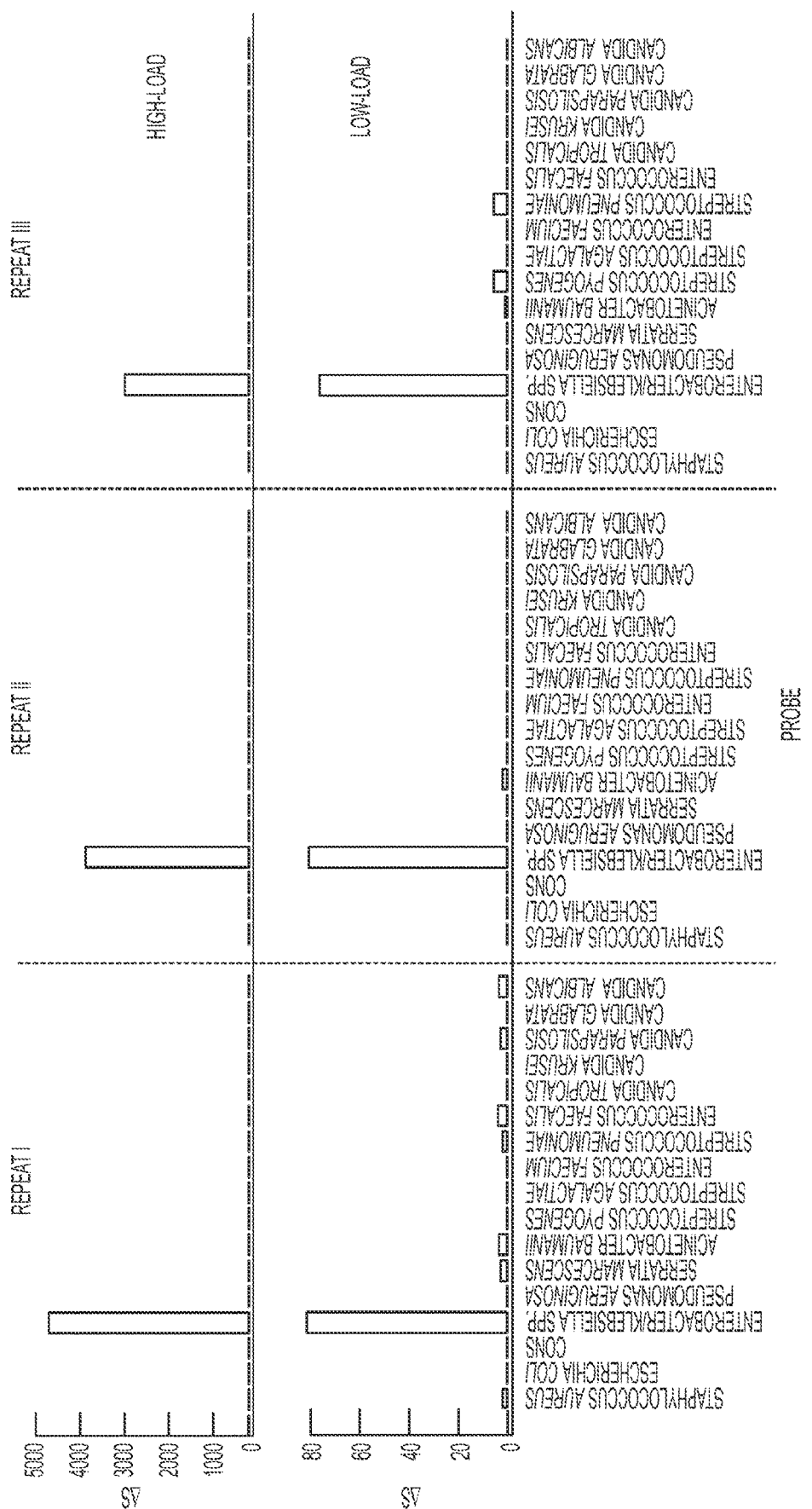
FIG. 19 is a chart showing the detection of *K. pneumoniae* in human blood samples, wherein *K. pneumoniae* was inoculated in the blood samples at high loads and low loads.

Results: A strong optical signature was seen in the *Enterobacter* spp./*Klebsiella* spp. channel (which came from the chamber activated with a gamma-modified PNA probe specific to *E. aerogenes/E. cloacae/K. pneumoniae/K. oxytoca*). See FIG. 19.

These results show that the compositions and methods disclosed herein can identify at least one specific pathogen from a sample blood. Accordingly, the compositions and methods disclosed herein are useful for the detection and identification of microbes in a sample.

Example 18: Detection of *K. oxytoca*

This example shows the detection of *K. oxytoca* directly from human whole blood using the methods disclosed herein at two clinically relevant load levels: 10-100 CFU/ml ('high-load'), and 1-10 CFU/ml ('low-load'). The loads specifically were 24 CFU/ml and 2 CFU/ml.

Methods: Fresh human whole-blood drawn into a EDTA vacuette was inoculated with *K. oxytoca* (ATCC #49131) at either a 'high-load' or a 'low-load'. The method disclosed in Example 5 to detect microbial DNA was used.

Figure 20:
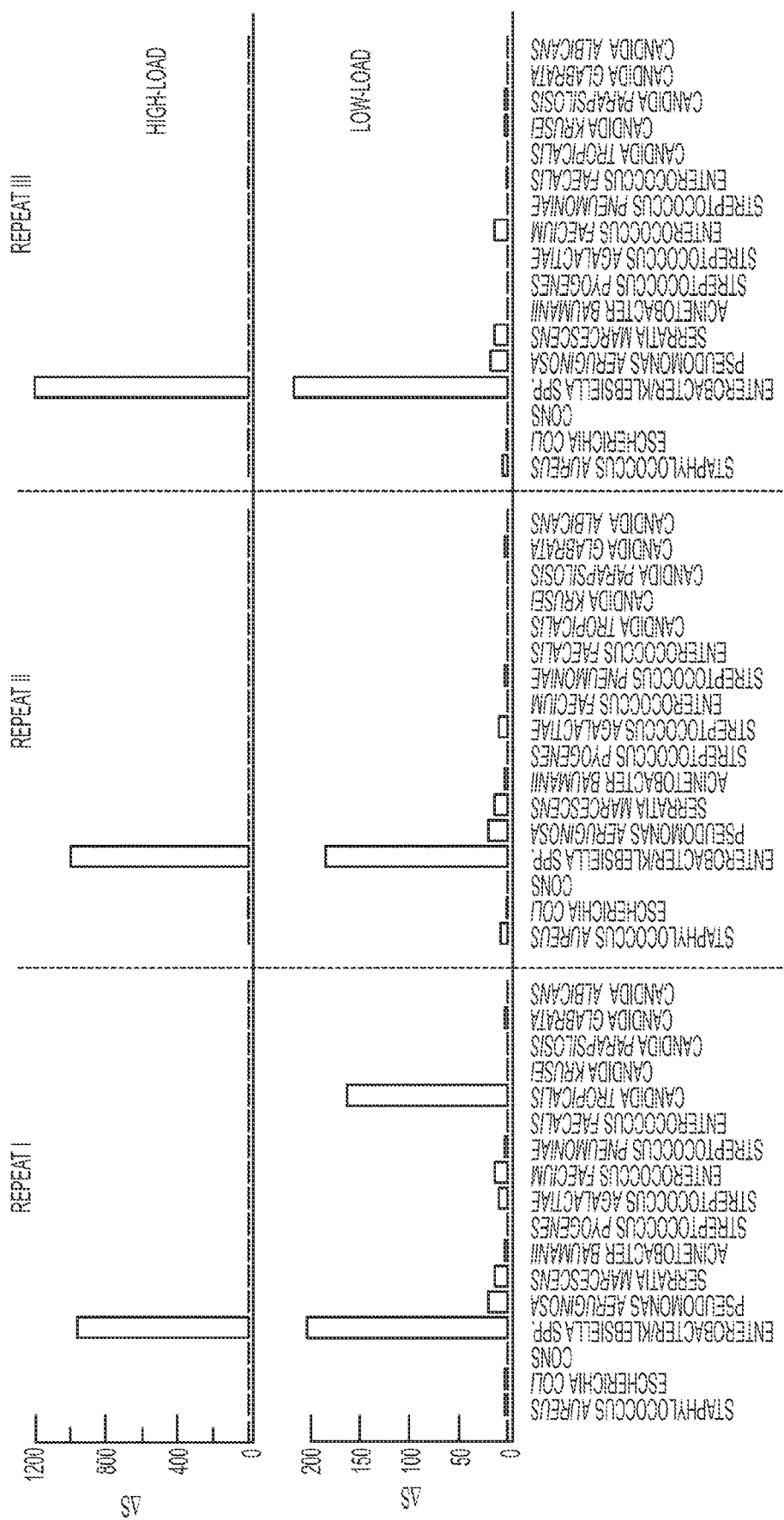
FIG. 20 is a chart showing the detection of *K. oxytoca* in human blood samples, wherein *K. oxytoca* was inoculated in the blood samples at high loads and low loads.

Results: A strong optical signature was seen in the *Enterobacter* spp./*Klebsiella* spp. channel (which came from the chamber activated with a gamma-modified PNA probe specific to *E. aerogenes/E. cloacae/K. pneumonia/K. oxytoca*). See FIG. 20.

These results show that the compositions and methods disclosed herein can identify at least one specific pathogen from a sample blood. Accordingly, the compositions and methods disclosed herein are useful for the detection and identification of microbes in a sample.

Example 19: Detection of *P. aeruginosa*

This example shows the detection of *P. aeruginosa* directly from human whole blood using the methods disclosed herein at two clinically relevant load levels: 10-100 CFU/ml ('high-load'), and 1-10 CFU/ml ('low-load'). The loads specifically were 60 CFU/ml and 6 CFU/ml.

Methods: Fresh human whole-blood drawn into a EDTA vacuette was inoculated with *P. aeruginosa* (ATCC #10145) at either a 'high-load' or a 'low-load'. The method disclosed in Example 5 to detect microbial DNA was used.

Figure 21:
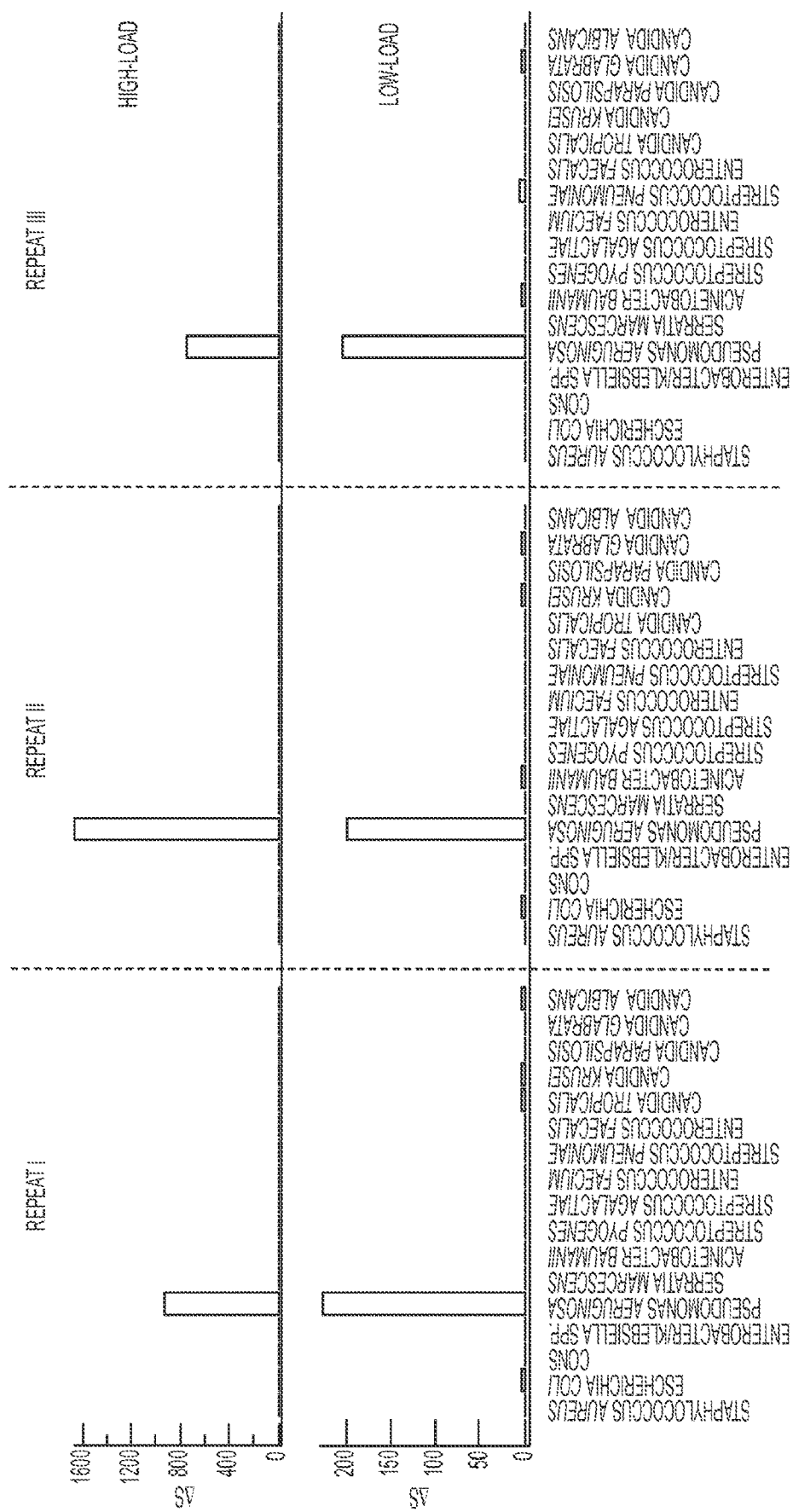
FIG. 21 is a chart showing the detection of *P. aeruginosa* in human blood samples, wherein *P. aeruginosa* was inoculated in the blood samples at high loads and low loads.

Results: A clearly identifiable optical signature was only seen in the *P. aeruginosa* channel (which came from the chamber activated with a gamma-modified PNA probe specific to *P. aeruginosa*). See FIG. 21.

These results show that the compositions and methods disclosed herein can identify at least one specific pathogen from a sample blood. Accordingly, the compositions and methods disclosed herein are useful for the detection and identification of microbes in a sample.

Example 20: Detection of *S. marcescens*

This example shows the detection of *S. marcescens* directly from human whole blood using the methods disclosed herein at two clinically relevant load levels: 10-100 CFU/ml ('high-load'), and 1-10 CFU/ml ('low-load'). The loads specifically were 59 CFU/ml and 6 CFU/ml.

Methods: Fresh human whole-blood drawn into a EDTA vacuette was inoculated with *S. marcescens* (ATCC #13880) at either a 'high-load' or a 'low-load'. The method disclosed in Example 5 to detect microbial DNA was used.

Figure 22:
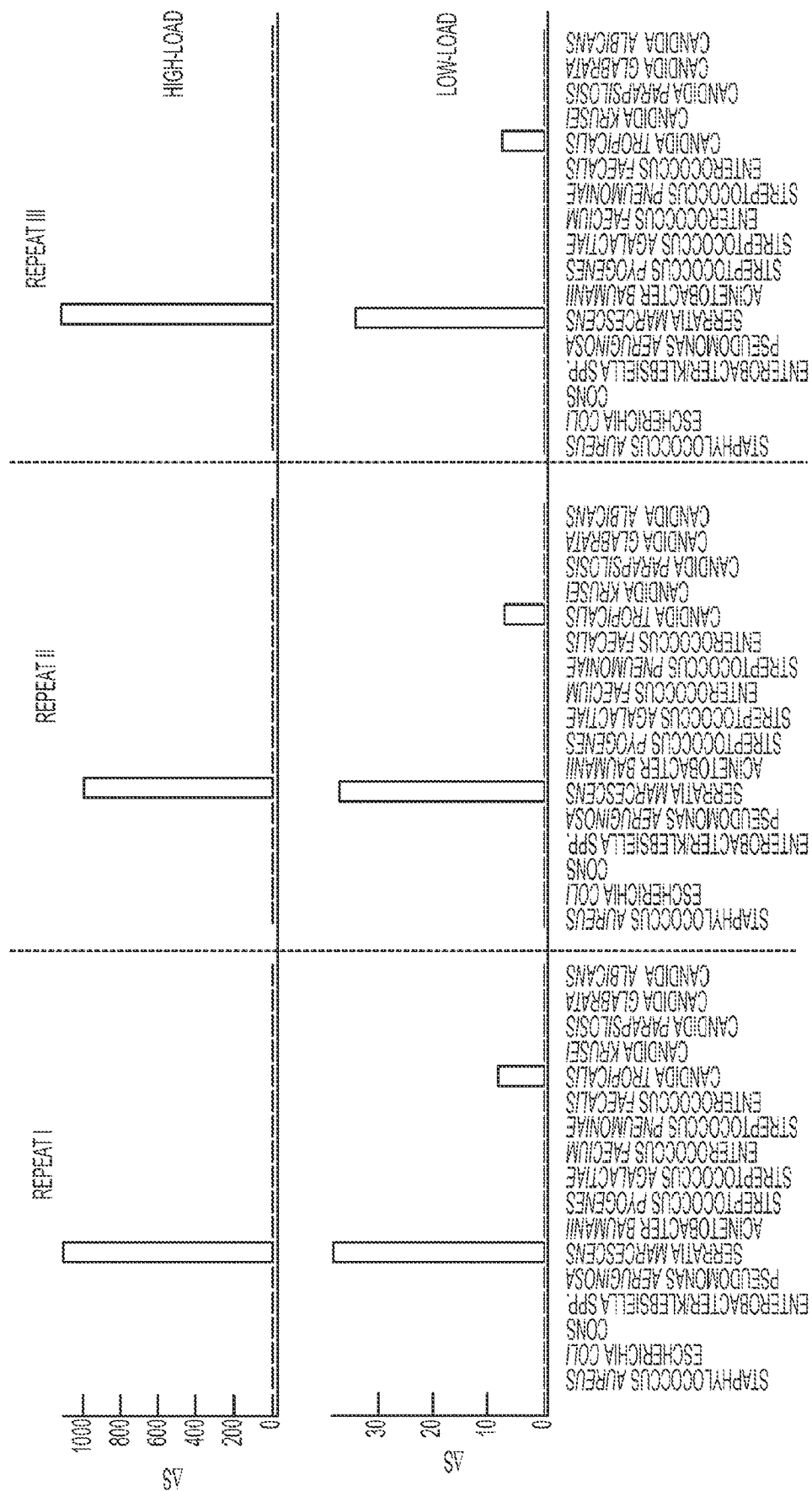
FIG. 22 is a chart showing the detection of *S. marcescens* in human blood samples, wherein *S. marcescens* was inoculated in the blood samples at high loads and low loads.

Results: A strong optical signature was seen in the *S. marcescens* channel (which came from the chamber activated with a gamma-modified PNA probe specific *S. marcescens*). See FIG. 22.

These results show that the compositions and methods disclosed herein can identify at least one specific pathogen from a sample blood. Accordingly, the compositions and methods disclosed herein are useful for the detection and identification of microbes in a sample.

Example 21: Detection of *C. albicans*

This example shows the detection of *C. albicans* directly from human whole blood using the methods disclosed herein at two clinically relevant load levels: 10-100 CFU/ml ('high-load'), and 1-10 CFU/ml ('low-load'). The loads specifically were 27 CFU/ml and 3 CFU/ml.

Methods: Fresh human whole-blood drawn into a EDTA vacuette was inoculated with *C. albicans* (ATCC #90028) at either a 'high-load' or a 'low-load'. The method disclosed in Example 5 to detect microbial DNA was used.

Figure 23:
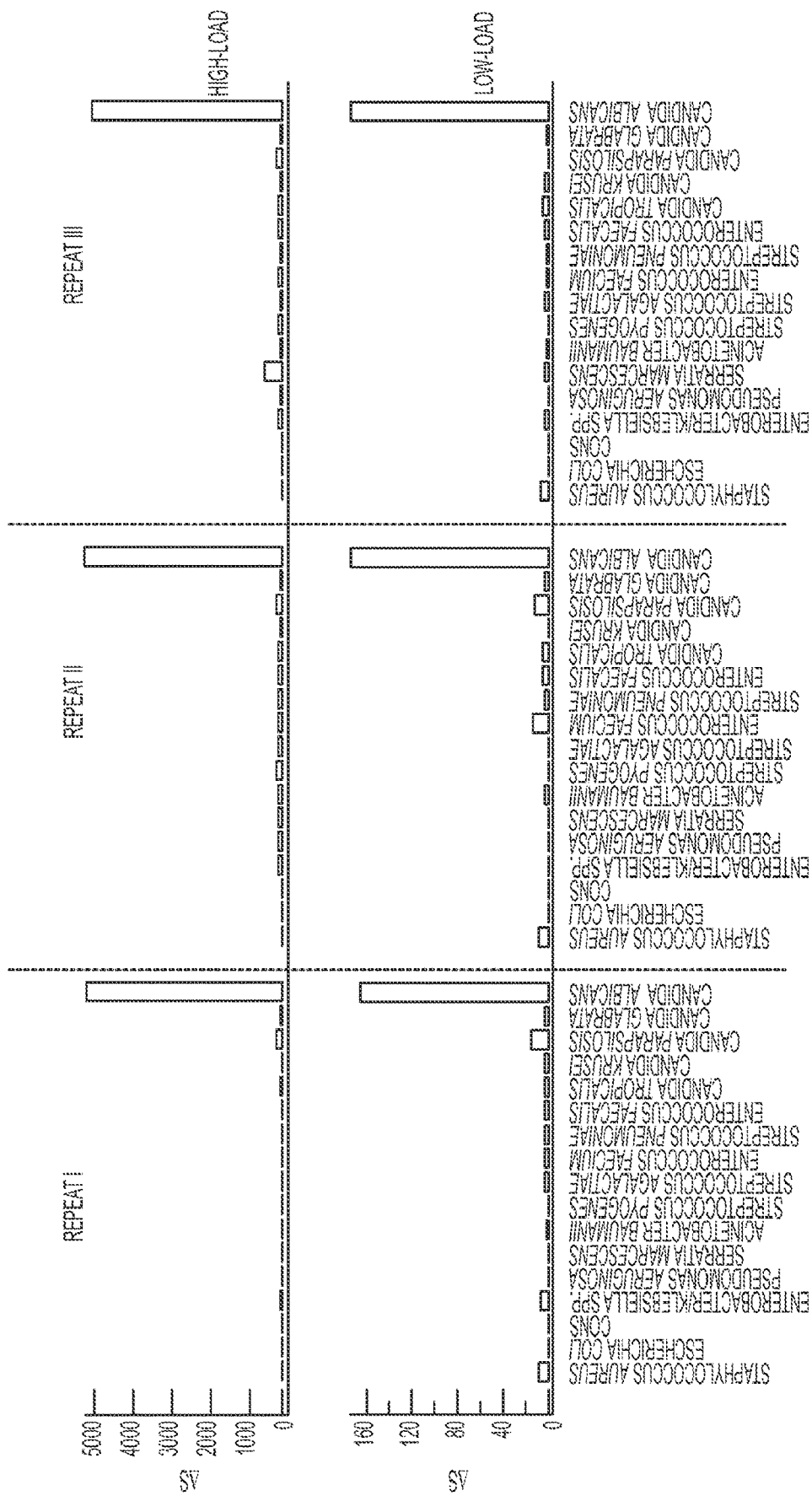
FIG. 23 is a chart showing the detection of *C. albicans* in human blood samples, wherein *C. albicans* was inoculated in the blood samples at high loads and low loads.

Results: A strong optical signature was seen in the *C. albicans* channel (which came from the chamber activated with a gamma-modified PNA probe specific *C. albicans*). See FIG. 23.

These results show that the compositions and methods disclosed herein can identify at least one specific pathogen from a sample blood. Accordingly, the compositions and methods disclosed herein are useful for the detection and identification of microbes in a sample.

Example 22: Detection of *C. glabrata*

This example shows the detection of *C. glabrata* directly from human whole blood using the methods disclosed herein at two clinically relevant load levels: 10-100 CFU/ml ('high-load'), and 1-10 CFU/ml ('low-load'). The loads specifically were 17 CFU/ml and 2 CFU/ml.

Methods: Fresh human whole-blood drawn into a EDTA vacuette was inoculated with *C. glabrata* (ATCC #MYA-2950) at either a 'high-load' or a 'low-load'. The method disclosed in Example 5 to detect microbial DNA was used.

Figure 24:
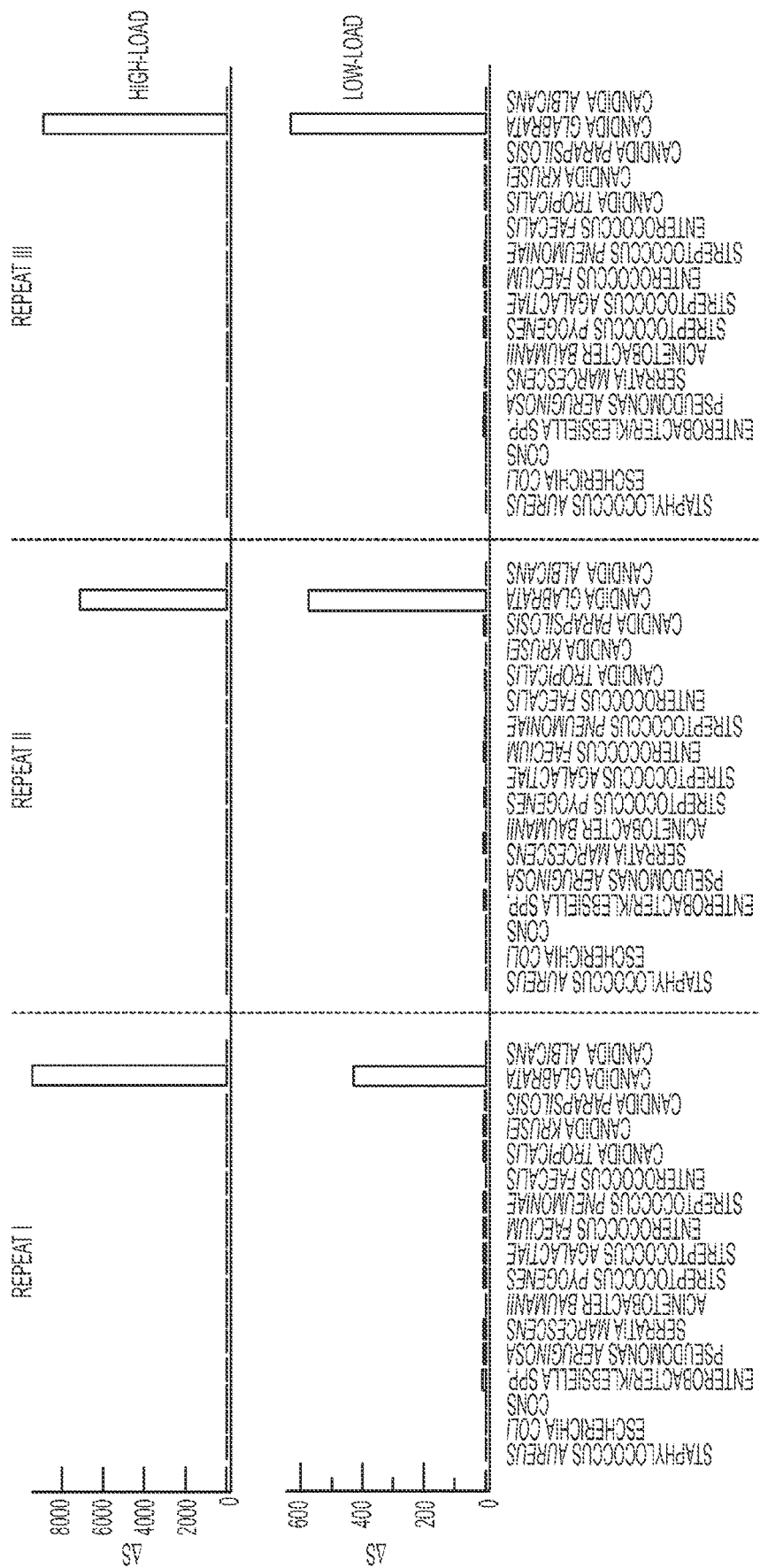
FIG. 24 is a chart showing the detection of *C. glabrata* in human blood samples, wherein *C. glabrata* was inoculated in the blood samples at high loads and low loads.

Results: A clearly identifiable optical signature was only seen in the *C. glabrata* channel (which came from the chamber activated with a gamma-modified PNA probe specific *C. glabrata*). See FIG. 24.

These results show that the compositions and methods disclosed herein can identify at least one specific pathogen from a sample blood. Accordingly, the compositions and methods disclosed herein are useful for the detection and identification of microbes in a sample.

Example 23: Detection of *C. tropicalis*

This example shows the detection of *C. tropicals* directly from human whole blood using the methods disclosed herein at two clinically relevant load levels: 10-100 CFU/ml ('high-load'), and 1-10 CFU/ml ('low-load'). The loads specifically were 31 CFU/ml and 6 CFU/ml.

Methods: Fresh human whole-blood drawn into a EDTA vacuette was inoculated with *C. tropicals* (ATCC #13803) at either a 'high-load' or a 'low-load'. The method disclosed in Example 5 to detect microbial DNA was used.

Figure 25:
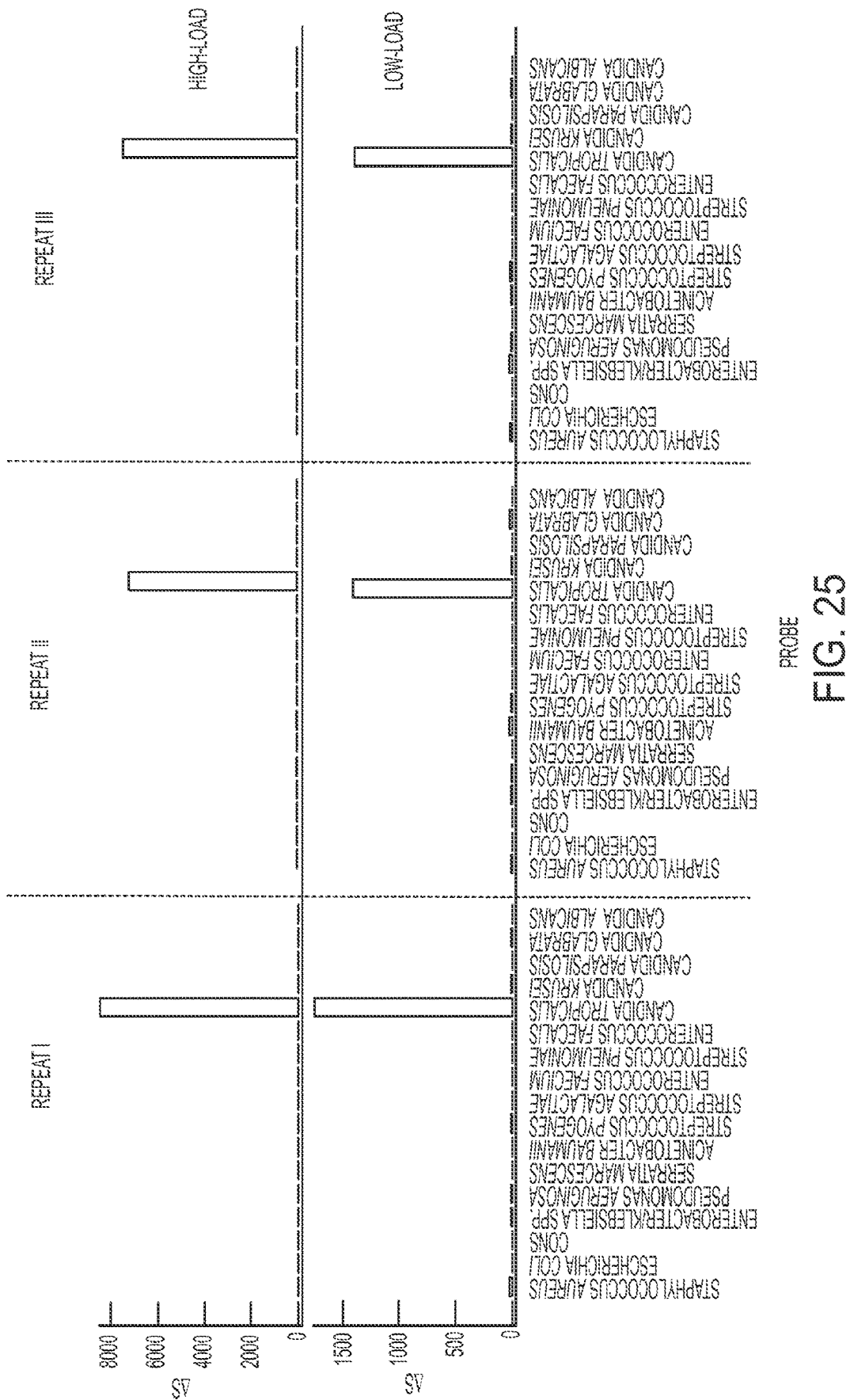
FIG. 25 is a chart showing the detection of *C. tropicalis* in human blood samples, wherein *C. tropicalis* was inoculated in the blood samples at high loads and low loads.

Results: A clearly identifiable optical signature was only seen in the *C. tropicals* channel (which came from the chamber activated with a gamma-modified PNA probe specific *C. tropicals*). See FIG. 25.

These results show that the compositions and methods disclosed herein can identify at least one specific pathogen from a sample blood. Accordingly, the compositions and methods disclosed herein are useful for the detection and identification of microbes in a sample.

Example 24: Detection of *C. parapsilosis*

This example shows the detection of *C. parapsilosis* directly from human whole blood using the methods disclosed herein at two clinically relevant load levels: 10-100 CFU/ml ('high-load'), and 1-10 CFU/ml ('low-load'). The loads specifically were 45 CFU/ml and 5 CFU/ml.

Methods: Fresh human whole-blood drawn into a EDTA vacuette was inoculated with *C. parapsilosis* (ATCC #14243) at either a 'high-load' or a 'low-load'. The method disclosed in Example 5 to detect microbial DNA was used.

Figure 26:
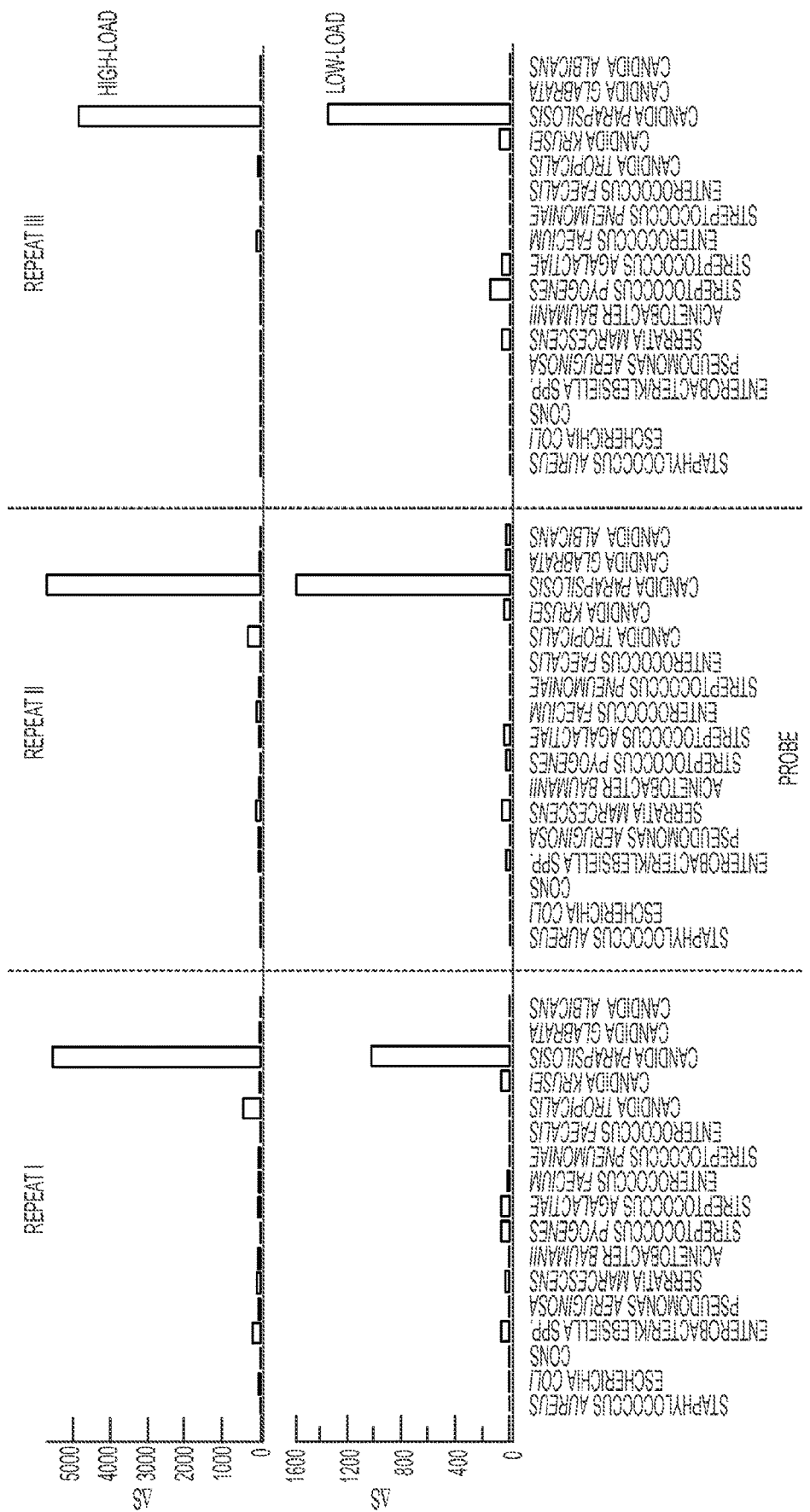
FIG. 26 is a chart showing the detection of *C. parapsilosis* in human blood samples, wherein *C. parapsilosis* was inoculated in the blood samples at high loads and low loads.

Results: A strong optical signature was seen in the *C. parapsilosis* channel (which came from the chamber activated with a gamma-modified PNA probe specific *C. parapsilosis*). See FIG. 26.

These results show that the compositions and methods disclosed herein can identify at least one specific pathogen from a sample blood. Accordingly, the compositions and methods disclosed herein are useful for the detection and identification of microbes in a sample.

Example 25: Detection of *C. krusei*

This example shows the detection of *C. krusei* directly from human whole blood using the methods disclosed herein at two clinically relevant load levels: 10-100 CFU/ml ('high-load'), and 1-10 CFU/ml ('low-load'). The loads specifically were 45 CFU/ml and 5 CFU/ml.

Methods: Fresh human whole-blood drawn into a EDTA vacuette was inoculated with *C. krusei* (ATCC #13803) at either a 'high-load' or a 'low-load'. The method disclosed in Example 5 to detect microbial DNA was used.

Figure 27:
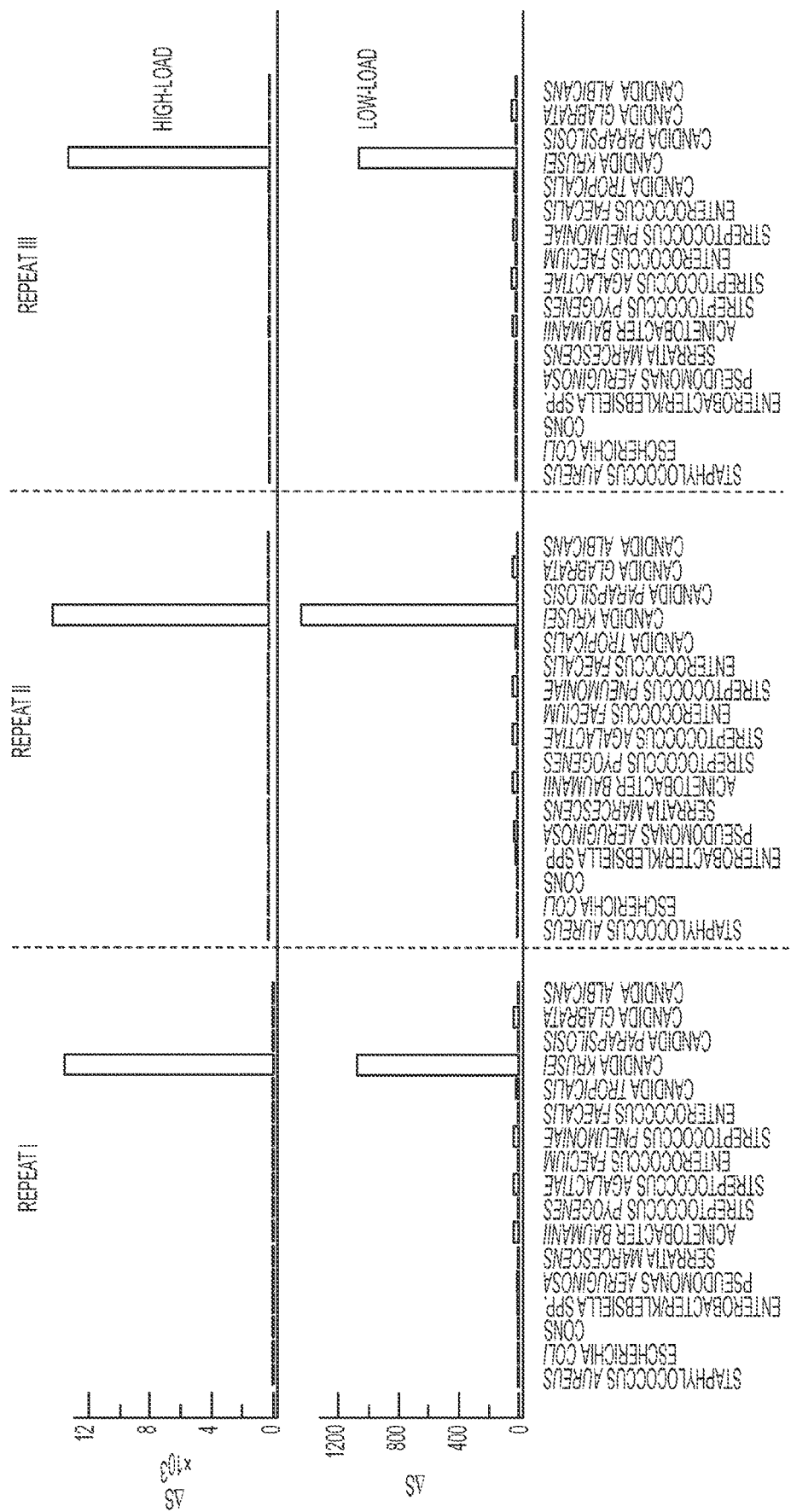
FIG. 27 is a chart showing the detection of *C. krusei* in human blood samples, wherein *C. krusei* was inoculated in the blood samples at high loads and low loads.

Results: A clearly identifiable optical signature was only seen in the *C. krusei* channel (which came from the chamber activated with a gamma-modified PNA probe specific *C. krusei*). See FIG. 27.

These results show that the compositions and methods disclosed herein can identify at least one specific pathogen from a sample blood. Accordingly, the compositions and methods disclosed herein are useful for the detection and identification of microbes in a sample.

Example 26: Detection of Co-Infection with *E. coli* and *C. albicans*

This example shows the co-detection of both *E. coli* and *C. albicans* directly from human whole blood using the methods disclosed herein at clinically relevant load levels: The loads specifically were 17 CFU/ml and 3 CFU/ml for *E. coli* and *C. albicans*, respectively Methods: Fresh human whole-blood drawn into a EDTA vacuette was inoculated with both *E. coli* (ATCC #BAA-2469) and *C. albicans* (ATCC #90028). The method disclosed in Example 5 to detect microbial DNA was used.

Figure 28:
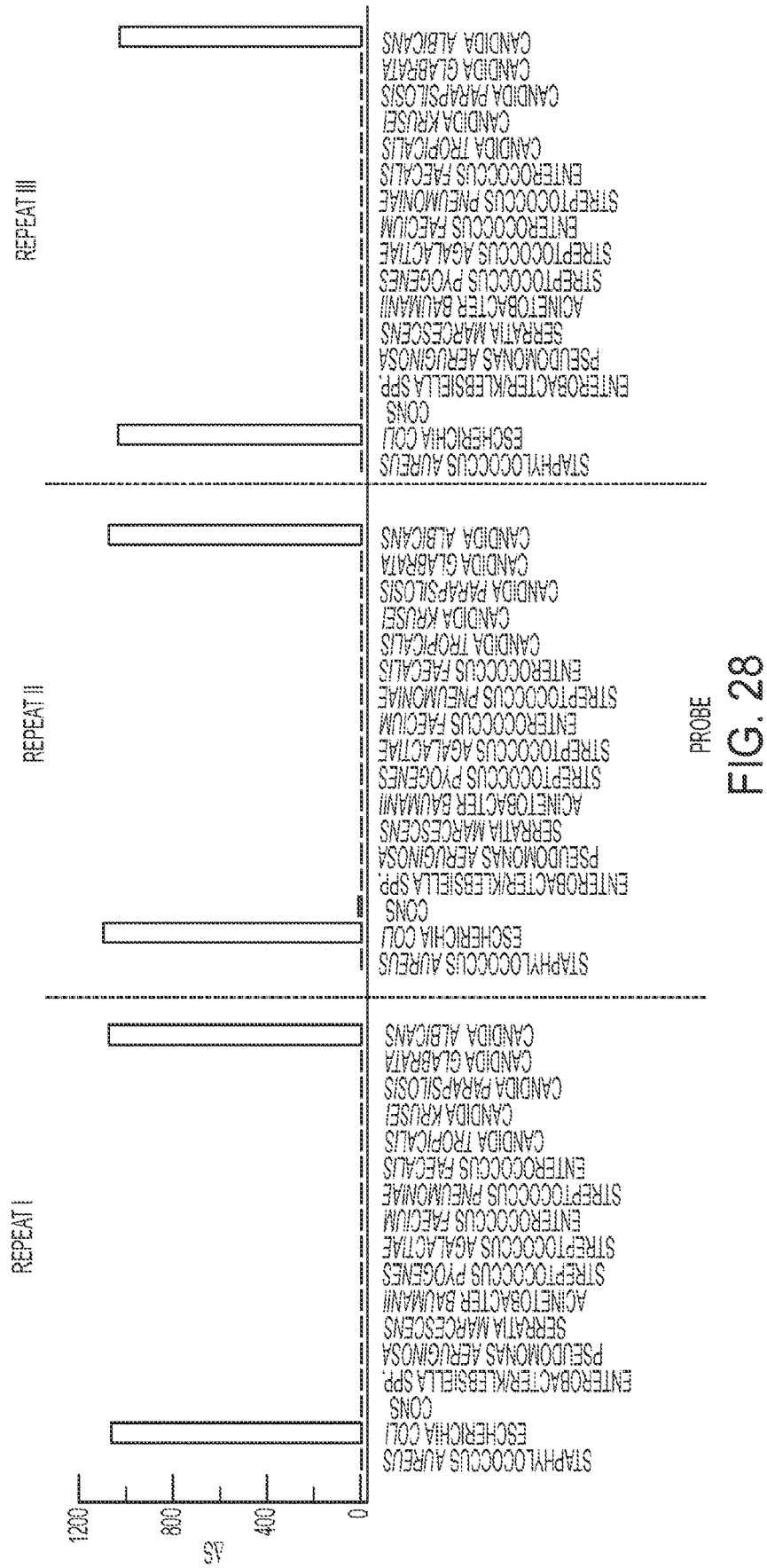
FIG. 28 is a chart showing the detection of *E. coli* and *C. albicans* in human blood samples, wherein *S. aureus* was inoculated in the blood samples at high loads and low loads.

Results: A clearly identifiable optical signature was only seen in the *E. coli* and *C. albicans* channels (which came from the chamber activated with either a gamma-modified PNA probe specific *E. coli* or *C. albicans*). See FIG. 28.

These results show that the compositions and methods disclosed herein can identify at least one specific pathogen from a sample blood. Accordingly, the compositions and methods disclosed herein are useful for the detection and identification of microbes in a sample.

Example 27: Detection of Co-Infection with *E. coli* and *S. aureus*

This example shows the co-detection of both *E. coli* and *S. aureus* directly from human whole blood using the methods disclosed herein at clinically relevant load levels: The loads specifically were 17 CFU/ml and 8 CFU/ml for *E. coli* and *S. aureus*, respectively Methods: Fresh human whole-blood drawn into a EDTA vacuette was inoculated with both *E. coli* (ATCC #BAA-2469) and *S. aureus* (ATCC #43300). The method disclosed in Example 5 to detect microbial DNA was used.

Figure 29:
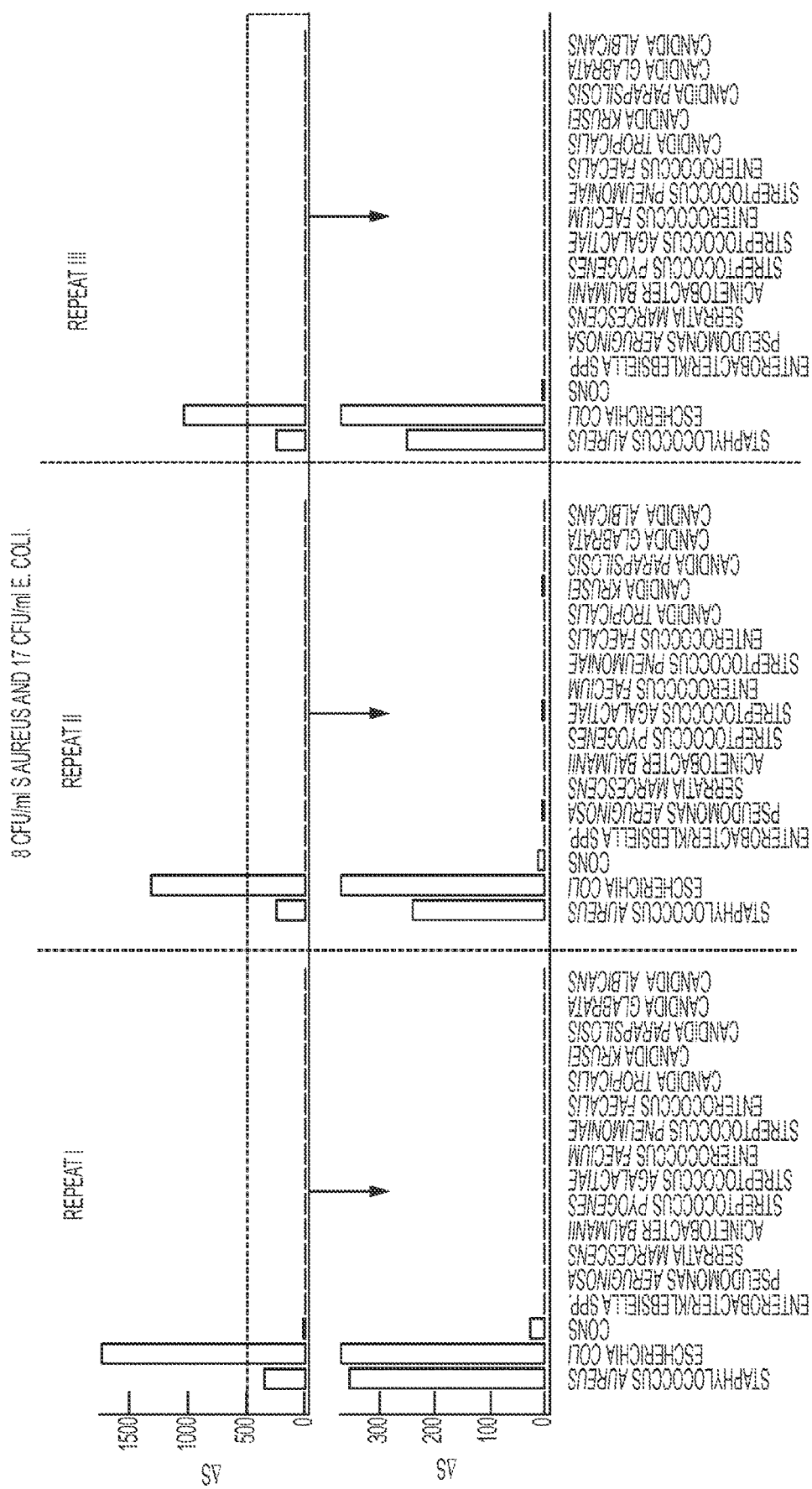
FIG. 29 is a chart showing the detection of *E. coli* and *S. aureus* in human blood samples, wherein *E. coli* and *S. aureus* was inoculated in the blood samples at high loads and low loads.

Results: A strong optical signature was seen in the *E. coli* and *S. aureus* channels (which came from the chamber activated with either a gamma-modified PNA probe specific *E. coli* or *S. aureus*). See FIG. 29.

These results show that the compositions and methods disclosed herein can identify at least one specific pathogen from a sample blood. Accordingly, the compositions and methods disclosed herein are useful for the detection and identification of microbes in a sample.

EQUIVALENTS

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. A method for identifying one or more specific microbial species in a sample obtained from a subject, the method comprising:
   (a) adding a eukaryotic cell lysis solution to the sample to facilitate depletion of eukaryotic DNA from the sample, wherein the eukaryotic cell lysis solution selectively targets and predominantly lyses eukaryotic cells as opposed to microbial cells to release eukaryotic DNA;
   (b) lysing one or more microbial cells in the sample, wherein the lysing of one or more microbial cells releases a plurality of microbial genetic materials;
   (c) isolating the plurality of microbial genetic materials;
   (d) amplifying the plurality of microbial genetic materials;
   (e) contacting the amplified microbial genetic materials with one or more DNA Invading Artificial Nucleic Acids (DIANAs) that are capable of specifically invading duplex nucleic acids, wherein the one or more DIANAs are gamma-modified PNA probes and comprise a sequence that is complementary to a bacterial 16S rDNA nucleic acid, or a sequence that is complementary to a fungal 18S rDNA nucleic acid; and
   (f) detecting binding of one or more DIANAs to the amplified microbial genetic material of its respective single species or group of microbes, wherein the detection of binding indicates the presence of one or more specific microbial species or groups of microbes in the sample,
   wherein the eukaryotic cell lysis solution combined with the sample comprises between about 0.25% to 1% (v/v) of a Tween surfactant, between about 0.2% to 0.65% (v/v) of Triton or IGEPAL, has a pH of about 6-9, and contains less than about 0.15 M of monovalent salts,
   wherein the method is capable of detecting a microbial species in the sample that has a load level as low as 1-10 CFU/ml.

2. The method of claim 1, wherein the isolated plurality of genomic materials are purified.

3. The method of claim 1, wherein the eukaryotic DNA is removed from the sample using an anionic-exchange microparticle under conditions of a pH of about 6-9 with monovalent salt concentrations of about 0.1 M-0.85 M.

4. The method of claim 1, wherein the sample is blood or sputum.

5. The method of claim 1, wherein the subject is a mammal.

6. The method of claim 1, wherein isolating the plurality of microbial genetic materials comprises binding the microbial genetic material to an anionic-exchange microparticle and washing the anion-exchange microparticle bound to the microbial genetic material.

7. The method of claim 1, wherein the isolated microbial genetic material is RNA, DNA, or a combination thereof.

8. The method of claim 7, wherein the DNA is single stranded or double stranded.

9. The method of claim 1, wherein lysing one or more microbial cells in the sample comprises contacting the one or more microbial cells with a lysis buffer comprising a DNA intercalating dye.

10. The method of claim 9, wherein the DNA intercalating dye is ethidium monazide (EMA), propidium monoazide (PMA), or a combination thereof.

11. The method of claim 6, wherein washing the anion-exchange microparticle bound to the microbial genetic material comprises contacting the isolated plurality of microbial genetic materials with a wash buffer comprising a pH between about 3 to 7.5, at least one monovalent salt, wherein the monovalent salt concentration is between about 0.75 M to 2.75 M, at least one non-ionic detergent, wherein the non-ionic detergent concentration is between about 0.01% to 1.0% (v/v), and a least one zwitterionic detergent, wherein the zwitterionic detergent concentration is between about 0.1× to 400×CMC.

12. The method of claim 1, wherein amplifying the plurality of microbial genetic materials comprises creating amplicons between about 400 to 2000 bp.

13. The method of claim 1, wherein the one or more DIANAs comprise one or more linkers, and optionally wherein the linkers are between about 40 to 200 atoms in length.

14. The method of claim 1, wherein the one or more DIANAs comprise one or more binding moieties.

* * * * *